(12) United States Patent
Plemper et al.

(10) Patent No.: US 10,100,372 B2
(45) Date of Patent: Oct. 16, 2018

(54) RECOMBINANT RSV REPORTER VIRUS

(71) Applicant: Georgia State University and Research Foundation, Inc., Atlanta, GA (US)

(72) Inventors: Richard K. Plemper, Decatur, GA (US); Dan Yan, Lilburn, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/319,642

(22) PCT Filed: Jun. 18, 2015

(86) PCT No.: PCT/US2015/036499
§ 371 (c)(1),
(2) Date: Dec. 16, 2016

(87) PCT Pub. No.: WO2015/195961
PCT Pub. Date: Dec. 23, 2015

(65) Prior Publication Data
US 2017/0130279 A1    May 11, 2017

Related U.S. Application Data

(60) Provisional application No. 62/013,905, filed on Jun. 18, 2014.

(51) Int. Cl.
*C12Q 1/70* (2006.01)
*C12N 9/02* (2006.01)

(52) U.S. Cl.
CPC .............. *C12Q 1/70* (2013.01); *C12N 9/0069* (2013.01); *C12Y 113/12005* (2013.01); *C12Y 113/12007* (2013.01); *C12N 2760/18521* (2013.01); *C12N 2760/18543* (2013.01)

(58) Field of Classification Search
None
See application file for complete search history.

(56) References Cited

U.S. PATENT DOCUMENTS

| | | |
|---|---|---|
| 2010/0239617 A1 | 9/2010 | Pushko et al. |
| 2011/0105423 A1* | 5/2011 | Shaw ............... A61K 31/00 514/34 |
| 2012/0264217 A1 | 10/2012 | Moore et al. |
| 2013/0122032 A1 | 5/2013 | Smith et al. |

FOREIGN PATENT DOCUMENTS

WO    2013139911 A1    9/2013

OTHER PUBLICATIONS

Morton et al., Virology vol. 311 (2003) pp. 275-288.*
Hotard et al., Virology. Dec. 5, 2012;434(1):129-36.*
Yan et al., J Virology 2013 vol. 87, pp. 11076-11087.*
Cianci, et al., "Orally Active Fusion Inhibitors of Respiratory Syncytial Virus", Antimicrobial Agents and Chemotherapy vol. 48 No. 2, 2004, pp. 413-422.
International Search Report and Written Opinion, issued in International Application No. PCT/US15/36499, dated Sep. 29, 2015.
International Preliminary Report on Patentability, issued in International Application No. PCT/US15/36499, dated Dec. 29, 2016.
Yan, et al., "Cross-resistance mechanism of respiratory syncytial virus against structurally diverse entry inhibitors", Instit. for Biomed. Sci 2014, 9 pages.
Thompson WW, et al. (2003) Mortality associated with influenza and resp

(56) References Cited

OTHER PUBLICATIONS

Mahadevia PJ, Makari D, & Masaquel A (2012) Methodological concerns regarding cost-effectiveness analysis of palivizumab in Florida Medicaid. *Arch Pediatr Adolesc Med* 166(10):968-969; author reply 969-970.

Kamal-Bahl S, Doshi J, & Campbell J (2002) Economic analyses of respiratory syncytial virus immunoprophylaxis in high-risk infants: a systematic review. *Arch Pediatr Adolesc Med* 156(10):1034-1041.

Hampp C, Kauf TL, Saidi AS, & Winterstein AG (2011) Cost-effectiveness of respiratory syncytial virus prophylaxis in various indications. *Arch Pediatr Adolesc Med* 165(6):498-505.

de Vries RD, Mesman AW, Geijtenbeek TB, Duprex WP, & de Swart RL (2012) The pathogenesis of measles. *Curr Opin Virol* 2(3):248-255.

Griffin DE (2010) Measles virus-induced suppression of immune responses. *Immunol Rev* 236:176-189.

DeVincenzo JP, El Saleeby CM, & Bush AJ (2005) Respiratory syncytial virus load predicts disease severity in previously healthy infants. *J Infect Dis* 191(11):1861-1868.

El Saleeby CM, Bush AJ, Harrison LM, Aitken JA, & Devincenzo JP (2011) Respiratory syncytial virus load, viral dynamics, and disease severity in previously healthy naturally infected children. *J Infect Dis* 204(7):996-1002.

Teng MN, Whitehead SS, & Collins PL (2001) Contribution of the respiratory syncytial virus G glycoprotein and its secreted and membrane-bound forms to virus replication in vitro and in vivo. *Virology* 289(2):283-296.

Radecke F, et al. (1995) Rescue of measles viruses from cloned DNA. *EMBO J* 14(23):5773-5784.

Berkhout B, Eggink D, & Sanders RW (2012) Is there a future for antiviral fusion inhibitors? *Curr Opin Virol* 2(1):50-59.

Hotard AL, et al. (2012) A stabilized respiratory syncytial virus reverse genetics system amenable to recombination-mediated mutagenesis. *Virology* 434(1):129-136.

Moore TW, et al. (2013) Synthesis and Metabolic Studies of Host Directed Inhibitors for Anti Viral Therapy. *ACS Med Chem Lett* 4(8):762-767.

Boutros M, Bras LP, & Huber W (2006) Analysis of cell-based RNAi screens. *Genome Biol* 7(7):R66, 11 pages.

Pelz O, Gilsdorf M, & Boutros M (2010) web cellHTS2: a web-application for the analysis of high-throughput screening data. *BMC Bioinformatics* 11:185, 6 pages.

Dochow M, Krumm SA, Crowe JE, Jr., Moore ML, & Plemper RK (2012) Independent structural domains in paramyxovirus polymerase protein. *J Biol Chem* 287(9):6878-6891.

Kondo N, Miyauchi K, & Matsuda Z (2011) Monitoring viral-mediated membrane fusion using fluorescent reporter methods. *Curr Protoc Cell Biol* Chapter 26:Unit 26 29.

Brindley MA, Takeda M, Plattet P, & Plemper RK (2012) Triggering the measles virus membrane fusion machinery. *Proc Natl Acad Sci U S A* 109(44):E3018-3027.

Brindley MA, et al. (2013) a stabilized headless measles virus attachment protein stalk efficiently triggers membrane fusion. *J Virol* 87(21):11693-11703.

Plemper RK & Compans RW (2003) Mutations in the putative HR-C region of the measles virus F2 glycoprotein modulate syncytium formation. *J Virol* 77(7):4181-4190.

Stokes KL, et al. (2011) Differential pathogenesis of respiratory syncytial virus clinical isolates in BALB/c mice. *J Virol* 85(12):5782-5793.

Lee S, et al. (2012) Vaccine-elicited CD8+ T cells protect against respiratory syncytial virus strain A2-line19F-induced pathogenesis in BALB/c mice. *J Virol* 86(23):13016-13024.

Yan D, et al. (2013) Dual myxovirus screen identifies a small-molecule agonist of the host antiviral response. *J Virol* 87(20):11076-11087.

Krumm SA, et al. (2011) Potent host-directed small-molecule inhibitors of myxovirus RNA-dependent RNA-polymerases. *PLoS One* 6(5):e20069.

Moore ML, et al. (2009) A chimeric A2 strain of respiratory syncytial virus (RSV) with the fusion protein of RSV strain line 19 exhibits enhanced viral load, mucus, and airway dysfunction. *J Virol* 83(9):4185-4194.

Cianci C, et al. (2004) Targeting a binding pocket within the trimer-of-hairpins: small-molecule inhibition of viral fusion. *Proc Natl Acad Sci U S A* 101(42):15046-15051.

McLellan JS, et al. (2013) Structure-based design of a fusion glycoprotein vaccine for respiratory syncytial virus. *Science* 342(6158):592-598.

McLellan JS, Yang Y, Graham BS, & Kwong PD (2011) Structure of respiratory syncytial virus fusion glycoprotein in the postfusion conformation reveals preservation of neutralizing epitopes. *J Virol* 85(15):7788-7796.

Swanson KA, et al. (2011) Structural basis for immunization with postfusion respiratory syncytial virus fusion F glycoprotein (RSV F) to elicit high neutralizing antibody titers. *Proc Natl Acad Sci U S A* 108(23):9619-9624.

Johnson JE, Gonzales RA, Olson SJ, Wright PF, & Graham BS (2007) the histopathology of fatal untreated human respiratory syncytial virus infection. *Mod Pathol* 20(1):108-119.

Hancock GE, et al. (1996) Generation of atypical pulmonary inflammatory responses in BALB/c mice after immunization with the native attachment (G) glycoprotein of respiratory syncytial virus. *J Virol* 70(11):7783-7791.

Murphy BR, Sotnikov AV, Lawrence LA, Banks SM, & Prince GA (1990) Enhanced pulmonary histopathology is observed in cotton rats immunized with formalin-inactivated respiratory syncytial virus (RSV) or purified F glycoprotein and challenged with RSV 3-6 months after immunization. *Vaccine* 8(5):497-502.

Kapikian AZ, Mitchell RH, Chanock RM, Shvedoff RA, & Stewart CE (1969) An epidemiologic study of altered clinical reactivity to respiratory syncytial (RS) virus infection in children previously vaccinated with an inactivated RS virus vaccine. *Am J Epidemiol* 89(4):405-421.

Kim HW, et al. (1969) Respiratory syncytial virus disease in infants despite prior administration of antigenic inactivated vaccine. *Am J Epidemiol* 89(4):422-434.

Collins PL & Melero JA (2011) Progress in understanding and controlling respiratory syncytial virus: still crazy after all these years. *Virus Res* 162(1-2):80-99.

Roymans D, et al. (2010) Binding of a potent small-molecule inhibitor of six-helix bundle formation requires interactions with both heptad-repeats of the RSV fusion protein. *Proc Natl Acad Sci U S A* 107(1):308-313.

Douglas JL, et al. (2005) Small molecules VP-14637 and JNJ-2408068 inhibit respiratory syncytial virus fusion by similar mechanisms. *Antimicrob Agents Chemother* 49(6):2460-2466.

Lamb RA & Parks GD (2007) Paramyxoviridae: The viruses and their replication. *Fields Virology*, eds Knipe DM & Howley PM (Wolters Kluwer/Lippincott Williams & Wilkins, Philadelphia), 5 Ed vol. 1, pp. 1449-1496.

Morton CJ, et al. (2003) Structural characterization of respiratory syncytial virus fusion inhibitor escape mutants: homology model of the F protein and a syncytium formation assay. *Virology* 311(2):275-288.

Plemper RK (2011) Cell entry of enveloped viruses. *Curr Opin Virol* 1(2):92-100.

Techaarpornkul S, Barretto N, & Peeples ME (2001) Functional analysis of recombinant respiratory syncytial virus deletion mutants lacking the small hydrophobic and/or attachment glycoprotein gene. *J Virol* 75(15):6825-6834.

Techaarpornkul S, Collins PL, & Peeples ME (2002) Respiratory syncytial virus with the fusion protein as its only viral glycoprotein is less dependent on cellular glycosaminoglycans for attachment than complete virus. *Virology* 294(2):296-304.

Lee JK, Prussia A, Snyder JP, & Plemper RK (2007) Reversible inhibition of the fusion activity of measles virus F protein by an engineered intersubunit disulfide bridge. *J Virol* 81(16):8821-8826.

(56) References Cited

OTHER PUBLICATIONS

Yin HS, Wen X, Paterson RG, Lamb RA, & Jardetzky TS (2006) Structure of the parainfluenza virus 5 F protein in its metastable, prefusion conformation. *Nature* 439(7072):38-44.

Doyle J, et al. (2006) Two domains that control prefusion stability and transport competence of the measles virus fusion protein. *J Virol* 80(3):1524-1536.

Eggink D, et al. (2009) Detailed mechanistic insights into HIV-1 sensitivity to three generations of fusion inhibitors. *J Biol Chem* 284(39):26941-26950.

Baldwin CE, et al. (2004) Emergence of a drug-dependent human immunodeficiency virus type 1 variant during therapy with the T20 fusion inhibitor. *J Virol* 78(22):12428-12437.

Reeves JD, et al. (2005) Enfuvirtide resistance mutations: impact on human immunodeficiency virus envelope function, entry inhibitor sensitivity, and virus neutralization. *J Virol* 79(8):4991-4999.

Lukacs NW, et al. (2006) Differential immune responses and pulmonary pathophysiology are induced by two different strains of respiratory syncytial virus. *Am J Pathol* 169(3):977-986.

\* cited by examiner

- recRSV A2-L19F (EC$_{50}$ = 0.13 μM (0.1-0.17); SI > 190)
- RSV 2-20 (EC$_{50}$ = 0.38 μM (0.25-0.57); SI > 65)
- recMeV-Edm (EC$_{50}$ n.d.)
- recIAV-WSN (EC$_{50}$ n.d.)

| resistant sites (AA) | mutations |
|---|---|
| 400 | T-A |
| 401 | D-E |
| 486 | D-E |
| 488 | F-I |
| 488 | F-S |
| 489 | D-E |

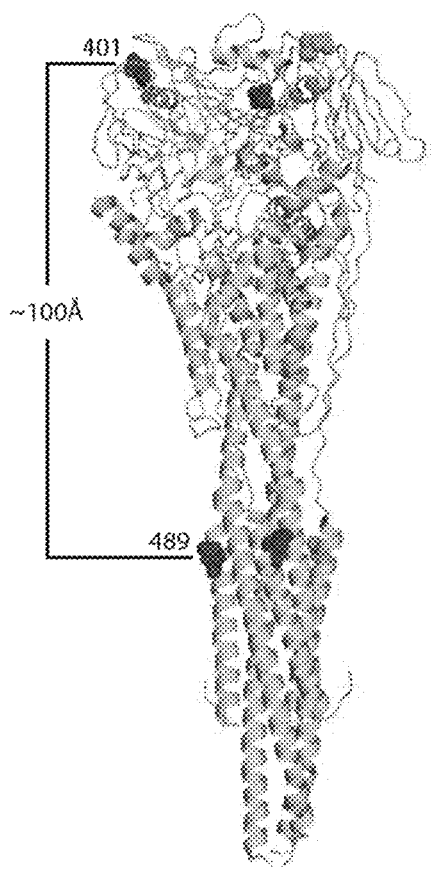 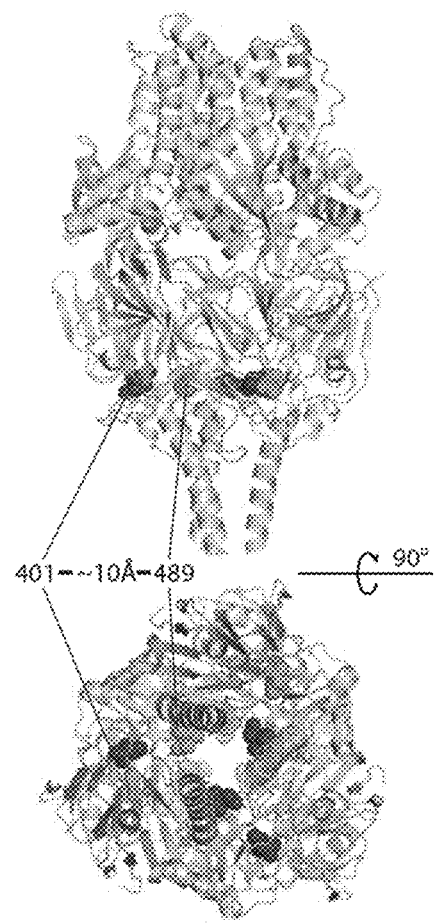
*Figures 4B*  *Figures 4C*

| F construct | max. fusion rate [ΔRLU x10²/hour] | |
|---|---|---|
| | 37°C (0-3 hour interval) | 32°C (2-6 hour interval) |
| RSV L19-F | 4 ± 1.3 | 2.9 ± 0.66 |
| RSV L19-F$_{D401E}$ | 5.6 ± 1.4 | 5.3 ± 0.9 |
| RSV L19-F$_{D489E}$ | 7.5 ± 1.3 | 4.4 ± 1 |
| RSV L19-F$_{D401E/D489E}$ | 6.3 ± 1.6 | 29.3 ± 4.1 |

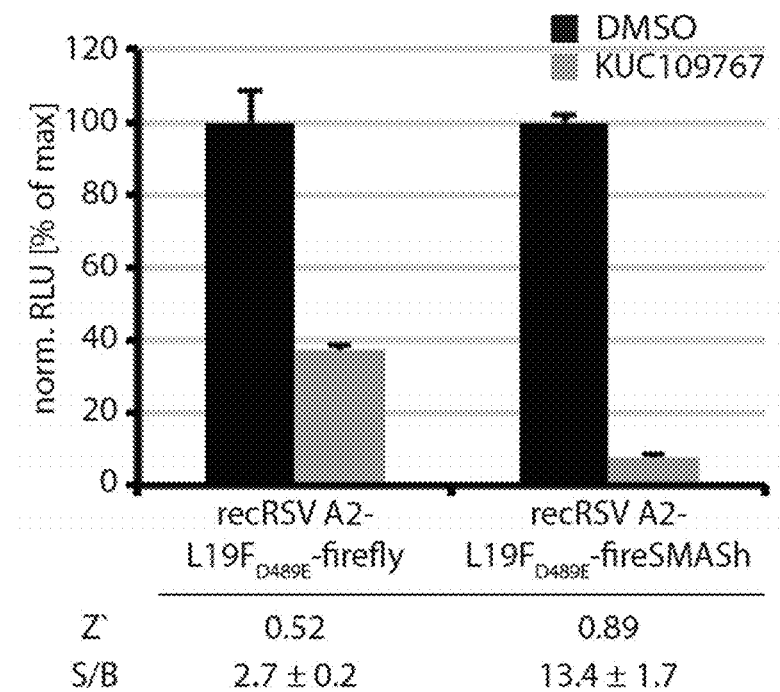
*Figure 14G*
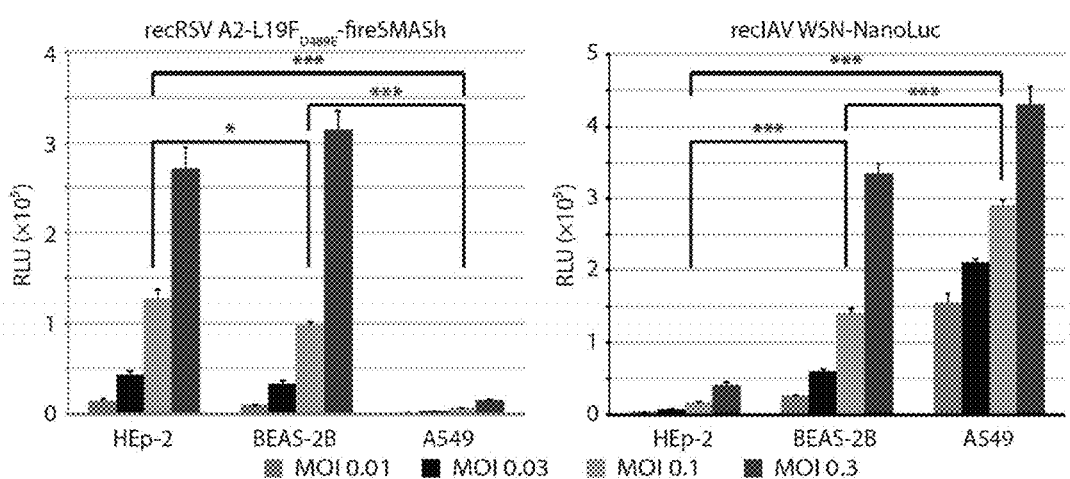
*Figure 15A*          *Figure 15B*

RECOMBINANT RSV REPORTER VIRUS

CROSS-REFERENCE TO RELATED APPLICATIONS

This application claims benefit of U.S. Provisional Application No. 62/013,905, filed Jun. 18, 2014, which is hereby incorporated herein by reference in its entirety.

STATEMENT REGARDING FEDERALLY SPONSORED RESEARCH OR DEVELOPMENT

This invention was made with Government Support under Grant Nos. AI087798, AI095227, AI071002, and HD079327 awarded by the National Institutes of Health. The Government has certain rights in the invention.

BACKGROUND

Respiratory Syncytial Virus (RSV) is a member of the paramyxovirus family, which consists of mostly highly contagious non-segmented, negative polarity RNA viruses that spread through the respiratory route. RSV disease is the leading cause of virus infection-induced death among children below one year of age (Thompson W W, et al. (2003) JAMA 289(2):179-186) and can be life-threatening to the elderly and the immunocompromised (Elliot A J, et al. (2008) Expert Rev Vaccines 7(2):249-258; Ebbert J O, et al. (2005) Respiration 72(3):263-269). Reinfection with RSV can occur throughout life, but infants born prematurely, with bronchopulmonary dysplasia or a congenital heart defect are at highest risk of developing severe disease (Mahadevia P J, et al. (2012) J Med Econ 15(5):987-996). In a typical case, initial RSV infection of airway epithelia cells is followed by rapid spread from the nasopharynx to the lower airways that can affect respiratory function through excessive mucus, necrotic epithelial debris, and inflammatory cells obstructing the airways (Aherne W, et al. (1970) J Clin Pathol 23(1):7-18; Lugo R A, et al. (1993) Clin Pharm 12(2):95-116).

Attempts to develop an effective RSV vaccine have been fruitless thus far, since the virus is poorly immunogenic overall and neutralizing antibody titers wane quickly post infection. Although ribavirin was approved for RSV treatment, clinical use is minimal due to efficacy and toxicity issues (Anderson L J, et al. (1990) J Infect Dis 161(4):640-646; Hall C B, et al. (1993) Pediatrics 92(3):501-504). The humanized neutralizing antibody palivizumab is used for immunoprophylaxis of high-risk pediatric patients, but high costs prohibit broad scale implementation (Mahadevia P J, et al. (2012) J Med Econ 15(5):987-996; Broor S, et al. (2007) PLoS One 2(6):e491; Mahadevia P J, et al. (2012) Arch Pediatr Adolesc Med 166(10):968-969; author reply 969-970; Kamal-Bahl S, et al. (2002) Arch Pediatr Adolesc Med 156(10):1034-1041; Hampp C, et al. (2011) Arch Pediatr Adolesc Med 165(6):498-505).

Clinical disease associated with infection by several paramyxoviruses such as mumps virus or measles virus (MeV) originate predominantly from immunopathogenic effects, which makes therapeutic treatment challenging, since viral replication is typically immune-controlled and titers decline when symptoms become manifest (de Vries R D, et al. (2012) Curr Opin Virol 2(3):248-255; Griffin D E (2010) Immunol Rev 236:176-189). In the case of RSV infection; however, several studies have suggested that pathogenesis is not the result of host immunopathology alone. Rather, higher viral loads were recognized as a predictor for severe lower respiratory infection in infants (DeVincenzo J P, et al. (2005) J Infect Dis 191(11):1861-1868), and RSV titers on day three of hospitalization were indicative for increased need for intensive care in hospitalized children less than two years old (El Saleeby C M, et al. (2011) J Infect Dis 204(7):996-1002). These observations suggest that efficacious therapeutics given early to hospitalized children may improve downstream morbidity and reduce immunopathology, opening a window for improved disease management and making RSV a premier target for drug discovery campaigns.

However, large scale screening campaigns to identify novel therapeutic candidates against RSV have been compromised thus far by the lack of appropriate reporter strains. Moreover, previous anti-RSV drug discovery campaigns have yielded several structurally distinct, highly potent, small-molecule entry inhibitor classes that often lead to drug resistant escape mutations.

SUMMARY

After treatment with entry inhibitors, escape mutations are shown to accumulate in fusion (F) protein microdomains that govern the structural stability of the prefusion complex. Refolding rates of these conformationally destabilized mutant F trimers are enhanced, resulting in a hyperfusogenic phenotype and, possibly, a narrowed window of opportunity for small-molecule docking and interference with F trimer rearrangements leading to fusion pore formation. Therefore, RSV entry inhibitors currently considered for clinical use are at risk to rapidly lose therapeutic benefit in the clinic due to preexisting viral resistance.

An RSV reporter strain containing escape mutations that can be used for high-throughput drug discovery is disclosed. The disclosed RSV reporter strain has one or more mutations in its fusion (F) protein that allows it to escape from entry inhibitors, such as GPAR-3710. The disclosed RSV strain can therefore be used to identify drug candidates that either act post-entry or block viral entry without being compromised by pan-resistance. Also disclosed is a recombinant RSV vector that contains an RSV genome for the disclosed RSV strain operably linked to an expression control sequence. Also disclosed is an infectious RSV virion produced by expression of the disclosed recombinant RSV vector in a host cell. Also disclosed are methods of screening for antiviral agents using the disclosed RSV reporter strains.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows the results of a test screen of recRSV A2-L19F-renilla against a 10,000-entry compound library. Data for each compound were normalized, scaled, and are plotted by screening scores (z-score). The dashed line marks the hit selection cut-off (10 assay-SD); circled hits maintained >90% RSV inhibition in 0.5 μM concentration counterscreens. FIG. 1B shows structures of compounds GPAR-3710 and GPAR-6506, circled in FIG. 1A. FIG. 1C shows dose-response curves for sourced hit GPAR-3710 against para- and orthomyxoviruses. In addition to the recRSV A2-L19F screening strain, RSV clinical isolate 2-20 was tested. Values are means of three experiments ±SD. Where applicable, $EC_{50}$ concentrations were determined through four-parameter variable slope regression modeling, values in parentheses denote 95%-confidence intervals. $CC_{50}$ concentrations are based on host metabolic activity after 24-hour exposure; highest concentration assessed 25 µM. SI: $CC_{50}/EC_{50}$; n.d. not determined.

FIGS. 2A to 2D demonstrate mechanistic characterization of GPAR-3710. FIG. 2A shows a time-of-addition study of GPAR-3710 in comparison with the broad spectrum RdRp inhibitor JMN3-003. The compound was added at the indicated time points. The arrow marks the time of infection with recRSV A2-L19F-renilla. All samples were harvested 26 hours pI and progeny titers determined by $TCID_{50}$ titration using renilla luciferase activity as readout. Values are means of three experiments ±SD. FIG. 2B shows a quantitative dose-response cell-to-cell fusion assay using the DSP-chimeric reporter proteins and ViviRen renilla luciferase substrate. MeV F and H glycoprotein expression constructs are included for specificity control. Values were normalized for vehicle (DMSO) treated samples and represent means of at least three experiments ±SD. FIG. 2C shows transient RSV luciferase replicon reporter assay to determine viral RdRp activity in the presence of GPAR-3710. The RdRp inhibitor JMN3-003 was used for specificity control. Values were normalized for vehicle (DMSO) treated samples and represent means of three experiments ±SD; n.d. not determined. FIG. 2D shows kinetic virus-to-cell fusion assay using the DSP reporter proteins and EnduRen live cell luciferase substrate. Cells were spin-inoculated with recRSV A2-L19F and shifted from 4° to 37° C. at 0 hours. Values represent means of three experiments ±SD. Mock denotes cell mixtures that remained uninfected.

FIGS. 3A to 3D provide a resistance profile for GPAR-3710. FIG. 3A lists the resistance mutations identified in the RSV F protein through viral adaptation. FIG. 3B is a bar graph showing resistance quantification using transiently expressed RSV L19-F mutants, the DSP-based quantitative cell-to-cell fusion assay and ViviRen luciferase substrate. Values represent means of six experiments ±SD. Datasets were subjected to one-way ANOVA and Bonferroni's multiple comparison post-test; *: $P<0.05$. Mock denotes cells transfected with vector DNA instead of F expression plasmid. FIG. 3C is a series of fluorescence microphotographs of recovered RSV recombinants expressing mKate2 and harboring F mutants instead of standard F. Photographs were taken 44 hours p.i. after incubation in the presence of 10 µM GPAR-3710 or vehicle (DMSO). FIG. 3D is a graph showing growth curves of the recovered RSV recombinants at 37° C. Cell-associated viral titers were determined through $TCID_{50}$ titration using mKate2-derived fluorescence as readout. Values are means of three experiments ±SD.

FIGS. 4A to 4C demonstrate structural mapping of pan-resistance hot spots in pre- and postfusion RSV F. FIG. 4A shows dose-response curves of the four recovered RSV recombinants against GPAR-3710 and, for comparison, the clinically advanced RSV entry inhibitor BMS-433771 and broad spectrum RdRp blocker JMN3-003. Values are mean cell-associated viral titers of three experiments ±SD, EC90 concentrations were calculated as in FIG. 1C when applicable. The highest concentration assessed was 100 µM. FIGS. 4B and 4C are ribbon representations of RSV F in the post- (FIG. 4B; pdb 3RRT) and prefusion (FIG. 4C; pdb 4JHW) conformation. Solid spheres represent for each monomer amino acid side chains at positions 401 and 489, respectively. Side views and, for prefusion F, a view from the viral envelope up are shown.

FIGS. 5A to 5E relate to resistance mutations that alter the F fusion kinetics. FIGS. 5A and 5C show results of kinetic cell-to-cell fusion assays with transiently expressed F mutants, DSP-based luciferase reporter, and EnduRen live cells substrate. Fusion was followed at 37° C. (FIG. 5A) or 32° C. (FIG. 5C) by monitoring reconstituted DSP renilla luciferase activity in 30-minute time intervals. Values are means of four replicates ±SD; *: $P<0.05$, : $P<0.01$, *: $P<0.001$. FIG. 5B shows results of straight-line non-linear fit regression modeling to calculate maximal F-induced fusion rates from datasets shown in FIGS. 5A and 5C. Models are based on time intervals showing in first approximation linear signal increases, and numbers show best-fit slopes ±SEM. FIG. 5D is a blot showing cell surface expression (SF) and whole cell steady-state levels (WCL) of transiently expressed RSV F mutants after incubation of cells at 37° C. Blots were probed with specific antibodies directed against RSV F (precursor F0 and cleaved F1 material is marked) or cellular transferrin receptor (TfR). Numbers denote mean densitometry quantitations of four experiments ±SD, all normalized for TfR and expressed relative to standard L19-F. Mock denotes cells transfected with vector DNA instead of F expression plasmid. FIG. 5E is a blot showing cell surface expression of the L19-FD401E/D489E double mutant after incubation of cells at 32° C. Proteins were harvested after 20 hours and at steady state (44 hours) post-transfection. Blot development and densitometry quantifications as specified in FIG. 5D.

Figures 6A, 6B:
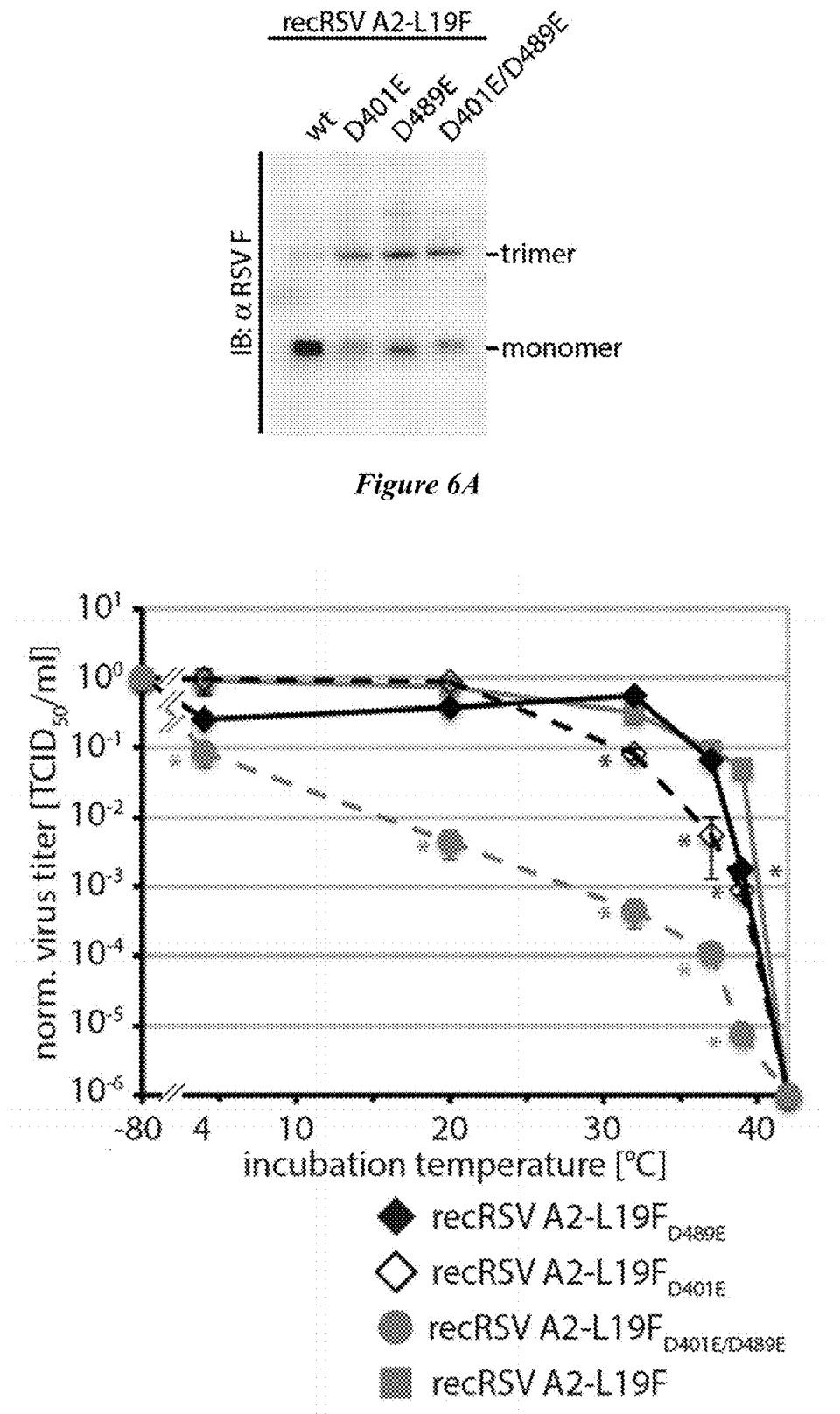

FIGS. 6A to 6D demonstrate stability and in vivo pathogenesis of resistant RSV recombinants. FIG. 6A is a blot from a fusion core assay. F complexes were natively extracted from purified viral particles and fractionated through non-reducing TA-PAGE under mildly denaturing conditions Immunoblots (IB) were probed with specific antibodies directed against the RSV F protein. The migration pattern of F monomers and fusion core-stabilized trimers is indicated; wt: standard L19F. FIG. 6B shows thermal stability of resistant RSV virions. Recombinants were incubated at different temperatures for 24 hours in the absence of target cells, followed by $TCID_{50}$ titration of remaining infectivity. Values were normalized for aliquots immediately stored at −80° C. for 24 hours, and represent means of three experiments ±SD. FIG. 6C shows viral titers from BALB/cJ mice infected intranasally with $1\times10^5$ PFU of the indicated virus, lungs harvested four days p.i. Viral titers were determined through immuno-plaque assays. Symbols represent individual animals of each group (N=5), lines show means±SEM. Cross bars denote statistical analysis of differences between test groups and standard recRSV A2-L19F by one-way ANOVA and Bonferroni's multiple comparison post-test; *: $P<0.05$, NS: not significant. FIG. 6D is a series of images from lungs of BALB/cJ mice infected as in FIG. 6C harvested eight days p.i. and processed for PAS staining. Representative airways are shown, mock denotes lungs of uninfected animals and bars represent 100 µm.

FIG. 7 shows inhibition of recRSV A2-L19F-mKate2 by GPAR-3710. Fluorescence microphotographs of cells infected with recRSV A2-L19F-mKate2 in the presence of the specified compound concentrations or vehicle (DMSO) were taken 44 hours p.i.

reporter. Recovery of the corresponding influenza virus strain harboring this modified PB2-Nluc genome segment resulted in replication-competent recombinants stably expressing Nano-luciferase. The cDNA of PB2 derived from IAV strain WSN-33 (H1N1) is flanked by pol II (positive polarity transcripts) and pol I (negative polarity transcripts) promoters. The natural packaging signal (PS) of PB2 cDNA was silenced and mirrored by a newly constructed PS copy inserted downstream of the Nluc reading frame. An auto-cleavable '2A-like' sequence from porcine teschovirus (PTV) inserted upstream of Nluc allows posttranslational separation of PB2 (restoring bioactivity) and Nluc. A KDEL ER-retention signal is fused to Nluc to prevent secretion of the luciferase protein.

Figure 9:
FIG. 9 shows a schematic of an influenza virus PB2 genome segment containing a Nano luciferase (Nluc)
Figure 10:
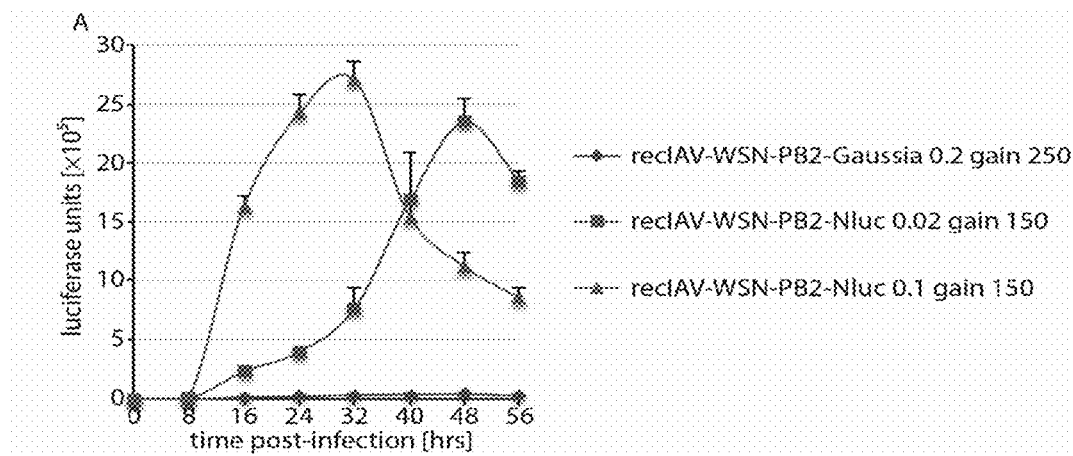

FIG. 10 shows that IAV WSN-Nluc grows efficiently and returns signal intensity approximately one order of magnitude higher than the leading, currently available constructs. Comparison of the IAV WSN-Nluc recombinant with a previously reported IAV WSN-gaussia luc variant, harboring a copy of Gaussia luciferase in the PB2 genome segment in an equivalent design to the approach detailed in FIG. 9. After infection of A549 cells at different multiplicities of infection ranging from 0.02 to 0.2 infectious particles/cell, IAV-WSN-Nluc returns approximately 10-fold higher signal/background values than IAV-WSN-gaussia luc. Values are means of three experiments ±SD.

Figure 11:
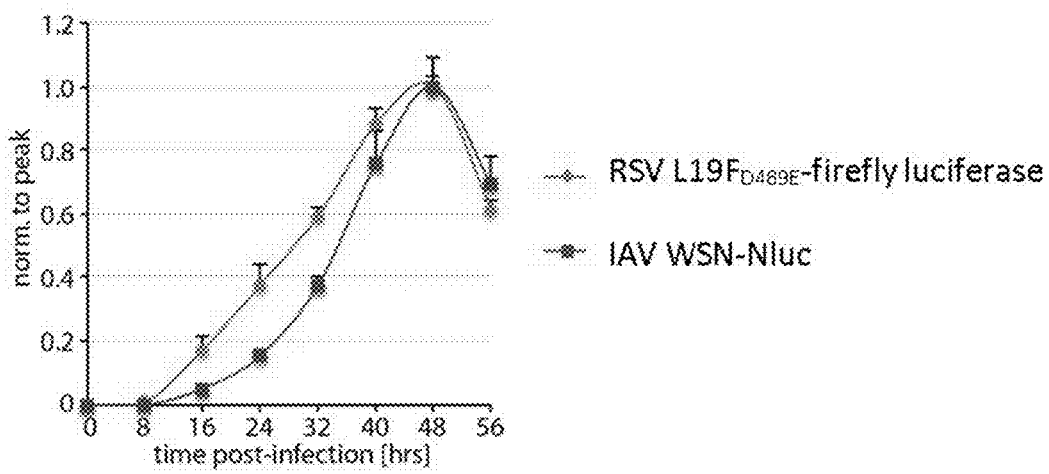

FIG. 11 shows that RSV L19FD489E-firefly luciferase and IAV WSN-Nluc are suitable for dual-pathogen drug screening campaigns. Compatible growth kinetics of RSV L19FD489E-firefly luciferase (MOI=0.1) and IAV WSN-Nluc (MOI=0.02) after co-infection of A549 cells. Samples were harvested and detected at the indicated time post-infection. Values are means of three experiments ±SD.

Figure 12A:
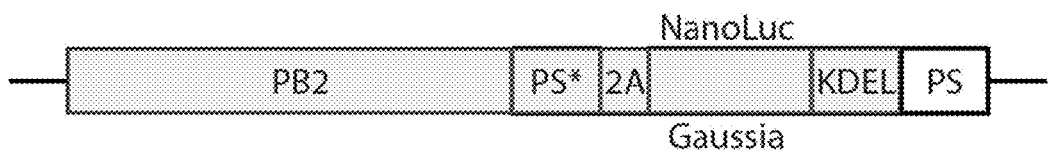
Figure 12B:
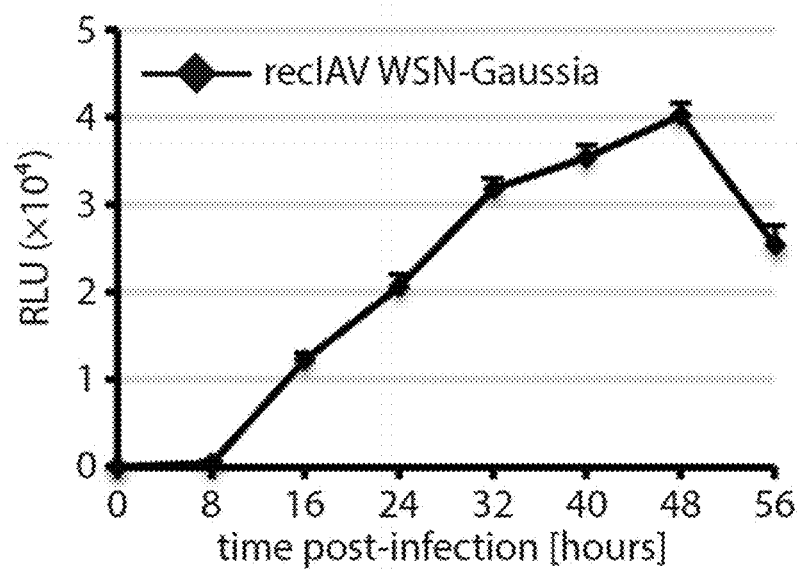
Figure 12C:
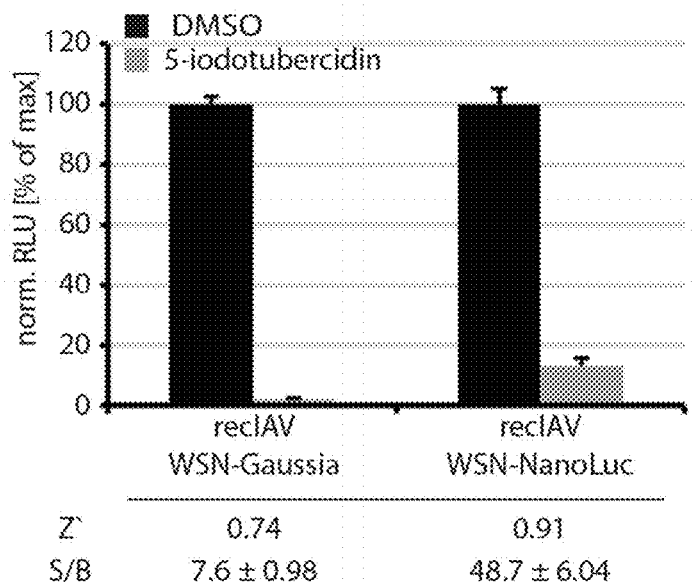
Figure 12D:
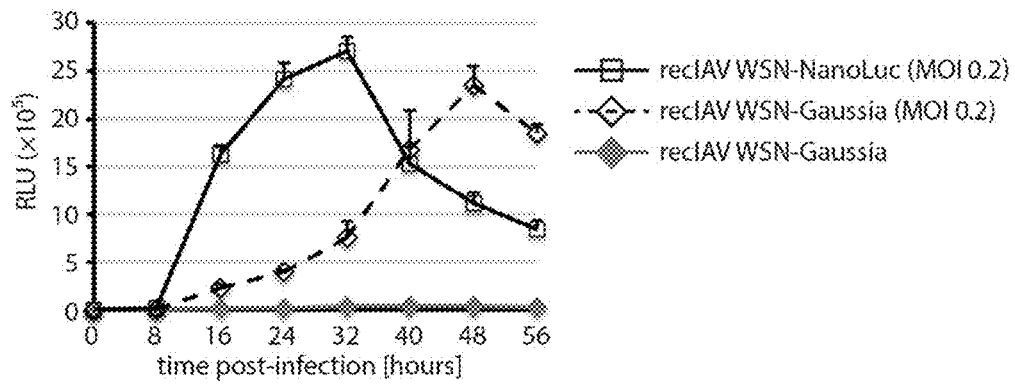
Figure 12E:
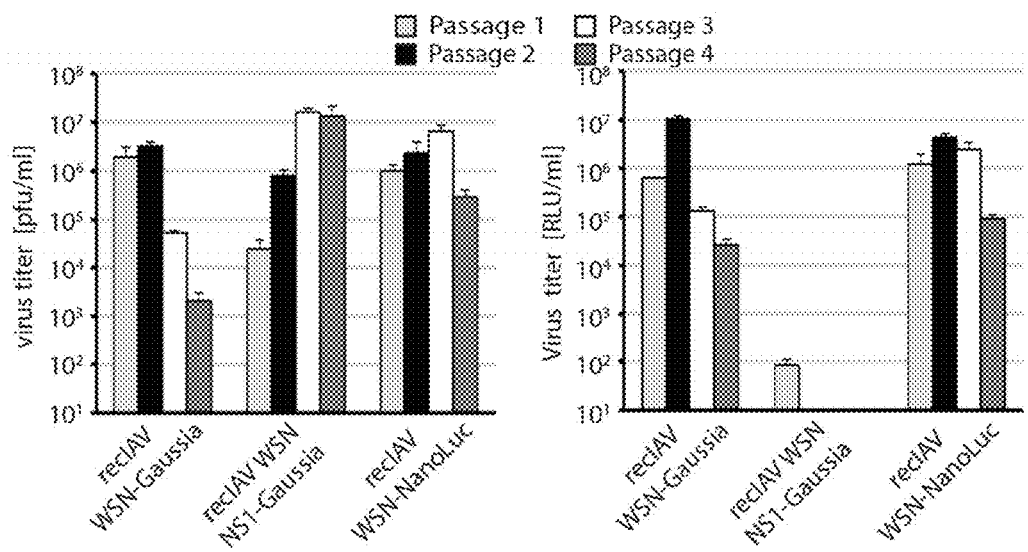

FIGS. 12A to 12E show generation of a recIAV WSN-NanoLuc reporter strain. FIG. 12 A is a schematic of the WSN PB2-NanoLuc or PB2-Gaussia genome segment (PS*: downstream packaging signal that was inactivated through silent mutagenesis; 2A PTV-derived cleavage site; NanoLuc or Gaussia: luciferase ORF; KDEL: ER retention signal; and PS: engineered packaging signal. Grey shading specifies the reading frame of the engineered segment. Individual segments are not drawn to scale. FIG. 12B shows reporter expression profile of IAV WSN-Gaussia on A549 cells (N=3; means±SD are shown). Instrument gain 250; RLU (relative luciferase unit). FIG. 12 shows signal window of the recIAV WSN-Gaussia and analogous recIAV WSN-NanoLuc reporter strains. A549 cells were exposed at infection to the potent inhibitor 5-iodotubercidin at 10 µM or the vehicle (DMSO) volume equivalent. RLUs were determined 48 hours post-infection. Values were normalized for vehicle controls (N=3; means±SD are shown). Z' and S/B values are specified below the graph. FIG. 1D shows reporter expression profiles of recIAV WSN-NanoLuc as in (FIG. 12B) after infection of A549 cells at two different MOIs (N=3; means±SD are shown). Instrument gain 135 for recIAV WSN-NanoLuc. The IAV WSN-Gaussia profile was added for comparison. FIG. 12E shows recIAV WSN-NanoLuc and WSN-Gaussia are genetically stable over several passages. Progeny viral titers were determined by plaque assay (left panel) and luciferase activities determined (right panel) after each passage (N=3; means±SD are shown).

Figure 13A:
Figure 13B:
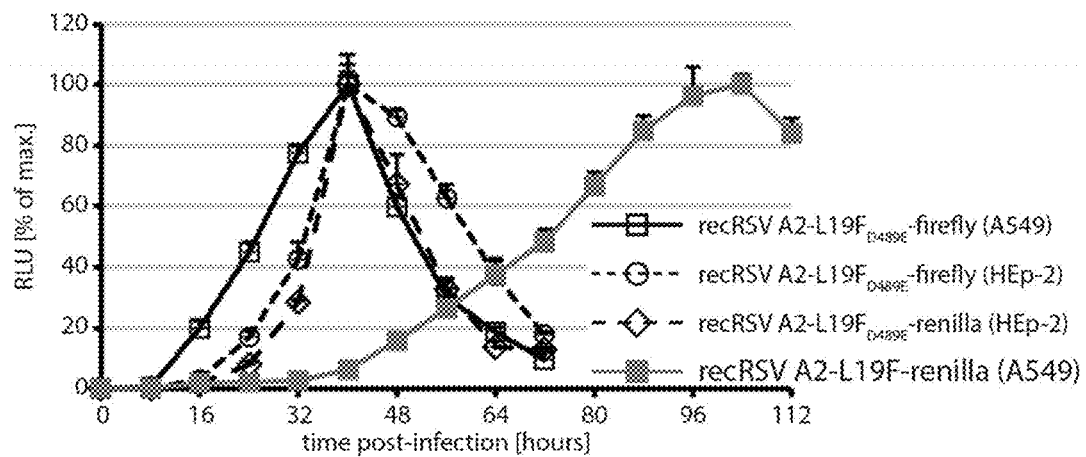
Figure 13C:
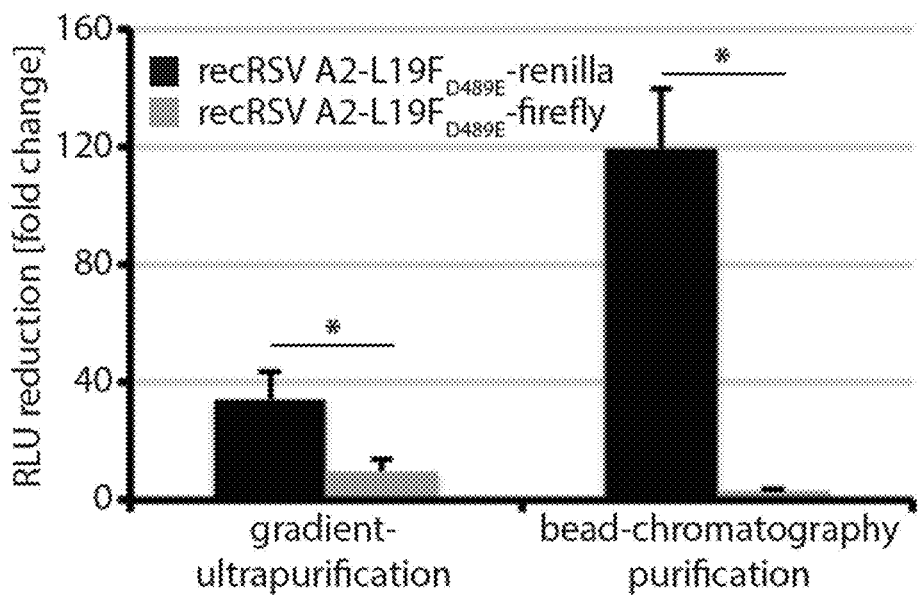
Figure 13D:
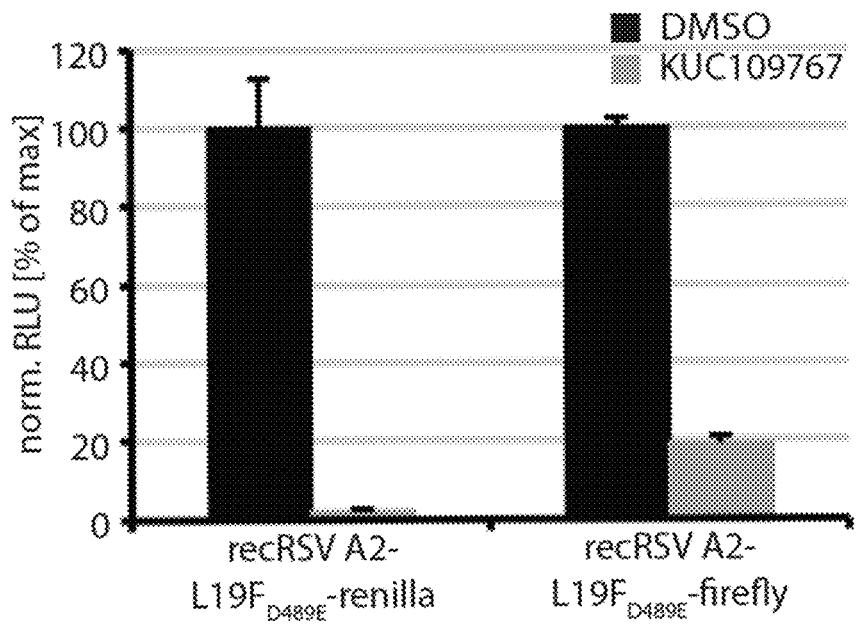

FIGS. 13A to 13D show development of second-generation recRSV reporter strains. FIG. 13A is a schematic of the recRSV-L19F$_{D489E}$-firefly and renilla luciferase genomes. FIG. 13B shows reporter expression profile after infection with recRSV-L19F-renilla or newly generated recRSV-L19F$_{D489E}$-firefly or recRSV-L19F$_{D489E}$-renilla (MOI 0.3 each; instrument gain 200). Values were normalized to the highest signal of each series (N≥3; means±SD are shown). Purification of recRSV-L19F$_{D489E}$-firefly and recRSV-L19F$_{D489E}$-renilla progeny virions through different techniques. FIG. 13C shows background clearance (RLU$_{before}$/RLU$_{after}$) (N=3; means±SD are shown; 2-tailed t-test, *: p<0.05) calculated from virus stocks before and after purification. FIG. 13D shows signal window of the recRSV reporter strains. A549 cells were exposed at infection to 10 µM KUC109767, an inhibitor of RSV RdRp activity, or the vehicle (DMSO) volume equivalent. RLUs were determined 44 hours post-infection and values normalized for vehicle controls (N=3; means±SD are shown).

Figure 14A:
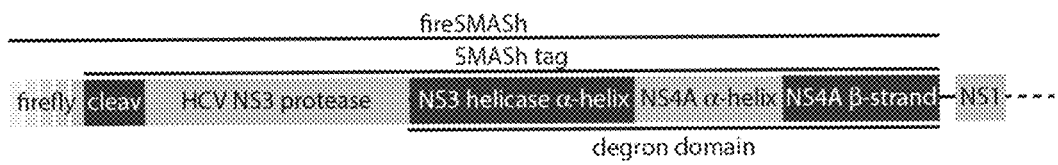
Figure 14B:
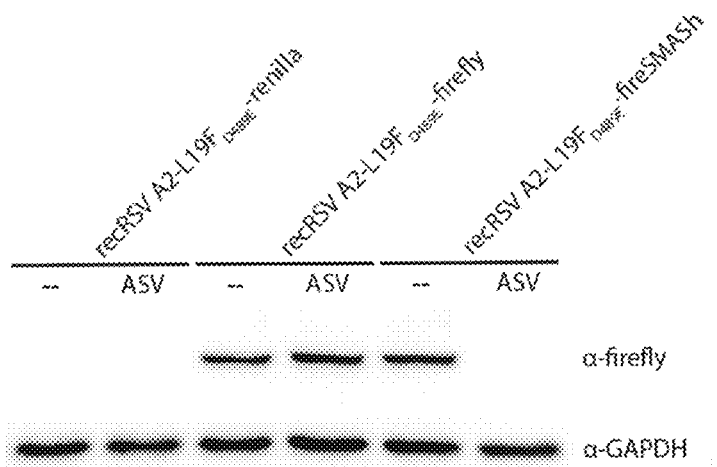
Figure 14C:
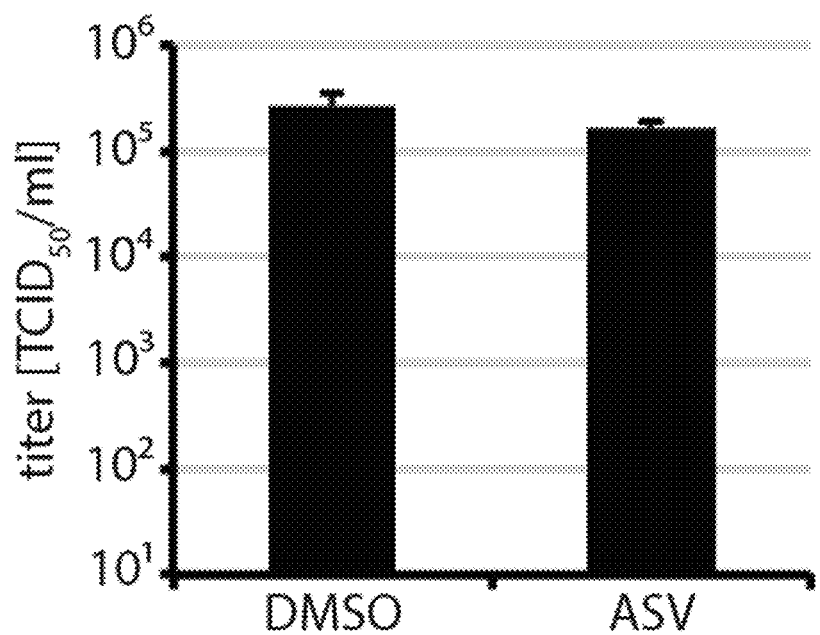
Figure 14D:
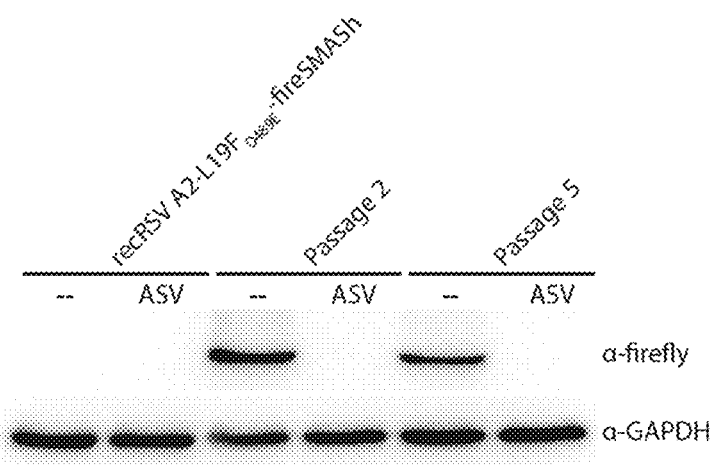
Figure 14E:
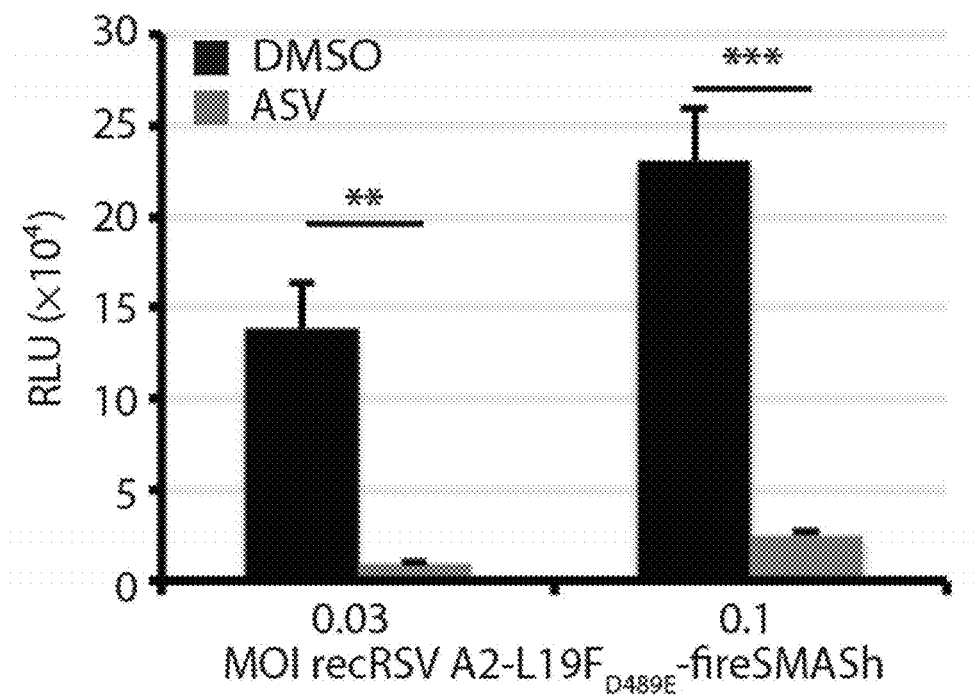
Figure 14F:
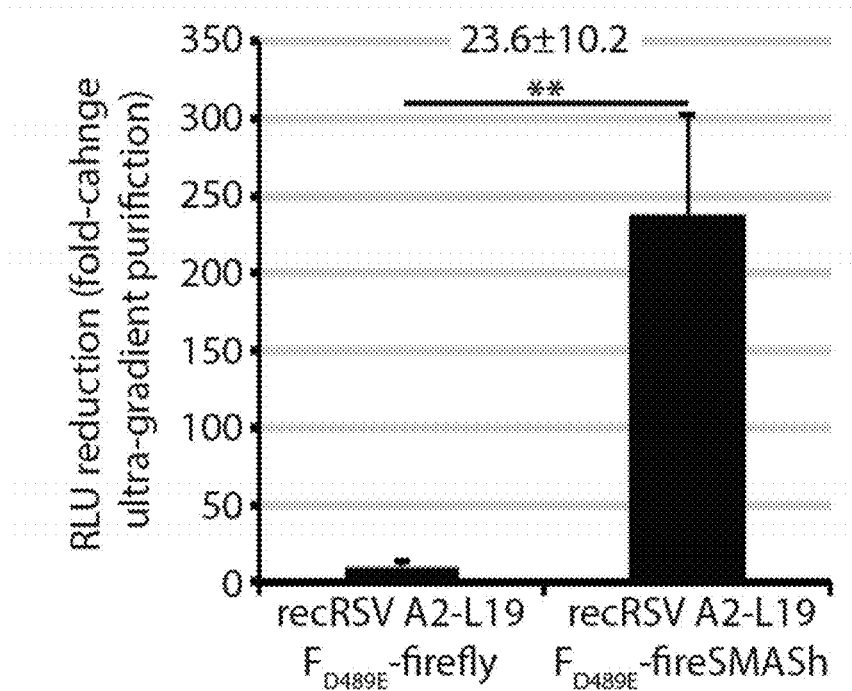

FIGS. 14A to 14G show recRSV-L19F$_{D489E}$-fireSMASh allows induced reporter degradation. FIG. 14A shows schematic of the fireSMASh cassette inserted into the recRSV-L19F$_{D489E}$ genome (cleav: HCV NS3 cleavage site). FIG. 14B shows immunodetection of firefly luciferase after infection of cells with the specified recRSV-L19F$_{D489E}$ strain in the presence or absence of the NS3 inhibitor asunaprevir (ASV) and SDS-PAGE of cell lysates. Cellular GAPDH levels were determined as loading controls. FIG. 14C shows peak recRSV-L19F$_{D489E}$-fireSMASh progeny titers after incubation in the presence of 3 µM ASV or vehicle (DMSO). (N=3; means±SD are shown). FIG. 14D shows immunodetection of firefly luciferase after serial passaging of recRSV-L19F$_{D489E}$-fireSMASh and reinfection of cells in the presence or absence of 3 µM ASV. Passage 2 (P2) and passage 5 (P5) are shown, GAPDH levels were determined as loading controls. FIG. 14E shows firefly activity after growth of recRSV-L19F$_{D489E}$-fireSMASh in the presence or absence of 3 µM ASV. Cells were infected at the specified MOIs and harvested 44 hours post-infection (N=3; means±SD are shown; 2-tailed t-test, : p<0.01; *: p<0.001). FIG. 14F shows fold-change of contaminating firefly luciferase after gradient purification of recRSV-L19F$_{D489E}$-firefly and recRSV-L19F$_{D489E}$-fireSMASh preparation to unpurified recRSV-L19F$_{D489E}$-firefly (N=3; means±SD are shown; 2-tailed t-test; **: p<0.01). FIG. 14G shows signal window of the recRSV-L19F$_{D489E}$-fireSMASh reporter strain was calculated as described in FIG. 13D N=3; means±SD are shown). Z' and S/B values are specified below the graph.

Figure 15C:
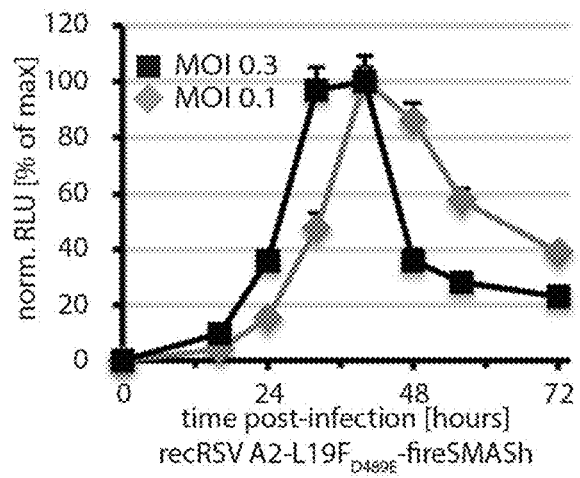
Figure 15D:
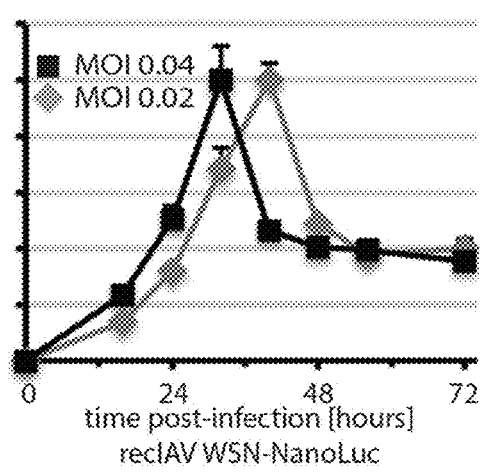
Figure 15E:
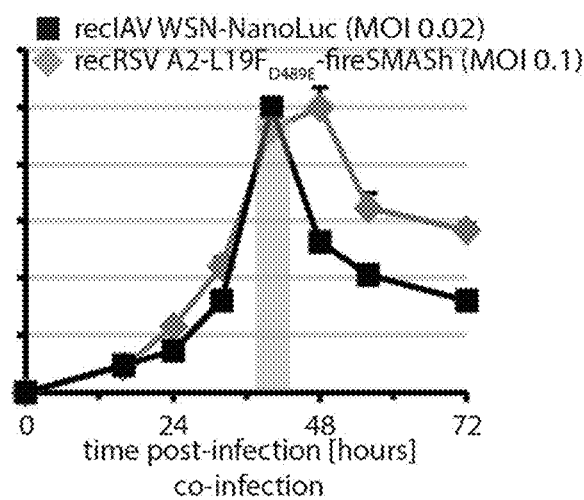

FIGS. 15A to 15E show infection conditions for synchronized RSV and IAV reporter expression. FIGS. 15A and 15B show luciferase activities in three different human respiratory host cell lines 44 hours post-infection at the specified MOIs with recRSV-L19F$_{D489E}$-fireSMASh (FIG. 15A) or recIAV WSN-NanoLuc (FIG. 15B; N=4; means±SD are shown). Two-way ANOVA with Tukey's multiple comparison post-tests were carried out to assess statistical significance of sample divergence. Results are shown for MOI 0.1 (A) and 0.04 (B); *: p<0.05; ***: p<0.01. FIGS. 15C-15E show reporter activity profiles after infection of BEAS-2B cells singly with recRSV-L19F$_{D489E}$-fireSMASh (FIG. 15C) or recIAV WSN-NanoLuc (FIG. 15D), or after co-infection with both strains at an MOI of 0.1 (RSV) and 0.02 (IAV), respectively (FIG. 15E). Values were normalized to the highest signal of each series (N=3; means±SD are shown); grey shaded area in (FIG. 15D) marks the time window post-infection when signal intensities of both luciferase reporters are ≥80% of max.

Figures 16A, 16B:
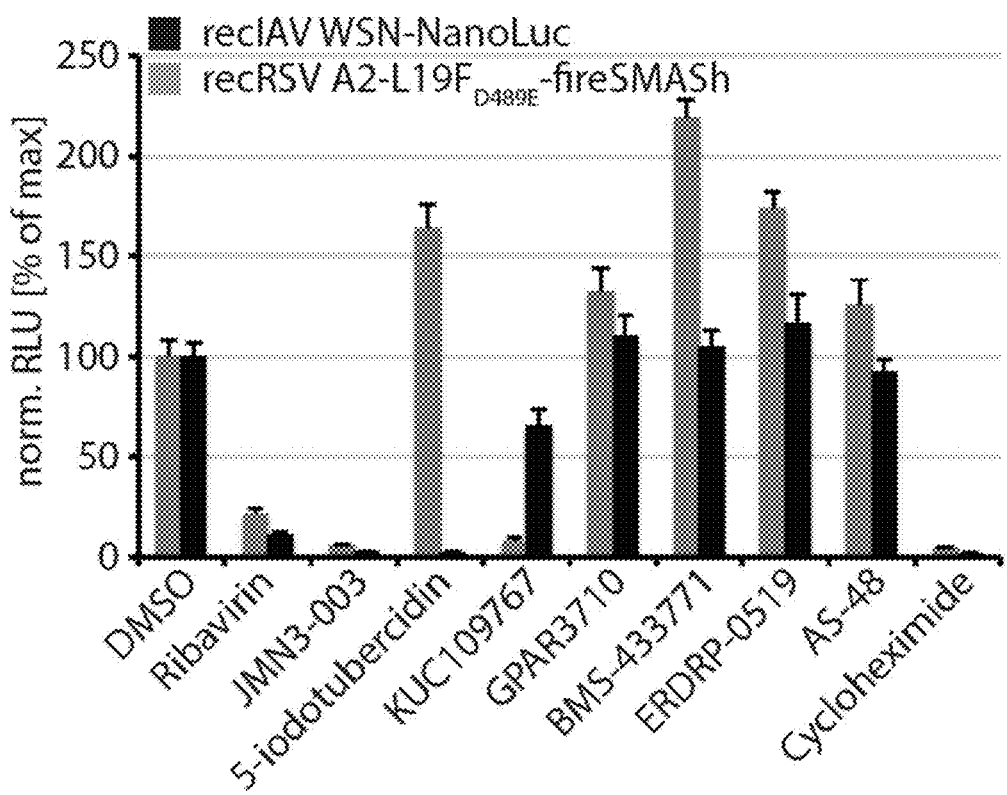
Figure 16C:
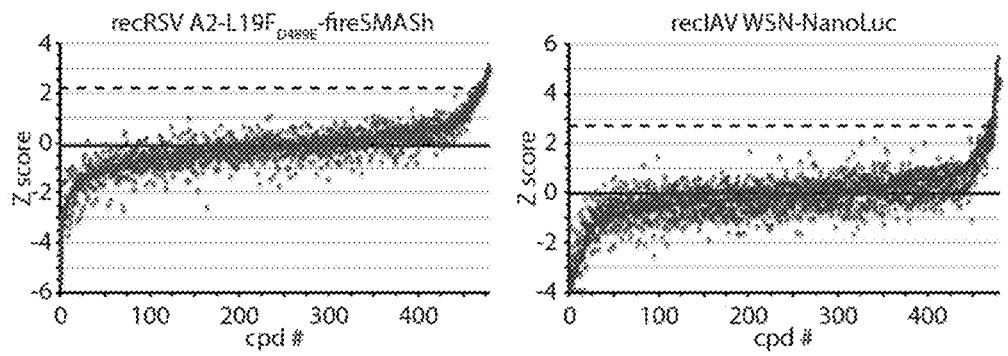
Figure 16D:
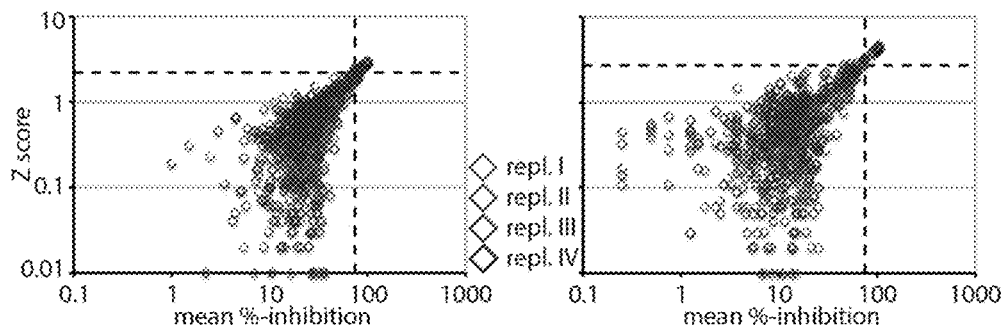

FIGS. 16 to 16D show assay miniaturization and validation. FIG. 16A shows results from co-infection of BEAS-2B cells with recRSV-L19F$_{D489E}$-fireSMASh and recIAV WSN-NanoLuc as specified in FIG. 15E in a 96-well plate format. Known RSV-specific (KUC109767 (10 µM), GPAR3710 (10 µM), and BMS-433771 (10 µM)) IAV-specific (5-iodotubercidin (10 µM)), and MeV-specific inhibitors (ERDRP-0519 (10 µM), AS-48 (40 µM)), broad-spectrum antivirals (ribavirin (40 µM) and JMN3-003 (10 µM)), and cytotoxic cycloheximide (100 µg/ml) were used for assay validation (N=5; means±SD are shown). FIG. 16B shows co-infection assay parameters obtained in 96-well (manual; one plate each; N=5; means±SD are shown) and 384-well (automated; four plates each; N=128; means±SD are shown) format. ND: not determined. FIG. 16C shows Z-score profiles of automated dual-pathogen pilot screens of the NCC collection in 384-well plate format in four replicates. Symbols mark Z-scores of individual replicate screens, solid black lines represent the assay Z-score mean, and dashed black lines show the hit cut-off (assay mean+ 2.5×(assay Z-score SD)). Final screening concentration was 5 µM. FIG. 16D shows individual Z-scores of the replicate (repl. I-IV) screens shown in (FIG. 16C) plotted as a function of the mean %-inhibition for each compound. Dashed horizontal and vertical black lines show hit cut-offs based on Z-score (assay mean+2.5×(assay Z-score SD)) and biological effect (mean inhibition >75%), respectively.

Figure 17A:
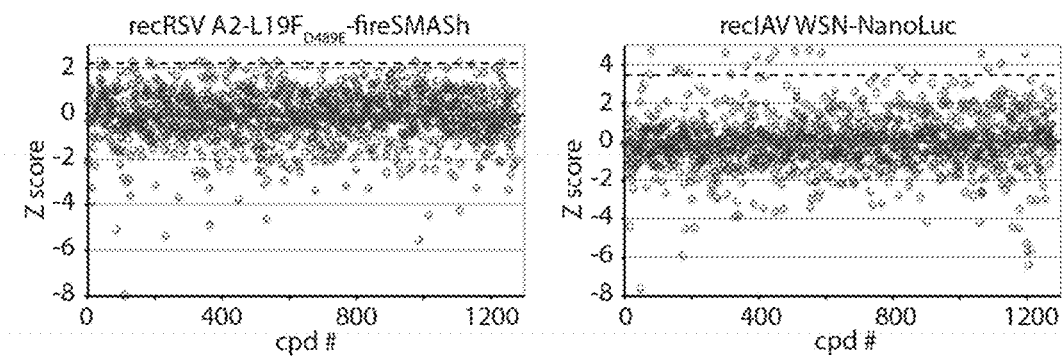
Figure 17B:
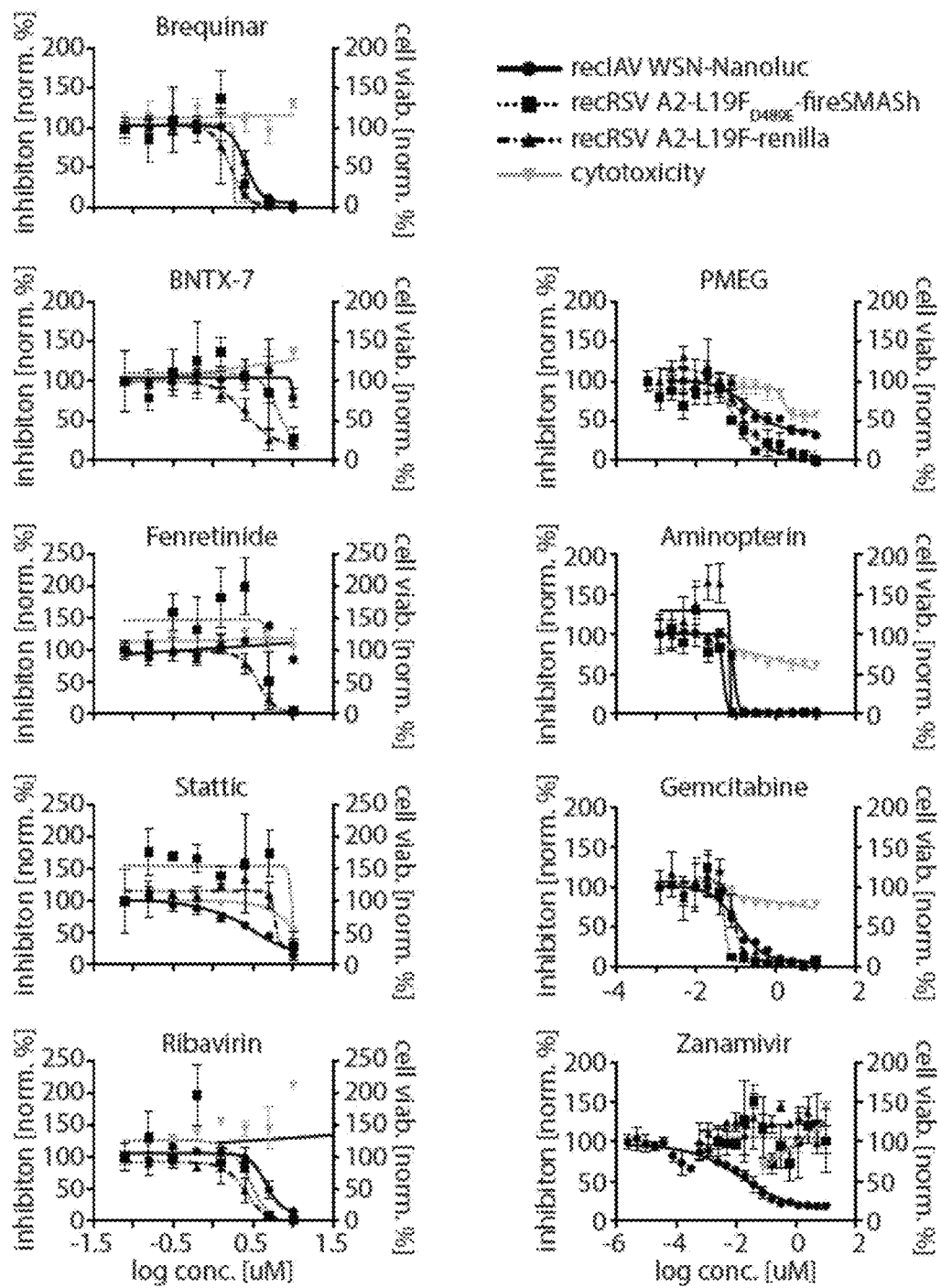

FIGS. 17A and 17B show results of a test screen of a 1280-compound LOPAC library of known bioactives. FIG. 17A shows Z-score profiles of the automated proof-of-concept screen of the LOPAC library in 384-well format. Solid lines show Z-score means, dashed lines hit cut-offs (assay mean+2.0×(assay Z-score SD) for recRSV A2-L19$F_{D489E}$-fireSMASh, assay mean+2.5×(assay Z-score SD) for rec IAV WSN-NanoLuc). Final screening concentration was 5 µM. FIG. 17B shows dose-response assays of hit candidates in a concentration (conc.) range of 10-0.078 or 10-0.0006 µM. Only hits with $CC_{50}$ concentrations ≥10 µM and confirmed inhibition of at least one primary target virus are shown. Values were normalized (norm.) for vehicle (DMSO)-treated infections and represent mean % inhibition or % cell viability (viab.) of three replicates ±SD. Regressions curves for antiviral (solid) or cytotoxic (shaded) activities are based on four-parameter modeling where applicable.

Figure 18:
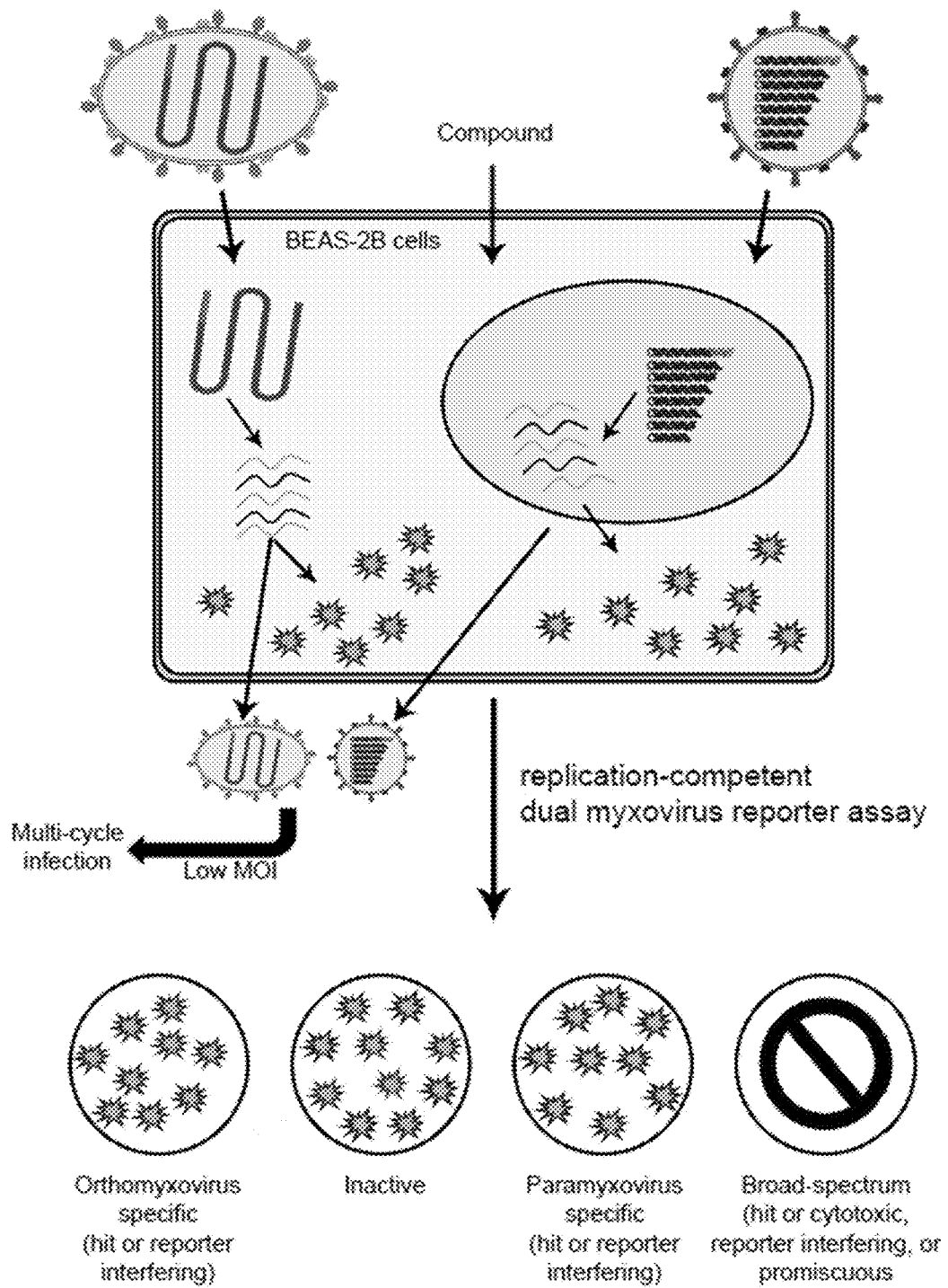

FIG. 18 is an overview of the replication-competent IAV and RSV reporter strain-based next-generation dual pathogen HTS protocol for the simultaneous identification of IAV-specific, RSV-specific, and broad spectrum inhibitors. The assay is validated for human respiratory BEAS-2B cells, but adaptable to all cell lines that are permissive for either virus strain. Infection at high MOI can predominantly identify inhibitors of viral entry and polymerase, while low MOI multi-cycle infections allow interrogation of all stages of the viral live cycle. Counterscreens can be used to distinguish between hit candidates or reporter interfering compounds (specific antiviral activity), and hit candidates, reporter interfering compounds, cytotoxic compounds, or promiscuous pan-assay interfering (PAIN) compounds (broad spectrum activity).

DETAILED DESCRIPTION

An RSV reporter strain that can be used for high-throughput drug discovery is disclosed. The disclosed RSV reporter strain has a mutation in its fusion (F) protein that allows it to escape from entry inhibitors, such as GPAR-3710. The disclosed RSV strain can therefore be used to identify drug candidates that either act post-entry or block viral entry without being compromised by pan-resistance. Also disclosed is a recombinant RSV vector that contains an RSV genome for the disclosed RSV reporter strain operably linked to an expression control sequence. Also disclosed is an infectious RSV virion produce by expression of the disclosed recombinant RSV vector in a host cell.

Typically, an RSV virion/particle contains a viral genome within a helical nucleocapsid which is surrounded by matrix proteins and an envelope containing glycoproteins. The genome of human wild-type RSV encodes the proteins, NS1, NS2, N, P, M, SH, G, F, M2-1, M2-2, and L. NS1 and NS2 inhibit type I interferon activity. N encodes nucleocapsid protein that associates with the genomic RNA forming the nucleocapsid. M encodes the Matrix protein required for viral assembly. SH, G and F form the viral coat. The G protein is a surface protein that is heavily glycosylated. It functions as the attachment protein. The fusion (F) protein mediates fusion, allowing entry of the virus into the cell cytoplasm and also allowing the formation of syncytia. M2 is the second matrix protein also required for transcription and encodes M2-1 (elongation factor) and M2-2 (transcription regulation). L encodes the RNA polymerase. The phosphoprotein P is a cofactor for the L protein.

To produce infectious RSV virions, the RSV genome (or antigenome) expresses the RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, RSV proteins needed for a productive infection can be supplied by coexpression.

The term "RSV genome" as used herein refers to the genomic or antigenomic sequences for the RSV genes necessary to produce an RSV virion, along with optional heterologous genes, operably linked to an expression control sequences.

In some embodiments, the disclosed RSV genome comprises a nucleic acid encoding a fusion (F) protein having a mutation that allows an RSV viron produced by expression of the recombinant RSV vector to escape from GPAR-3710 inhibition. An example amino acid sequence for a wild type F protein is set forth in GenBank accession number ACO83297, SEQ ID NO:1, shown below:

```
  1 melpilkana ittilaavtf cfassqnite efyqstcsav skgylsalrt gwytsvitie 61 lsnikknkcn gtdakvklmk qeldkyknav telqllmqst paannrarre lprfmnytln 121 ntkktnvtls kkrkrrflgf llgvgsaias giavskvlhl egevnkiksa llstnkavvs 181 lsngvsvlts rvldlknyid kqllpivnkq scrisnietv iefqqknnrl leitrefsvn 241 agvttpvsty mltnsellsl indmpitndq kklmsnnvqi vrqqsysims iikeevlayv 301 vqlplygvid tpcwklhtsp lcttntkegs nicltrtdrg wycdnagsvs ffpqaekckv 361 qsnrvfcdtm ysltlpsevn lcnvdifnpk ydckimtskt dvsssvitsl gaivscygkt
```

```
421 kctasnknrg iiktfsngcd yvsnkgvdtv svgntlyyvn kqegkslyvk gepiinfydp 481 lvfpsdefda sisqvnekin qslafirksd ellhnvnagk sttnimitti iiviivills 541 liavglllyc karstpitls kdqlsginni afsn.
```

For example, the F protein can comprises a mutation that corresponds to residue 401 of SEQ ID NO:1, 489 of SEQ ID NO:1, or a combination thereof. Also disclosed is a recombinant nucleic acid that comprises an RSV F protein having a mutation that corresponds to residue 401 of SEQ ID NO:1, 489 of SEQ ID NO:1, or a combination thereof, operably linked to a heterologous expression control sequence. In some cases, the mutation is a D401E mutation, a D489E mutation, or a combination thereof.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino, acids.

A reference RSV genome (or antigenome) can be derived from any suitable native RSV strain. For example, RSV strains can be selected from the group consisting of RSV strain A2 (wild type) (ATCC VR-1540P), RSV strain rA2cp248/404, RSV Strain 2-20, RSV strain 3-12, RSV strain 58-104, RSV strain Long (ATCC VR-26), RSV strain 9320 (ATCC VR-955), RSV strain B WV/14617/85 (ATCC VR-1400), RSV strain 18537 (ATCC VR-1580), RSV strain A2 cpts-248 (ATCC VR-2450), RSV strain A2 cpts-530/1009 (ATCC VR-2451), RSV strain A2 cpts-530 (ATCC VR-2452), RSV strain A2 cpts-248/955 (ATCC VR-2453), RSV strain A2 cpts-248/404 (ATCC VR-2454), RSV strain A2 cpts-530/1030 (ATCC VR-2455), RSV strain subgroup B cp23 Clone 1A2 (ATCC VR-2579), RSV strain Subgroup B, Strain B1, and cp52 Clone 2B5 (ATCC VR-2542). In some cases, the RSV strain RSV strain L19 (ATCC HRSV-L19).

The genomic sequence for strain A2 is set forth in GenBank accession number M74568, SEQ ID NO:2. The genomic sequence for strain line 19 is set forth in GenBank accession number FJ614813, SEQ ID NO:3. The genomic sequence for strain Long is set forth in GenBank accession number AY911262, SEQ ID NO:4.

A reference RSV genome can also be derived from a recombinant or chimeric strain. For example, the RSV genome can be derived from a chimeric A2 strain, wherein the nucleic acid encoding the F protein is derived from an RSV L19 strain. Any other chimeric combinations of NS1, NS2, N, P, M, SH, G, F, M2-1, M2-2, and L genes from two or more RSV strains are contemplated for use in the disclosed RSV constructs.

A variety of alterations in the RSV genome for incorporation into infectious recombinant RSV are possible. For example, foreign genes may be inserted, the order of genes changed, gene overlap removed, the RSV genome promoter replaced with its antigenome counterpart, portions of genes removed (e.g., the cytoplasmic tails of glycoprotein genes), and even entire genes deleted. Modifications in the sequence can be made to facilitate manipulations. Nontranslated gene sequences can be removed to increase capacity for inserting foreign sequences.

Therefore, variants of native or recombinant/chimeric RSV containing an F protein with the disclosed mutations may be used. The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a reference sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The RSV genome can further comprise a nucleic acid encoding a reporter protein, such as a luciferase or fluorescent protein, operably linked to the expression control sequence. For example, the luciferase can be a firefly luciferase or a Renilla luciferase.

A nucleic acid sequence encoding firefly luciferase is set forth in GenBank accession number M15077, SEQ ID NO:5. A synthetic nucleic sequence encoding Renilla luciferase is set forth in GenBank accession number AY004213, SEQ ID NO:6. A synthetic nucleic acid sequence encoding eGFP is set forth in GenBank accession number JQ064508, SEQ ID NO:7.

The RSV genome can further comprise a nucleic acid encoding a tag for quickly shut off the production of the disclosed recombinant protein at a post-transcriptional step. In particular, the tag can involve small molecule-assisted shutoff (SMASh) technology. For example, the tag can include a degradation signal (i.e., degron) and a protease cleavage site that cleaves the degron from the recombinant protein. However, in the presence of a protease inhibitor, autopreolysis can be blocked and the degron induce rapid degradation of the recombinant protein. In some embodiments, the SMASh can comprise a hepatitis C virus-derived NS3 protease flanked by a strong degron domain inducing proteasomal degradation. In these embodiments, the NS3 protease site can be positioned at the intersection of the SMASh tag and the target protein.

The recombinant RSV vector can have the backbone from any suitable expression vector. The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., operably linked to a transcriptional control element).

For example, the RSV vector can have a bacterial artificial chromosome (BAC) backbone. The BAC system is based on *Escherichia coli* and its single-copy plasmid F factor which were described as useful for cloning large fragments of human DNA. The F factor encodes for genes that regulate its own replication including oriS, repE, parA, and parB. The oriS and repE genes mediate the unidirectional replication of the F factor while parA and parB typically maintain copy number at a level of one or two per *E. coli* genome. It is contemplated that the genes and the chromosome may contain mutations, deletions, or variants with desired functional attributes. The BAC vector (pBAC) typically contains these genes as well as a resistance marker and a cloning segment containing promotors for incorporating nucleic acid segments of interest by ligating into restriction enzyme sites.

Methods to construct expression vectors containing genetic sequences and appropriate transcriptional and translational control elements are well known in the art. These methods include in vitro recombinant DNA techniques, synthetic techniques, and in vivo genetic recombination. Such techniques are described in Sambrook et al., Molecular Cloning, A Laboratory Manual (Cold Spring Harbor Press, Plainview, N.Y., 1989), and Ausubel et al., Current Protocols in Molecular Biology (John Wiley & Sons, New York, N.Y., 1989).

Expression vectors generally contain regulatory sequences necessary elements for the translation and/or transcription of the inserted coding sequence. For example, the coding sequence is preferably operably linked to an expression control sequence, such as a promoter and/or enhancer to control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

The term "promoter" refers to a sequence or sequences of DNA that function when in a relatively fixed location in regard to the transcription start site. A "promoter" contains core elements required for basic interaction of RNA polymerase and transcription factors and can contain upstream elements and response elements.

The term "enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression.

An "endogenous" enhancer/promoter is one which is naturally linked with a given gene in the genome. An "exogenous" or "heterologous" enhancer/promoter is one which is placed in juxtaposition to a gene that it does not control in nature by means of genetic manipulation (i.e., molecular biological techniques) such that transcription of that gene is directed by the linked enhancer/promoter.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

Screening Methods

Also disclosed are methods of screening for antiviral agents using the disclosed RSV reporter strains. The methods can involve contacting a culture comprising the disclosed RSV strains or infectious RSV virion with a candidate agent, and then assaying the culture for RSV levels or activity. In these embodiments, a decrease in RSV levels or activity is an indication that the candidate agent is an effective antiviral agent for RSV.

RSV levels or activity can be determined by assaying for reporter expression. Therefore, in some cases, the RSV genome comprises a nucleic acid encoding a first luciferase, and the method involves contacting the culture with a substrate for the first luciferase, and then assaying the culture for bioluminescence. In these embodiments, a decrease in bioluminescence from the first luciferase activity is an indication that the candidate agent is an effective antiviral agent for RSV.

The disclosed RSV strains and viral particles can also be used in combination with other viral strains to detect pan-inhibitors. For example, the culture can further comprise an influenza strain or infectious influenza virion encoded by a recombinant influenza vector that comprises an influenza genome encoding a second luciferase that has a substrate distinct from the first luciferase. For example, the first luciferase can be firefly luciferase, while the second luciferase can be selected from the group consisting of nano-luciferase, gaussia luciferase, and Renilla luciferase. The influenza genome can be derived from any suitable strain, such as strain WSN-33 (H1N1).

An example nucleic acid sequence for a pHW12PBII_Nanoluc-PS construct is set forth in SEQ ID NO:8, shown below:

```
accggagtactggtcgacctccgaagttggggggagcaaaagcagggtgacaaagacataagcgaaagcaggtcaa ttatattcaatatggaaagaataaaagaactaaggaatctaatgtcgcagtctcgcactcgcgagatactcacaaaa accaccgtggaccatatggccataatcaagaagtacacatcaggaagacaggagaagaacccagcacttaggatgaa atggatgatggcaatgaaatatccaattacagcagacaagaggataacggaaatgattcctgagagaaatgagcagg gacaaactttatggagtaaaatgaatgacgccggatcagaccgagtgatggtatcacctctggctgtgacatggtgg
```

-continued aataggaatggaccagtgacaagtacagttcattatccaaaaatctacaaaacttattttgaaaaagtcgaaaggtt aaaacatggaacctttggccctgtccattttagaaaccaagtcaaaatacgtcgaagagttgacataaatcctggtc atgcagatctcagtgccaaagaggcacaggatgtaatcatggaagttgttttccctaacgaagtgggagccaggata ctaacatcggaatcgcaactaacgacaaccaaagagaagaaagaagaactccagggttgcaaaatttctcctctgat ggtggcatacatgttggagagagaactggtccgcaaaacgagattcctccagtggctggtggaacaagcagtgtgt acattgaagtgttgcatttgacccaaggaacatgctgggaacagatgtacactccaggaggggaggcgaggaatgat gatgttgatcaaagcttaattattgctgctagaaacatagtaagaagagccacagtatcagcagatccactagcatc tttattggagatgtgccacagcacgcagattggtggaataaggatggtaaacatccttaggcagaacccaacagaag agcaagccgtggatatttgcaaggctgcaatgggactgagaattagctcatccttcagttttggtggattcacattt aagagaacaagcggatcatcagtcaagagagaggaagaggtgcttacgggcaatcttcagacattgaagataagagt gcatgagggatatgaagagttcacaatggttgggagaagagcaacagctatactcagaaaagcaaccaggagattga ttcagctgatagtgagtgggagagacgaacagtcgattgccgaagcaataattgtggccatggtattttcacaagag gattgtatgataaaagcagttagaggtgacctgaatttcgtcaatagggcgaatcagcgattgaatcccatgcacca acttttgagacattttcagaaggatgcaaaggtgctctttcaaaatttggggaattgaatccatcgacaatgtgatgg gaatgatcgggatattgcccgacatgactccaagcaccgagatgtcaatgagaggagtgagaatcagcaaaatgggg gtagatgagtattccagcgcggagaagatagtggtgagcattgaccgttttttgagagttagggaccaacgtgggaa tgtactactgtctcccgaggagatcagtgaaacacagggaacagagaaactgacaataacttactcatcgtcaatga tgtgggagattaatggtcctgaatcagtgttggtcaatacctatcagtggatcatcagaaactgggaaactgttaaa attcagtggtcccagaatcctacaatgctgtacaataaaatggaatttgagccatttcagtctttagttccaaaggc cgttagaggccaatacagtgggtttgtgagaactctgttccaacaaatgagggatgtgcttgggacatttgataccg ctcagataataaaacttcttcccttcgcagccgctccaccaaagcaaagtagaacgcagttctcctcattgactata aatgtgaggggatcaggaatgagaatacttgtaaggggcaattctccagtattcaactacaacaagaccactaaaag actcacagttctcggaaaggatgctggccctttaactgaagacccagatgaaggcacagctggagttgagtccgcag ttctgagaggattcctcattctgggcaaagaagacaggagatatggaccagcattaagcataaatgaactgagcaac cttgcgaaaggagaaaaagccaacgtactcatcggacaggggggatgtagtattagtgatgaagcgaaagcgaaactc gagtatcctcacagatagtcaaactgccacgaagaggatccgaatggcgatcaacggtagtggcgcaactaatttct ccctccttaagcaagccggcgatgtagaagagaacccaggcccaATGGTCTTCACACTCGAAGATTTCGTTGGGGAC

TGGCGACAGACAGCCGGCTACAACCTGGACCAAGTCCTTGAACAGGGAGGTGTGTCCAGTTTGTTTCAGAATCTCGG

GGTGTCCGTAACTCCGATCCAAAGGATTGTCCTGAGCGGTGAAAATGGGCTGAAGATCGACATCCATGTCATCATCC

CGTATGAAGGTCTGAGCGGCGACCAAATGGGCCAGATCGAAAAAATTTTTAAGGTGGTGTACCCTGTGGATGATCAT

CACTTTAAGGTGATCCTGCACTATGGCACACTGGTAATCGACGGGGTTACGCCGAACATGATCGACTATTTCGGACG

GCCGTATGAAGGCATCGCCGTGTTCGACGGCAAAAAGATCACTGTAACAGGGACCCTGTGGAACGGCAACAAAATTA

TCGACGAGCGCCTGATCAACCCCGACGGCTCCCTGCTGTTCCGAGTAACCATCAACGGAGTGACCGGCTGGCGGCTG

TGCGAACGCATTCTGGCGaaagacgagttaTAAgagaaggctaatgtgctaattgggcaaggagacgtggtgttggt aatgaaacggaaacggaactctagcatacttactgacagccagacagcgaccaaaagaattcggatggccatcaatt agtgtcgaatagtttaaaaacgaccttgtttctacttgcaagccttacaactattgcttgaagtggagcaagagata agaactttctcgtttcagcttatttaataataaaaaacacccttgtttctactaataacccggcggcccaaaatgcc gactcggagcgaaagatatacctcccccggggccggaggtcgcgtcaccgaccacgccgccggcccaggcgacgcg cgacacggacacctgtccccaaaaacgccaccatcgcagccacacacggagcgcccggggccctctggtcaacccca ggac.

In some embodiments, the infectious influenza virus particle and the infectious RSV virion have comparable growth kinetics. The method can therefore further comprise contacting the culture with a substrate for the second luciferase and assaying the culture for bioluminescence. In these embodiments, a decrease in bioluminescence from the second luciferase activity is an indication that the candidate agent is an effective antiviral agent for influenza. Moreover, a decrease in bioluminescence from both the first luciferase activity and second luciferase activity is an indication that the candidate agent is an effective pan-antiviral agent.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) used.

Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from purveyors of chemical libraries including but not limited to ChemBridge Corporation (16981 Via Tazon, Suite G, San Diego, Calif., 92127, USA, www.chembridge.com); ChemDiv (6605 Nancy Ridge Drive, San Diego, Calif. 92121, USA); Life Chemicals (1103 Orange Center Road, Orange, Conn. 06477); Maybridge (Trevillett, Tintagel, Cornwall PL34 0HW, UK)

Alternatively, libraries of natural compounds in the form of bacterial, fungal, plant, and animal extracts are commercially available from a number of sources, including O2H, (Cambridge, UK), MerLion Pharmaceuticals Pte Ltd (Singapore Science Park II, Singapore 117528) and Galapagos NV (Generaal De Wittelaan L11 A3, B-2800 Mechelen, Belgium).

In addition, natural and synthetically produced libraries are produced, if desired, according to methods known in the art, e.g., by standard extraction and fractionation methods or by standard synthetic methods in combination with solid phase organic synthesis, micro-wave synthesis and other rapid throughput methods known in the art to be amenable to making large numbers of compounds for screening purposes. Furthermore, if desired, any library or compound, including sample format and dissolution is readily modified and adjusted using standard chemical, physical, or biochemical methods.

When a crude extract is found to have a desired activity, further fractionation of the positive lead extract is necessary to isolate chemical constituents responsible for the observed effect. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic value may be subsequently analyzed using in vitro cell based models and animal models for diseases or conditions, such as those disclosed herein.

Candidate agents encompass numerous chemical classes, but are most often organic molecules, e.g., small organic compounds having a molecular weight of more than 100 and less than about 2,500 Daltons. Candidate agents can include functional groups necessary for structural interaction with proteins, particularly hydrogen bonding, and typically include at least an amine, carbonyl, hydroxyl or carboxyl group, for example, at least two of the functional chemical groups. The candidate agents often contain cyclical carbon or heterocyclic structures and/or aromatic or polyaromatic structures substituted with one or more of the above functional groups.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Pan-Resistance Mechanism of Respiratory Syncytial Virus Against Structurally Diverse Entry Inhibitors Materials and Methods Cell Culture, Transfection and Virus Stocks.

All cell lines were maintained in Dulbecco's modified Eagle's medium supplemented with 7.5% fetal bovine serum at 37° C. and 5% $CO_2$. Baby hamster kidney (BHK21) cells stably expressing T7 polymerase (BSR-T7/5 cells) were incubated at every third passage in the presence of 500 mg/ml G-418 (Geneticin). Cell transfections were carried out using Lipofectamine 2000 (Invitrogen) or GeneJuice reagent (EMD Millipore). Standard RSV virus stocks were prepared by infecting HEp-2 cells (ATCC HB-8065) at a multiplicity of infection (MOI) of 0.01 pfu/cell at 37° C., followed by incubation at 32° C. for 7-9 days. Cell-associated progeny virus was released through one freeze/thaw cycle and titers determined by $TCID_{50}$ titration or immunoplaque assay as described (Radecke F, et al. (1995) EMBO J 14(23):5773-5784). RecRSV-ren stocks were purified through ultracentrifugation through a 20%/60% one-step sucrose gradient (90 min at 100,000×g, 4° C.). The virus-containing fraction was diluted in TNE buffer (1 mM Tris, pH 7.2, 100 mM NaCl, 10 mM EDTA), pelleted at 60,000×g for 30 min at 4° C., and resuspended in TNE buffer.

Generation and Recovery of Recombinant RSV.

Point mutations were introduced through directed mutagenesis into a shuttle vector containing the RSV L19-F open reading frame, followed by transfer of the modified SacII/SalI line19 F fragment into pSynkRSV A2-L19F-renilla or pSynkRSV A2-L19F-mKate2 (Hotard A L, et al. (2012) Virology 434(1):129-136). Recombinants were recovered as previously described (Hotard A L, et al. (2012) Virology 434(1):129-136) and subjected to RT-PCR and cDNA sequencing for confirmation of specific point mutations.

Compounds.

All compounds were dissolved in dimethyl sulfoxide (DMSO) and stored at −80° C. Sourced compounds were obtained from Ambienter (previously described pan-myxovirus inhibitor 09167 (Moore T W, et al. (2013) ACS Med Chem Lett 4(8):762-767)) and Vitas-M Laboratory or MolPort (GPAR-3710 stocks). The screening library was obtained from ChemDiv. For screening, $2 \times 10^4$ (96-well plate format) or $6 \times 10^3$ (384-well plate format) HEp-2 cells/well were seeded into solid-wall microtiter plates. Test articles dissolved in DMSO were added at 5 µM final concentration (final DMSO content was below 0.1% vol/vol). As internal reference, four wells each on each plate were treated with the pan-myxovirus inhibitor JMN3-003 (final concentration 1 µM) or vehicle (DMSO) only. Cells were infected with recRSV A2-L19F-ren (MOI=0.2 pfu/cell) and renilla luciferase activities quantified in a Synergy H1 (BioTek) multimode microplate reader after 44-48-hour incubation.

HTS Data Analysis.

Raw data sets were automatically reformatted and imported into the cellHTS2 application package (Boutros M, et al. (2006) Genome Biol 7(7):R66; Pelz O, et al. (2010) BMC Bioinformatics 11:185). Data were analyzed according to the plate median method; each value was normalized to the median value for all compound wells of the plate, and normalized values were scaled to the median absolute deviation of the plate. The SciFinder database package (American Chemical Society) was used to query chemical databases with hit candidate structures to evaluate known bioactivities of analogs, commercial availability, and free intellectual property (IP) space.

Dose-Response Curves, Efficacy and Cytotoxicity.

Cells infected (MOI=0.05 pfu/cell) with recRSV A2-L19F, recRSV A2-L19F-ren, recRSV A2-L19F-mKate2, or GPAR-3710-resistant variants thereof were incubated in the presence of serial dilutions of compound for 44 hours, followed by titration of cell-associated progeny particles or quantification of reporter expression as specified. If possible, fifty or ninety percent effective concentrations ($EC_{50}$ or $EC_{90}$ values, respectively) were calculated based on four-parameter variable-slope nonlinear regression modeling of mean values of at least three experiments. To quantify the effect of compound on cell metabolic activity, cells were incubated in the presence of serial compound dilutions (30 µM highest) for 44-hours, then subjected to a nonradioactive cytotoxicity assay (CytoTox 96; Promega) according to the manufacturer's instructions. Assay values were normalized to vehicle (DMSO) controls according to % toxicity=100−100×(sample−reference)/(vehicle−reference).

Time-of-Addition Assays.

HEp-2 cells were spin-inoculated (1,000×g; 30 minutes; 4° C.; MOI=10 pfu/ml) with purified recRSV A2-L19F-ren. Compound was added at the specified times pre- or post-infection, and luciferase activities determined 26 hours post-infection. Reference samples received volume equivalents of vehicle (DMSO).

Minireplicon Reporter Assay.

Based on a previously described pT7-RSV-luciferase minigenome reporter (Dochow M, et al. (2012) J Biol Chem 287(9):6878-6891), an RSV minigenome construct was generated under the control of the constitutive RNA pol I promoter (pHH-RSV-repl-firefly). Huh-7 cells were co-transfected with this plasmid and plasmids pRSV-L, pRSV-M2-1, pRSV-N and pRSV-P, respectively, under CMV promoter control. Compounds GPAR-3710 or JMN3-003 were added in serial dilutions, luciferase reporter activities determined 40 hours post-transfection, and $EC_{50}$ concentrations calculated as above if possible.

End-Point Cell-to-Cell Fusion Assay.

A dual split-protein cell content mixing assay was employed to quantify the extent of cell-to-cell fusion mediated by RSV F. 293T cells were transfected with plasmid DNA encoding eGFP-renilla luciferase dual-split fusion proteins $DSP_{1-7}$ or $DSP_{8-11}$ (Kondo N, et al. (2011) Curr Protoc Cell Biol Chapter 26:Unit 26 29), respectively. One cell population received in addition plasmid DNA encoding RSV L19F or, for control, MeV F and H proteins (Brindley M A, et al. (2012) Proc Natl Acad Sci USA 109(44):E3018-3027). Cell populations were mixed at equal ratio four hours post-transfection and incubated in the presence of the specified amounts of GPAR-3710 for 26 hours. The activity of the reconstituted luciferase was quantified after loading of cells with 10 µM ViviRen (Promega) for 30 minutes.

Virus Entry Kinetics Assay.

293T cells transfected with the plasmids encoding the $DSP_{1-7}$ or $DSP_{8-11}$ (Kondo N, et al. (2011) Curr Protoc Cell Biol Chapter 26:Unit 26 29), respectively, were mixed at equal ratio, pre-loaded with EnduRen life cell substrate as described (Brindley M A, et al. (2013) J Virol 87(21):11693-11703), and spin-inoculated with recRSV A2-L19F (1,000× g; 30 minutes; 4° C.; MOI=6 pfu/cell) in the presence of GPAR-3710 or DMSO. Activity of reconstituted luciferase was recorded at the specified time points.

Kinetic Cell-to-Cell Fusion Assay.

293T cells were transfected with the DSP 1-7 or $DSP_{8-11}$ expression plasmids, transfected cells detached and reseeded at equal ratio. Cells were then transfected with standard or mutant RSV L19-F-encoding plasmids, loaded with EnduRen luciferase substrate as above and incubated at 32° C. or 37° C. Luciferase activity was recorded at the specified time points.

Microscopy.

Fluorescence microphotographs were taken on a Zeiss Axio Observer D.1 inverted microscope at a magnification of ×200. For phase-contrast microphotographs, a Nikon Diaphot 200 inverted microscope was used at a magnification of ×200.

Virus Adaptation.

HEp-2 cells were infected with recRSV A2-L19F-mKate2 at an MOI of 0.1 pfu/cell and incubated in the presence 0.1 µM GPAR-3710. When extensive red fluorescence emerged, fresh cell monolayers were re-infected with 10-fold diluted cell-associated virions in the presence of increasing compound concentrations. Total RNA was extracted (RNeasy purification kit; Qiagen) from individually adapted clones when GPAR-3710 concentrations of 30 µM were tolerated, cDNAs generated using random hexamer primers, the F-encoding open reading frame amplified and subjected to DNA sequencing. Candidate mutations were rebuilt in RSV-L19F expression plasmids and subjected to cell-to-cell fusion assays in the presence of the compound. Selected confirmed mutations were rebuilt in the pSynkRSV A2-L19F-mKate2 plasmid background and the corresponding recombinants recovered.

Surface Biotinylation, SDS-PAGE, and Immunoblotting.

Protein surface expression was determined as described before (Plemper R K, et al. (2003) J Virol 77(7):4181-4190) with the following modifications. 293T cells ($8 \times 10^5$ per well in a 6-well plate format) were transfected with 2 µg of plasmid DNA encoding the specified RSV F construct. Washed cells were biotinylated with 0.5 mg/ml sulfosuccinimidyl-2-(biotinamido)ethyl-1,3-dithiopropionate (Pierce), quenched, and subjected to precipitation using immobilized streptavidin (GE Healthcare) after lysis in RIPA buffer (1% sodium deoxycholate, 1% NP-40, 150 mM NaCl, 50 mM Tris-Cl (pH 7.2), 10 mM EDTA, 50 mM sodiumfluoride and protease inhibitors). Washed precipitates were fractioned by SDS-PAGE, blotted onto polyvinylidene difluoride (PVDF) membranes (GE Healthcare), and F protein material immunostained using the motavizumab monoclonal antibody Immunoblots were developed using a ChemiDoc digital imaging system (Bio-Rad), and subjected to densitometry quantification using the Image Lab software package (Bio-Rad).

Fusion Core Assay.

Standard and mutant recRSV A2-L19F were grown at 32° C. Cell associated viral particles were harvested, purified by ultracentrifugation through a 20%/60% one-step sucrose gradient, and subjected to cold extraction of native plasma membrane proteins using Native Sample Buffer (100 mM Tris-Cl (pH 8.6), 10% glycerol, 0.0025% Bromophenol Blue, 0.1% digitonin, 25 mM iodoacetamide), and clearance centrifugation (20,000×g; 15 minutes; 4° C.). Extracts were mixed with Laemmli sample buffer with 0.5% SDS and fractionated on 3-8% wt/vol NuPAGE Tris-Acetate gradient gels (Life Technologies), followed by immunoblotting as above.

Temperature Sensitivity Assay.

Standard and resistant recRSV A2-L19F strains as specified were divided into equal aliquots, aliquots either frozen at −80° C. or incubated at the indicated temperature for 24 hours followed by freezing, and remaining virus titers determined by $TCID_{50}$ titration.

In vivo infection. BALB/cJ mice (Jackson Laboratories) were anesthetized by intramuscular injection of a ketamine-xylazine solution and infected intranasally with $1\times10^5$ pfu of recRSV A2-L19F, recRSV A2-L19F$_{D401E}$, or recRSV A2-L19F$_{D489E}$, respectively. All animal procedures were performed according to the guidelines of the Emory University Institutional Animal Care and Use Committee.

Lung Titers.

Mice were euthanized day 4 p.i., the left lung lobe extracted, weighed, and homogenized using a BeadBeater (Biospec Products). Homogenates were serially diluted, transferred to HEp-2 cells, and cells overlaid one hour p.i. with minimum essential medium (MEM) containing 10% FBS, penicillin G, streptomycin sulfate, amphotericin B solution, and 0.75% methylcellulose. Six days p.i., cells were fixed with methanol and plaques visualized by immunodetection as described (Stokes K L, et al. (2011) J Virol 85(12):5782-5793; Lee S, et al. (2012) J Virol 86(23): 13016-13024).

Mucin Expression.

Mice were euthanized with fatal-plus eight days p.i. (Stokes K L, et al. (2011) J Virol 85(12):5782-5793; Lee S, et al. (2012) J Virol 86(23):13016-13024), heart-lung tissue was harvested and fixed in 10% formalin. Lung tissue sections embedded in paraffin blocks were stained with periodic acid-Schiff (PAS) stain to visualize mucin expression. PAS-stained slides were digitally scanned using a Zeiss Mirax Midi microscope (Carl Zeiss Microimaging).

Statistical Analysis.

To determine active concentrations from dose-response curves, four parameter variable slope regression modeling was performed using the Prism (GraphPad) software package. Results were expressed as 50% or 90% inhibitory concentrations with 95% asymmetrical confidence intervals. Statistical significance of differences between sample groups were assessed by one-way or two-way analysis of variance (ANOVA) in combination with Bonferroni multiple comparison post-tests as specified in the figure legends. Experimental uncertainties are identified by error bars, representing standard deviation (SD) or standard error of the mean (SEM), as specified.

Results

Figure 1A:
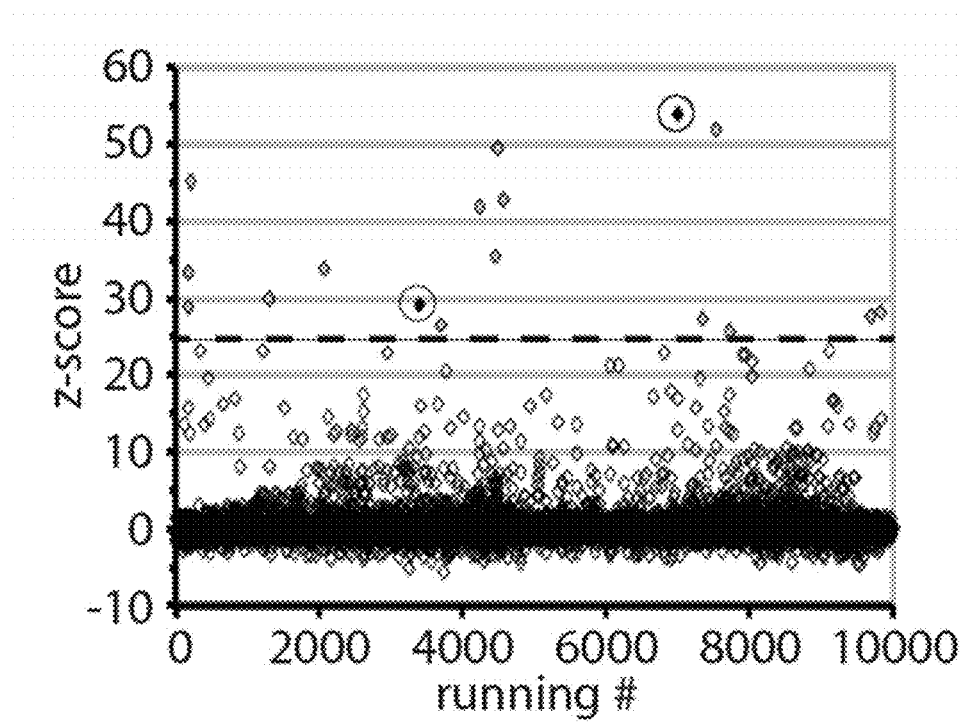
FIGS. 1A to 1C illustrate identification of a new small-molecule class of RSV inhibitors.

To identify anti-RSV drug candidates, a 10,000-entry small-molecule diversity set was screened against a recombinant (rec) RSV strain harboring an additional transcription unit encoding for renilla luciferase (Hotard A L, et al. (2012) Virology 434(1):129-136; Yan D, et al. (2013) J Virol 87(20):11076-11087). Applying recently established assay conditions for automated anti-paramyxovirus drug screens (Yan D, et al. (2013) J Virol 87(20):11076-11087), this exercise returned a hit candidate pool of 17 compounds, each with a primary screening score exceeding 10 assay-SD (FIG. 1A).

Figure 1B:
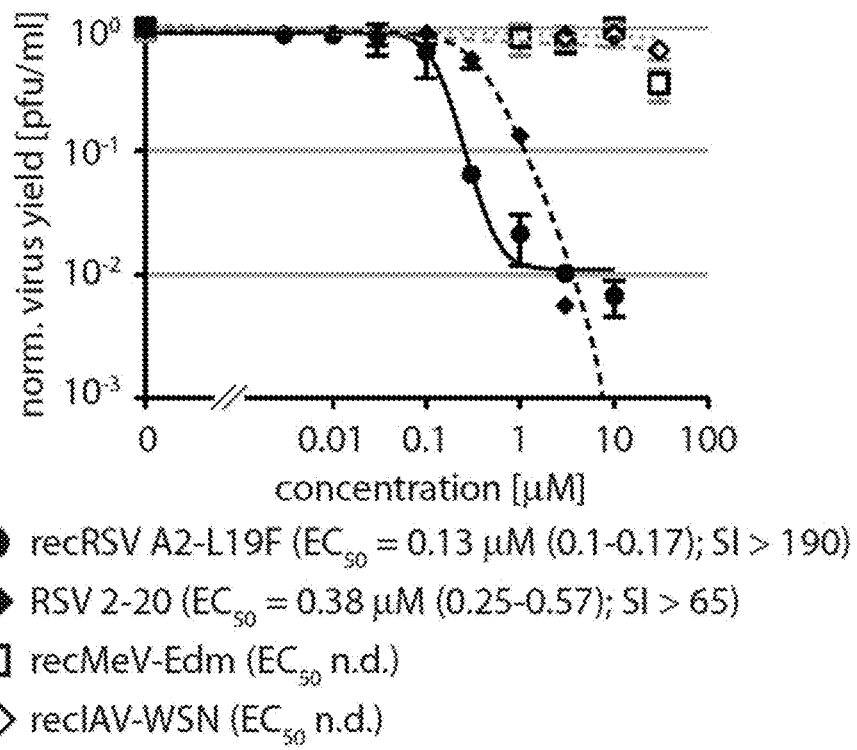
Figure 1C:
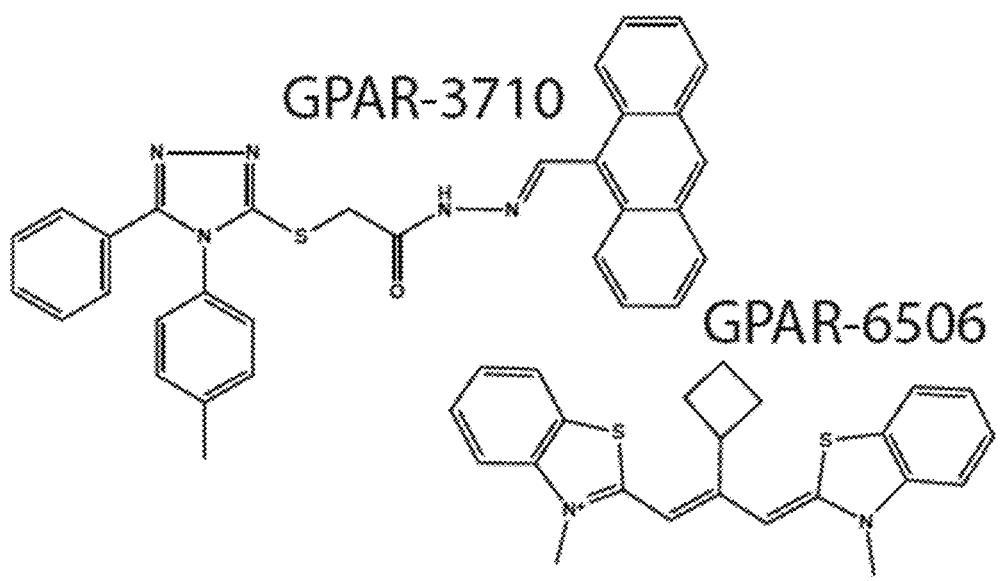
Figures 6C, 6D, 7:
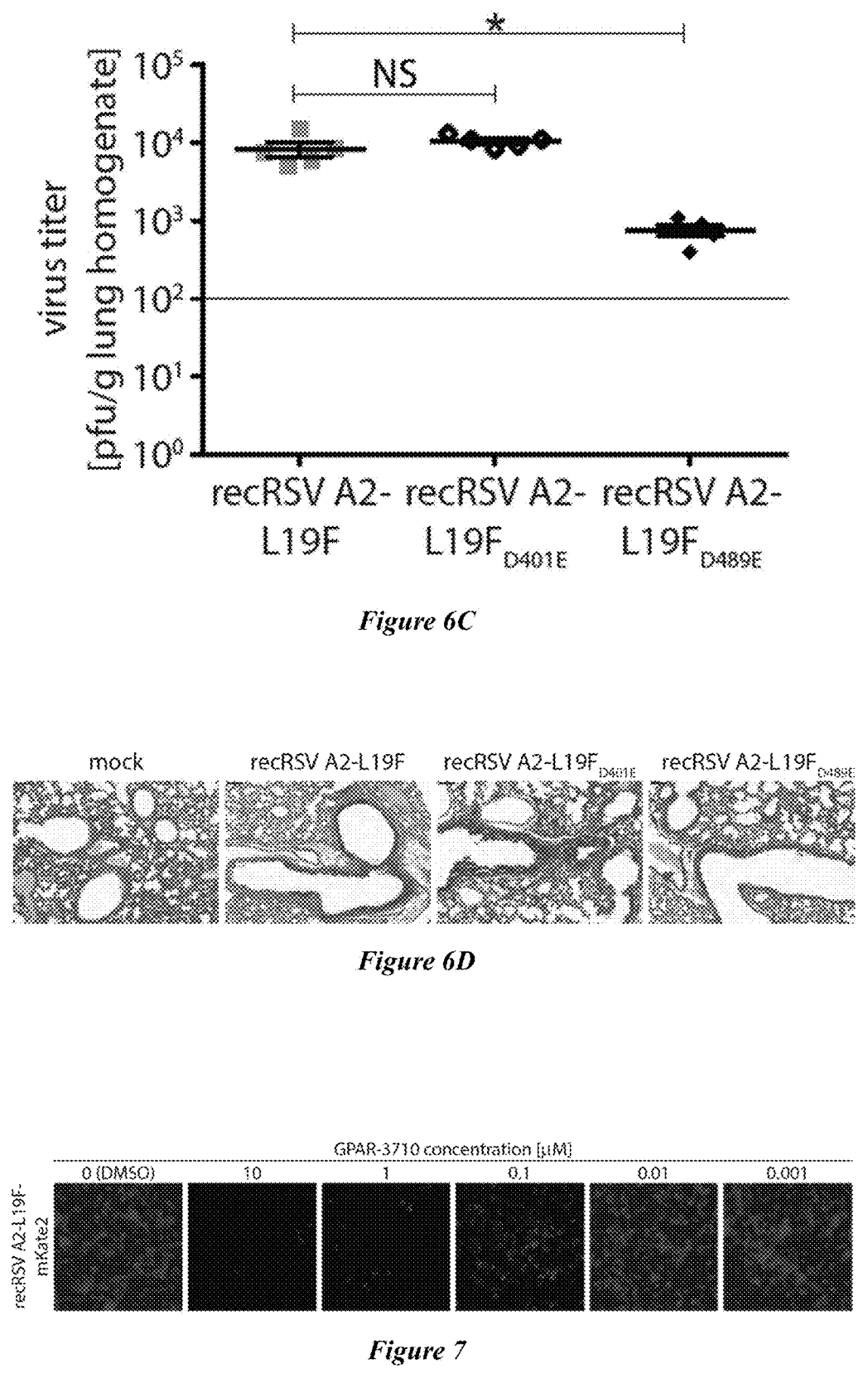

Two-concentration counter-screens and cytotoxicity testing yielded 2 candidates that showed >90% RSV inhibition at a tenth (0.5 µM) of the original screening concentration (FIG. 1B). Based on structural considerations and cytotoxicity profiles, of these GPAR-3710 was sourced for structure-integrity verification. The sourced compound combined low cytotoxicity with target-specific and dose-dependent inhibition of different RSV strains with active concentrations in the nano- to low micromolar range (FIG. 1C and FIG. 7).

Chemical Class of Small-Molecule RSV Entry Inhibitors

Figure 2A:
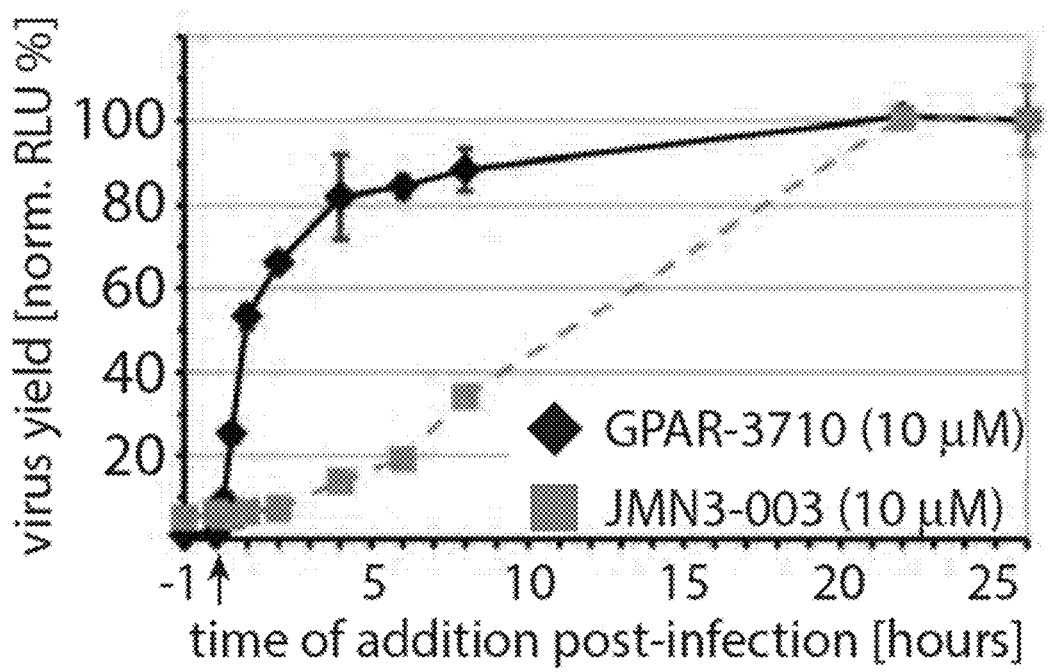
Figure 2B:
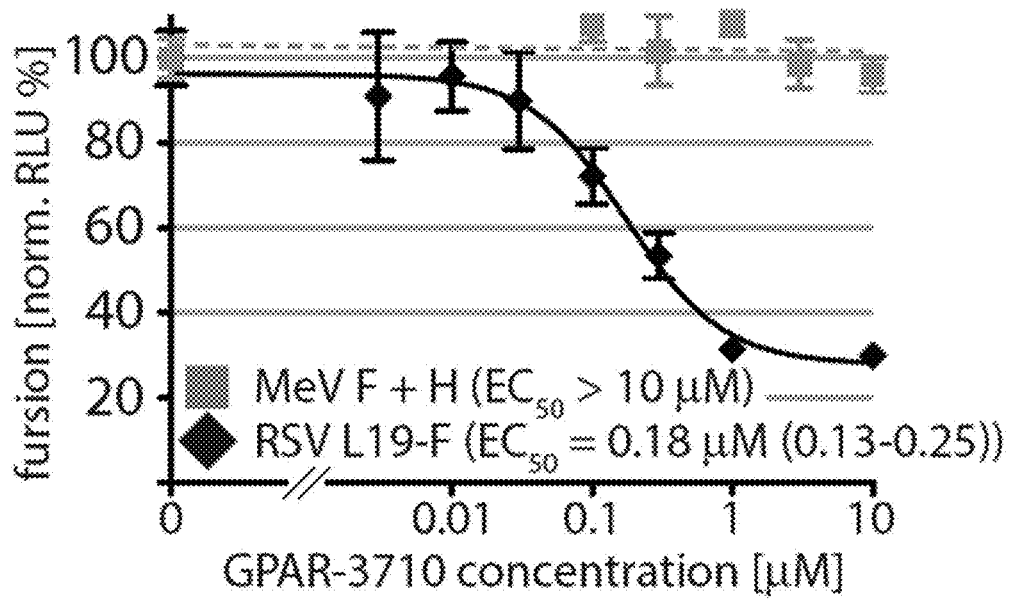
Figure 2C:
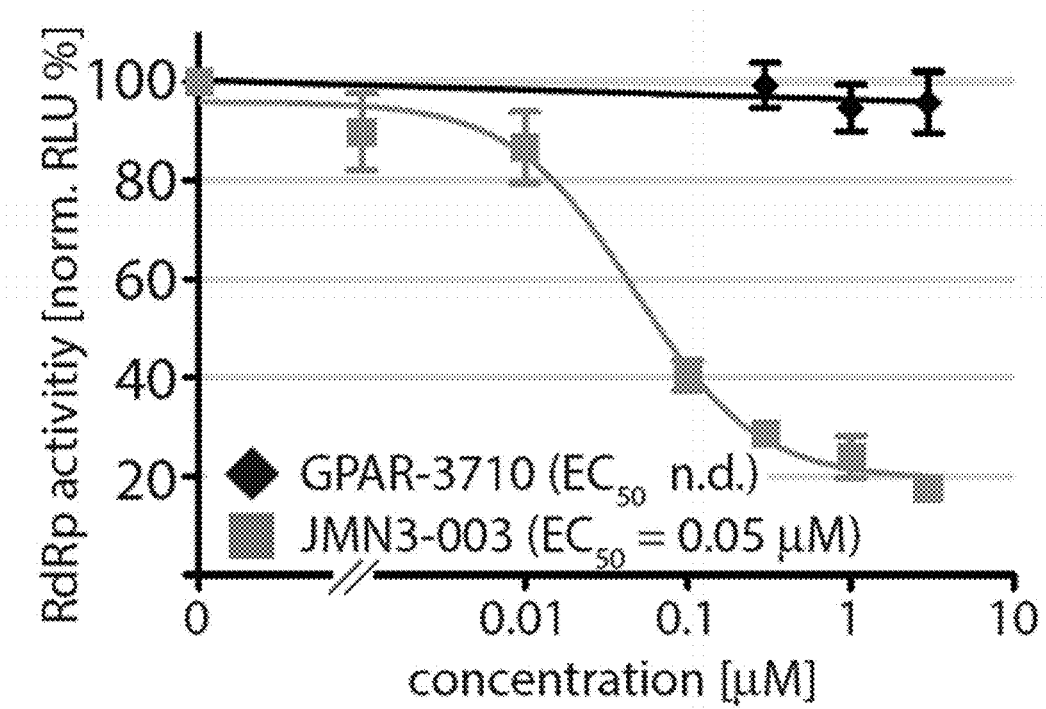
Figures 2D, 3A:
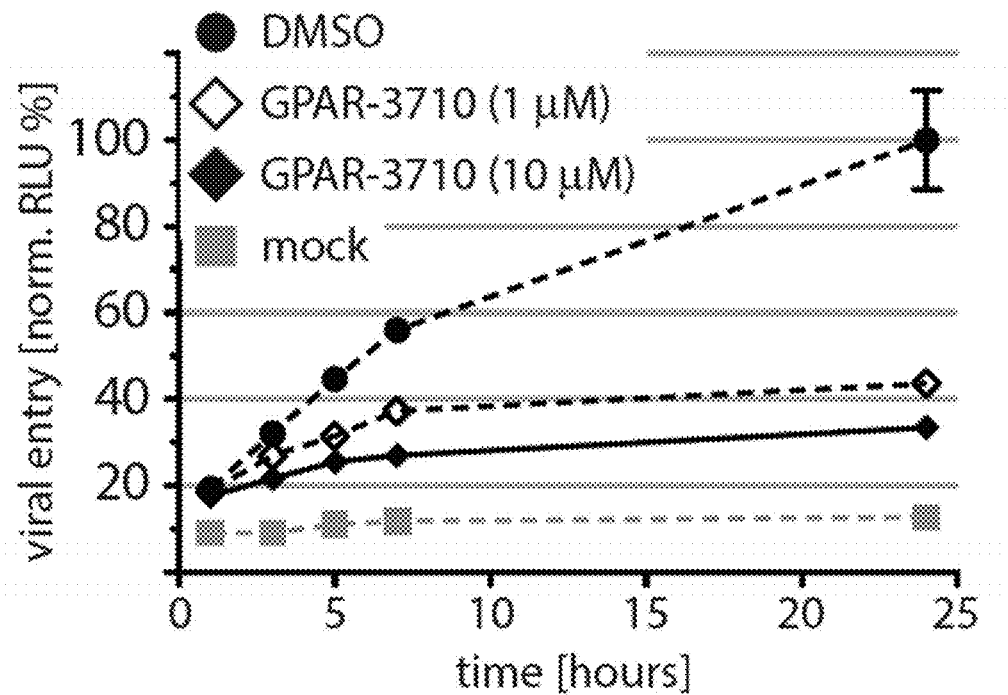

For mechanistic characterization, GPAR-3710 was first subjected to a time-of-compound addition study to narrow the step in the viral life cycle blocked by the article. Maximal inhibition of virus replication was observed only when the compound was added at the time of infection, while essentially all antiviral activity was lost when GPAR-3710 was administered later than four hours post-infection (FIG. 2A). By comparison, a pan-inhibitor of myxovirus polymerase function, JMN3-003 (Krumm S A, et al. (2011) PLoS One 6(5):e20069), remained potently inhibitory even when added eight hours post-infection. This time-of-addition profile points towards inhibition of virus attachment or cell entry by the compound. For cross-examination, GPAR-3710 was tested in two plasmid-based reporter assays that specifically measure bioactivity of the viral entry (Brindley M A, et al. (2012) Proc Natl Acad Sci USA 109(44):E3018-3027) and polymerase (Dochow M, et al. (2012) J Biol Chem 287(9):6878-6891) machinery, respectively. RSV F protein-mediated membrane fusion activity was specifically and potently inhibited by the compound in these assays (FIG. 2B), while activity of the viral RNA-dependent RNA-polymerase (RdRp) complex remained unaffected (FIG. 2C). To directly monitor the effect of the inhibitor on the rate of viral entry, a quantitative RSV entry assay was established that monitors virus-to-cell fusion in near real-time (FIG. 2D). RSV particles were spin-inoculated on a monolayer of cells expressing either the amino- or carboxy-terminal halves of an eGFP-renilla luciferase chimeric protein (Kondo N, et al. (2011) Curr Protoc Cell Biol Chapter 26:Unit 26 29). Simultaneous fusion of the incoming viral particles with two adjacent target cells results in cell content mixing, restoring eGFP fluorescence and renilla luciferase activity. When executed in the presence of increasing GPAR-3710 concentrations, this assay revealed a significant, dose-dependent reduction of the RSV entry rate by the compound (FIG. 2D). Taken together, these observations characterize the GPAR-3710 scaffold as a novel class of small-molecule RSV entry inhibitors.

Escape Mutations Locate to the RSV F Protein

Figure 8:
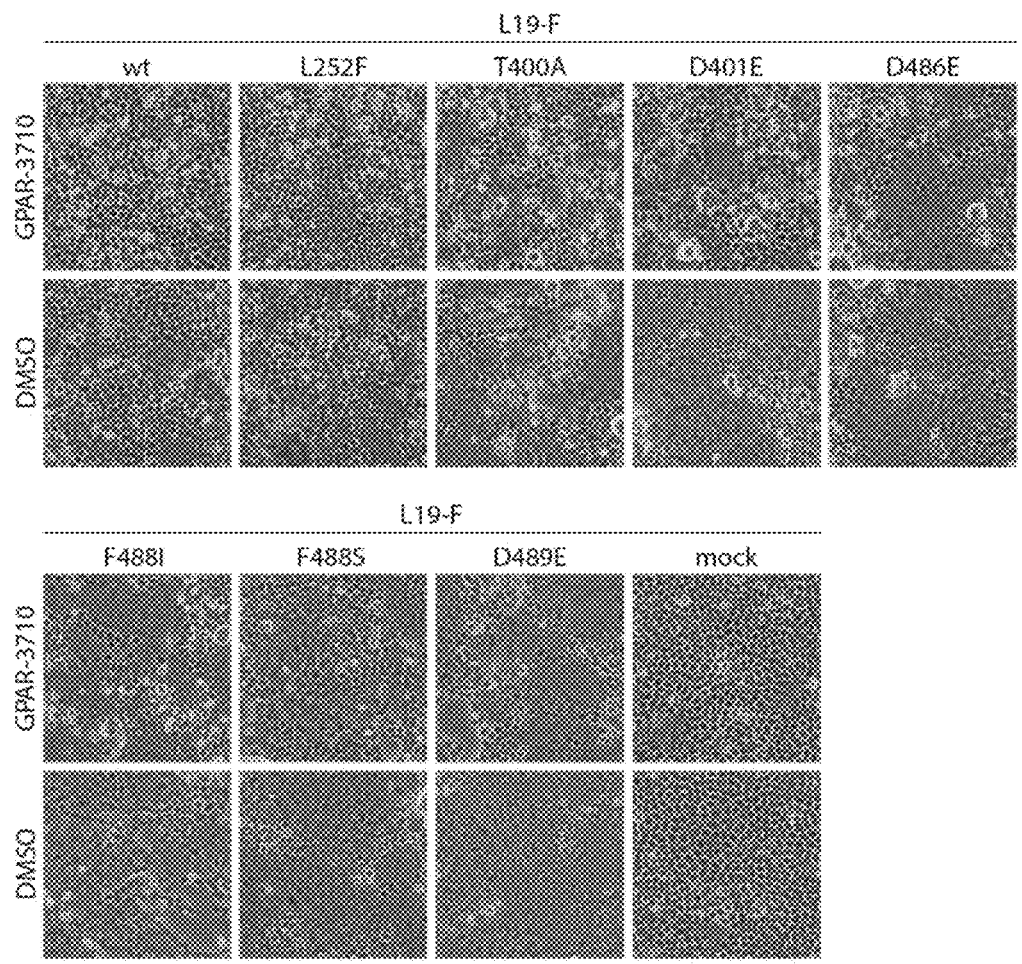
FIG. 8 shows resistance testing of RSV F mutants harboring individual escape mutation candidates. Cells were transfected with expression plasmids encoding the specified L19-F mutants, and incubated in the presence of 10 µM GPAR-3710 or vehicle (DMSO). Microphotographs were taken 44 hours p.i. Mock denotes cells that received vector DNA instead of F expression plasmid.

As a hallmark for pathogen-directed antiviral compounds, the experimental induction of viral escape from inhibition is typically straightforward, and resistance mutations usually locate to the viral protein physically targeted by the compound. RSV escape from GPAR-3710 inhibition was provoked through gradual adaptation to growth in the presence of increasing compound concentrations. Robust resistance—defined by viral growth in the presence of 30 µM (>200×$EC_{50}$ concentration) of the compound—reliably appeared within a 30-day adaptation period. Efforts were concentrated on the viral entry machinery in search for the molecular basis for escape and determined the F protein sequences of six independently adapted RSV strains. Candidate mutations were rebuilt in an expression plasmid encoding the RSV line19 (L19) F protein (Moore M L, et al. (2009) J Virol 83(9):4185-4194) through directed mutagenesis, followed by first-pass resistance testing in transient cell-to-cell fusion assays carried out in the presence of the compound (FIG. 8).

Figures 3B, 3C:
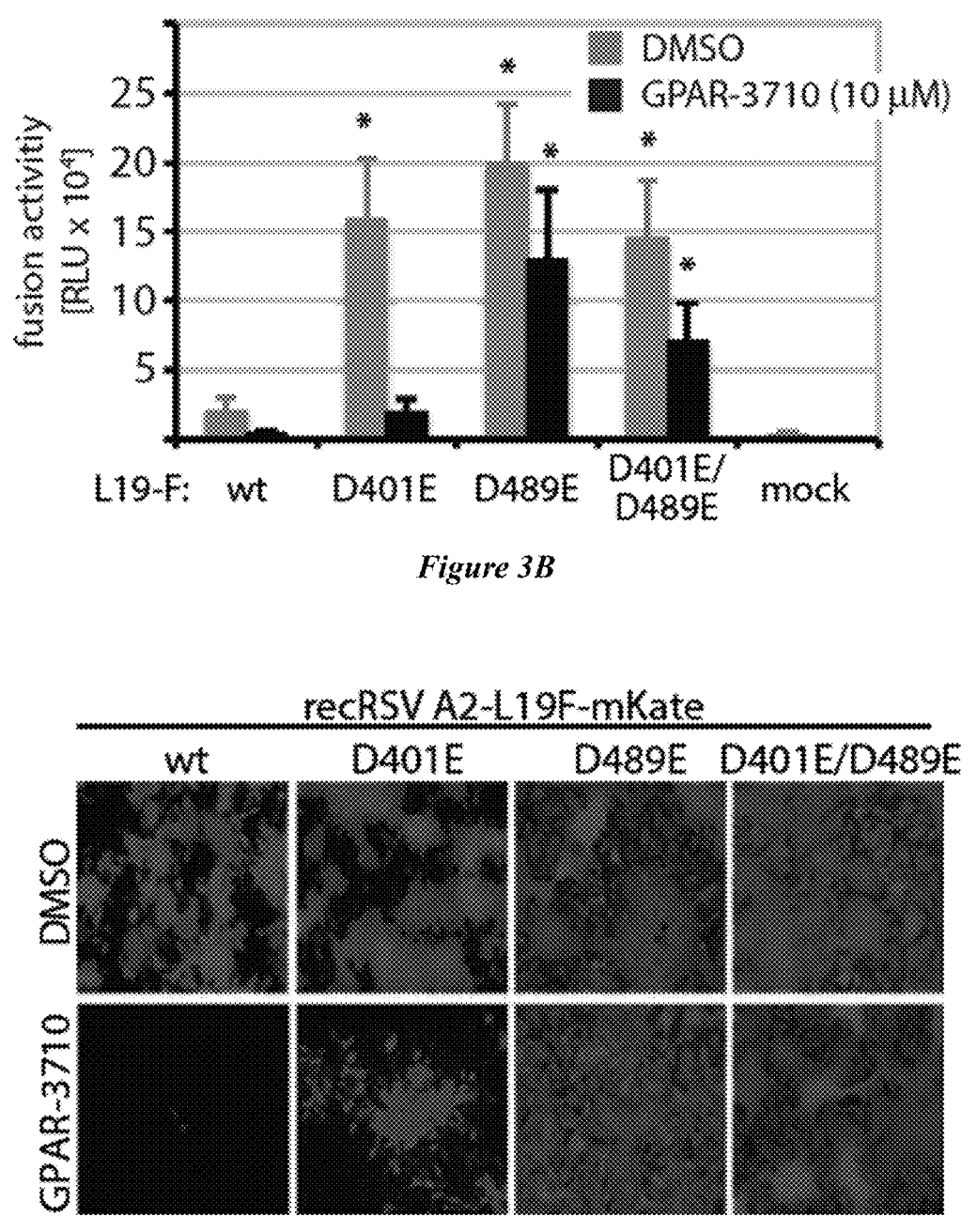

In each of the six strains, a single point mutation was identified in the F protein that contributed to the phenotype (FIG. 3A). The mutations clustered in two linear microdomains (400 and 489) of RSV F, spanning residues 400-401 and 486-489, respectively. Mutations D401E and D489E were selected for transient cell-to-cell fusion assays in the presence and absence of compound. In addition, an $F_{D401E/D489E}$-double mutant construct was generated and analyzed. All mutant F were hyperfusogenic compared to the standard L19-F protein (FIG. 3B). Particularly robust resistance was observed when the D489E mutation was present.

Figure 3D:
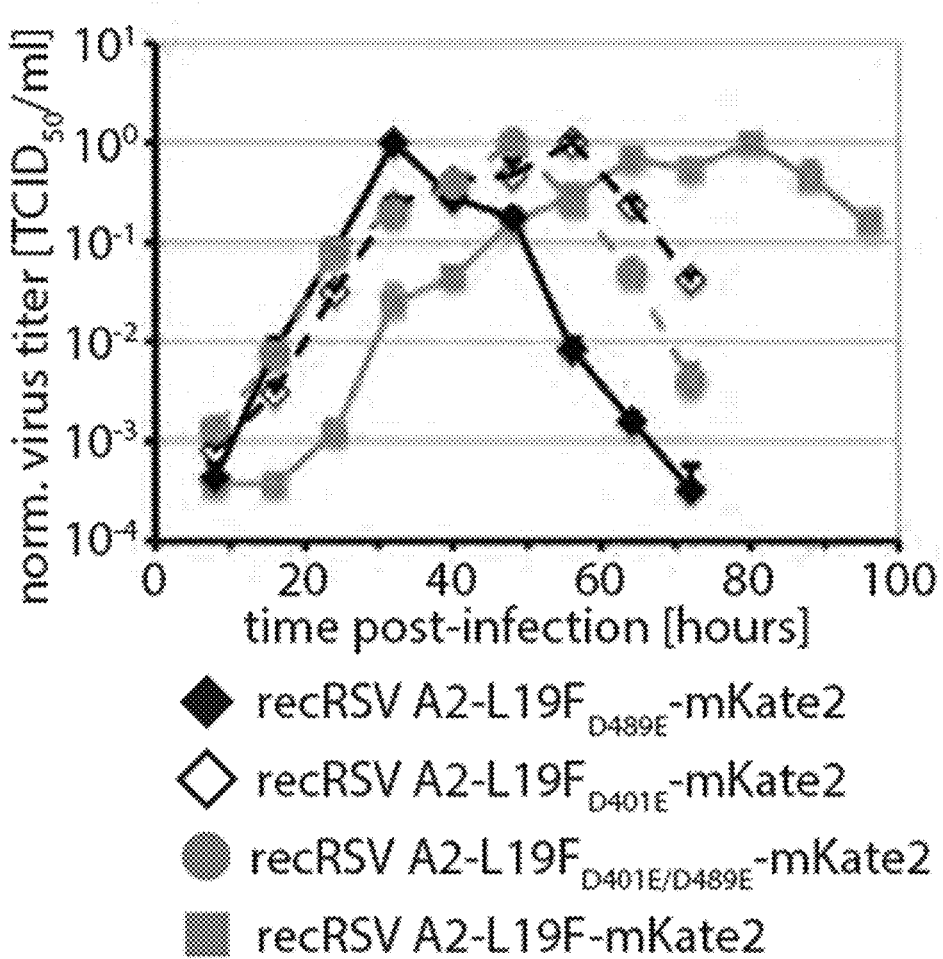

To verify the role in escape in the context of viral infection, the mutant F constructs was transferred into the genetically-controlled cDNA background of a recombinant RSV A2, harboring the L19-F protein (Hotard A L, et al. (2012) Virology 434(1):129-136). In addition, a cDNA construct containing the $F_{D401E/D489E}$ double-mutant was generated in the place of parental L19-F. All three mutant recRSVs were recovered successfully and showed resistance to GPAR-3710, based on efficient spread through cell monolayers in the presence of the compound (FIG. 3C). They all also showed accelerated growth rates compared to standard recRSV A2-L19F (FIG. 3D).

Structural Basis for Pan-Resistance Against Diverse RSV F Inhibitors

Figure 4A:
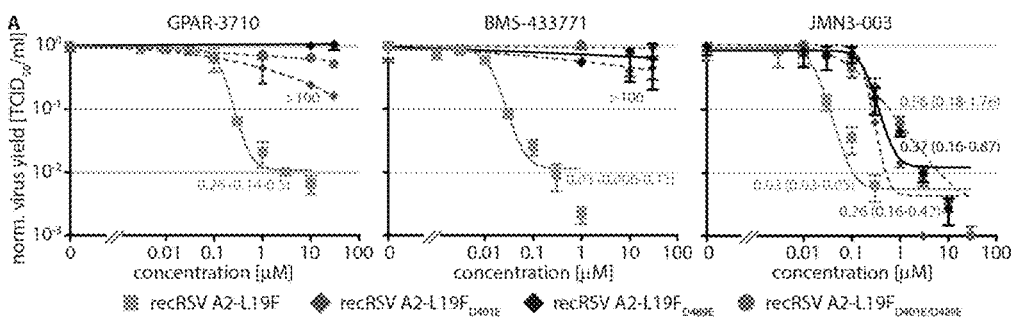

Previous anti-RSV drug discovery campaigns have yielded several structurally distinct, highly potent, small-molecule entry inhibitor classes that reportedly likewise induced escape mutations in the F 400 and/or 480 microdomains (Table 1). Lead analogs of several of these inhibitor classes are currently at different stages of pre-clinical and clinical development. To quantify viral resistance, dose-response curves were generated for GPAR-3710 and BMS-433771, a clinically advanced RSV entry inhibitor, against the three RSV recombinants. Mutations in either microdomain resulted in over 30-fold increased $EC_{90}$ concentrations for either compound (FIG. 4A), confirming robust resistance.

Based on a biochemical target analysis, it was proposed that BMS-433771 populates a hydrophobic pocket in the HR-A triple helix that contains residue 489, preventing assembly of the 6HB fusion core during F refolding into its postfusion conformation (Cianci C, et al. (2004) Proc Natl Acad Sci USA 101(42):15046-15051). Surprisingly, however, both resistance domains map to opposing ends of the rod-like postfusion F structure, separated by approximately 100 Å from each other (FIG. 4B). Recently, the structure of RSV F was solved also in the metastable prefusion state (McLellan J S, et al. (2013) Science 342(6158):592-598). When the hot-spots were localized in this structure, residues 401 and 489 were found to be positioned in close proximity of each other (<10 Å) at the base of head domain in prefusion F (FIG. 4C).

Resistance Mutations Alter the Rate of F-Mediated Membrane Fusion

Prompted by proximity of both resistance hot-spots in prefusion F and the accelerated growth rates of the RSV recombinants, the question arose whether mutations in either microdomain affect prefusion F refolding rates. Employing the kinetic cell-to-cell fusion assay, the rates of fusion pore formation mediated by the different F mutants were assessed. At physiological temperature, maximal fusion rates of all three F mutants were increased compared to that of standard F (FIGS. 5A and 5B). To fully appreciate the altered refolding kinetics of the mutated F variants, fusion rates were determined under reduced energy conditions (32° C. incubation temperature). Then, none of the individual mutations showed a statistically significant accelerating effect on fusion kinetics. In contrast, the $F_{D401E/D489E}$ double mutation significantly boosted the fusion rate at 32° C., indicating a temperature-sensitive phenotype (FIGS. 5B and 5C).

Figures 5D, 5E:
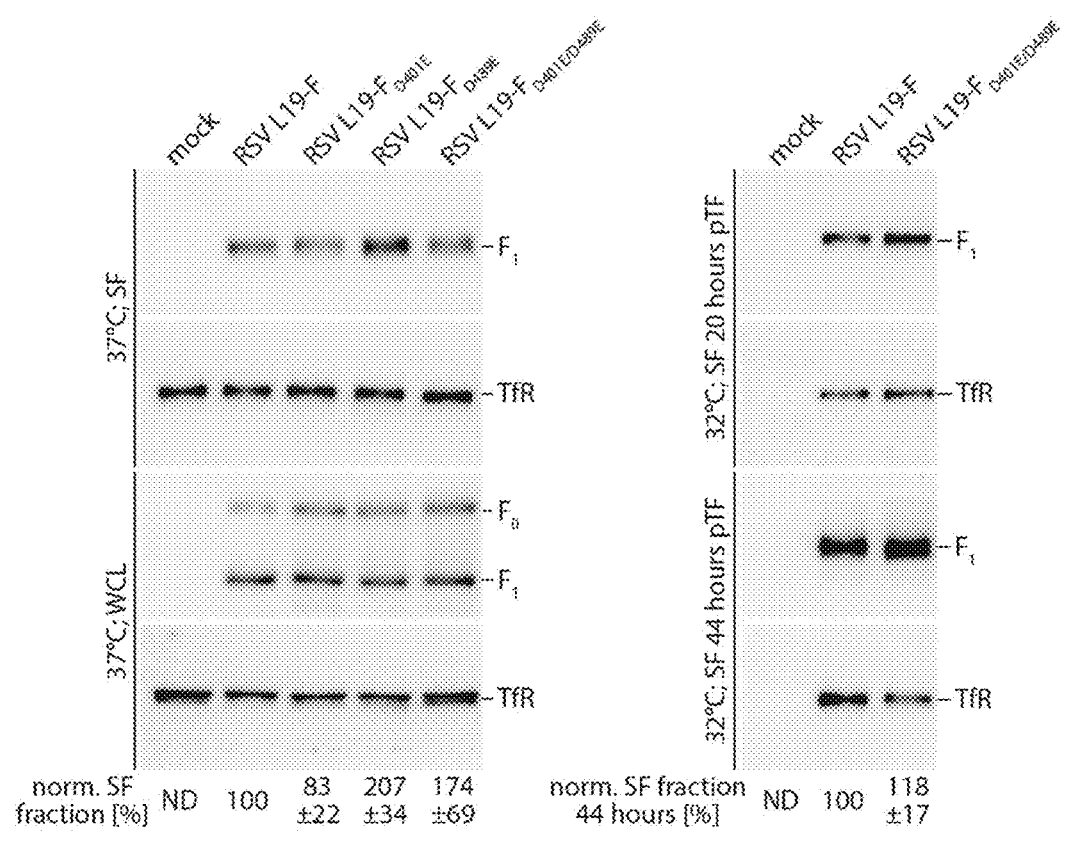

A densitometric analysis of whole cell lysates and cell surface expressed F material and immunoblotting demonstrated enhanced cell surface steady state levels of the $F_{D489E}$ mutant compared to standard RSV L19-F (FIG. 5D). However, levels of the $F_{D401E/D489E}$ double mutant were slightly lower than those of $F_{D489E}$ and intracellular transport rates of the double mutant and standard F remained essentially identical when cells were incubated at 32° C. (FIG. 5E). These results suggest that higher bioactivity of the double mutant does not result from increased surface expression, but indicate a synergistic effect of changes in each resistance hot-spot on F bioactivity.

Effect of Resistance Mutations on Viral Pathogenicity

To test whether a reduced structural stability of the mutated prefusion F constitutes the underlying mechanism for resistance, a fusion-core assay was applied to RSV F that biochemically monitors the formation of the thermodynamically stable 6HB fusion core, which is indicative of F trimer refolding into the postfusion conformation. Intact F trimers were natively extracted from gradient-purified viral particles cells, followed by gel-fractionation under mildly denaturing, non-reducing conditions. Presence of the stable 6HB core in postfusion F complexes should be reflected by predominant migration of the extracted material as homo-trimers, whereas metastable prefusion F trimers should have a higher propensity to disintegrate. When standard F and the three drug resistant mutants were examined in this assay, the mutant trimers predominantly migrated as stable trimers, while standard F was mostly monomeric (FIG. 6A).

These findings spotlight that the resistance mutations reduce the structural stability of prefusion F complexes. To test whether this phenotype is mirrored by increased sensitivity of the recombinant virions to thermal inactivation, virus preparations were subjected to a 24-hour incubation step at different temperatures in the absence of target cells. The individual mutant strains showed an intermediate but significant reduction in titers compared to standard recRSV after incubation at 32° C.-39° C. (recRSV A2-L19$F_{D401E}$) or 39° C. (recRSV A2-L19$F_{D489E}$), respectively (FIG. 6B). Moreover, temperature sensitivity was most pronounced in the case of the recRSV A2-L19$F_{D401E/D489E}$ double mutant, since titers of this strain were significantly lower over the whole temperature range assessed.

Heightened thermo-sensitivity may coincide with lowered viral fitness in vivo, which could render drug-resistant variants clinically insignificant. An established mouse model was employed for RSV infection (Stokes K L, et al. (2011) J Virol 85(12):5782-5793) to assess pathogenicity of the mutant viruses. Only the two recombinants expressing single-mutant F variants that had emerged spontaneously during adaptation were subjected to this study. Lung titers of BALB/cJ mice infected with recRSV A2-L19F$_{D489E}$ were slightly reduced compared to animals exposed to standard recRSV (FIG. 6C). However, viral loads of animals infected with recRSV A2-L19F$_{D401E}$ remained unchanged.

The induction of extensive mucus production is one of the key features associated with RSV pathogenesis (Johnson J E, et al. (2007) Mod Pathol 20(1):108-119) and serves as an indicator for the severity of RSV disease in the mouse model (Moore M L, et al. (2009) J Virol 83(9):4185-4194; Lee S, et al. (2012) J Virol 86(23):13016-13024). When animals were infected with the two mutant recombinants and standard recRSV, the recRSV A2-L9F$_{D489E}$ mutant was only slightly mucogenic compared to mock-infected mice (FIG. 6D). In contrast, the recRSV A2-L19F$_{D401E}$ recombinant showed strong mucus induction at a level at least equivalent to that seen in lungs of animals infected with parental recRSV A2-L19F. Taken together, these results demonstrate that the individual F mutations, which each mediate robust resistance to diverse entry inhibitors, are not mandatorily associated with reduced viral pathogenesis in vivo.

Discussion

As a leading cause for infant hospitalization from viral respiratory disease, RSV has emerged in the past decade as a major target for the development of novel vaccines and therapeutics. While formalin-inactivated RSV vaccines and subunit vaccines based on the G and F viral glycoproteins were associated in several past trials with disease enhancement (Hancock G E, et al. (1996) J Virol 70(11):7783-7791; Murphy B R, et al. (1990) Vaccine 8(5):497-502; Kapikian A Z, et al. (1969) J Epidemiol 89(4):405-421; Kim H W, et al. (1969) Am J Epidemiol 89(4):422-434), live attenuated vaccine candidates tested to date were—although safe in infants—poorly immunogenic, reflected by insufficient neutralizing antibody titers (Collins P L, et al. (2011) Virus Res 162(1-2):80-99). Antiviral therapeutics may ameliorate disease in high-risk pediatric patients and possibly the elderly, especially since viral load in the early phase of clinical disease was found predictive for the severity of disease progression and the risk of life-threatening complications (DeVincenzo J P, et al. (2005) J Infect Dis 191(11):1861-1868; El Saleeby C M, et al. (2011) J Infect Dis 204(7):996-1002).

Large scale screening campaigns to identify novel therapeutic candidates against RSV were compromised thus far by the lack of appropriate reporter strains that were developed for robust automated drug discovery assays. The disclosed study demonstrates the value of the recombinant RSV strain expressing renilla luciferase. Major advantages over conventional RSV-based assays explored for high-throughput campaigns are the broad dynamic range of the luciferase reporter; the availability of a full set of subinfection assays for MOA characterization that are genetically matched to the screening strain; the option to readily assess resistance in genetically controlled viral recombinants using an efficient reverse genetics system; and the high pathogenicity of the reporter strain in the mouse model compared to standard laboratory RSV strains (Stokes K L, et al. (2011) J Virol 85(12):5782-5793), opening a straight-forward path towards small-animal efficacy testing of lead candidates.

By design, the HT assay developed for the disclosed screen has a higher propensity to identify early and intermediate stage inhibitors of the viral life cycle (i.e. inhibitors of viral attachment, fusion, and viral polymerase activity) than blockers of viral assembly and egress, since the latter would act downstream of luciferase reporter expression. Consistent with this assumption, the protocol yielded as the most prominent hit candidate a novel RSV-specific virus entry inhibitor class when tested in a 10,000-compound proof-of-concept campaign. Characterization of the hit compound in infection and subinfection reporter assays and tracing of resistance to point mutations in the viral F protein confirmed interference with F-mediated membrane merger as the underlying mechanism of anti-RSV activity. The RSV entry machinery emerges as highly susceptible to inhibition by small-molecule inhibitors, since structurally distinct lead compounds identified in several independent drug discovery campaigns all block membrane fusion (Roymans D, et al. (2010) Proc Natl Acad Sci USA 107(1):308-313; Douglas J L, et al. (2005) Antimicrob Agents Chemother 49(6):2460-2466; Cianci C, et al. (2004) Antimicrob Agents Chemother 48(2):413-422; Morton C J, et al. (2003) Virology 311(2):275-288). Possible reasons for this prevalence may include that entry inhibition poses lower demands on the compound than other inhibition strategies, since it does not mandate plasma membrane-permeability of the inhibitor. In addition, paramyxovirus F proteins are comparably large in size and undergo—like other class I viral fusion proteins (Plemper R K (2011) Curr Opin Virol 1(2):92-100)—complex conformational rearrangements to mediate membrane merger. Combined, the result is the presentation of multiple druggable targets for small-molecule interference. In contrast to the F proteins of most members of the paramyxovirus family, RSV F is capable of mediating not only fusion but also viral attachment (Techaarpornkul S, et al. (2001) J Virol 75(15):6825-6834; Techaarpornkul S, et al. (2002) 294(2):296-304), which may further broaden the spectrum of possible drug targets.

Five of the previously identified RSV entry inhibitors were synthetically developed to therapeutic candidate level and are at different stages of preclinical and clinical assessment (Roymans D, et al. (2010) Proc Natl Acad Sci USA 107(1):308-313; Douglas J L, et al. (2005) Antimicrob Agents Chemother 49(6):2460-2466; Cianci C, et al. (2004) Antimicrob Agents Chemother 48(2):413-422; Morton C J, et al. (2003) Virology 311(2):275-288). Biochemical docking assays suggested physical binding of two different inhibitor classes with the F 489-microdomain (Roymans D, et al. (2010) Proc Natl Acad Sci USA 107(1):308-313; Cianci C, et al. (2004) Proc Natl Acad Sci USA 101(42):15046-15051) or F residue 198, which is located in the HR-A domain and was proposed to reside in immediate vicinity of the HR-B 489-microdomain in the final 6HB fusion core. In addition to these two classes, resistance hotspots were determined for the remaining three scaffolds and, in analogy to the characterization of GPAR-3710, in all cases included F residues in the 400- and/or 489-microdomains (Douglas J L, et al. (2005) Antimicrob Agents Chemother 49(6):2460-2466; Morton C J, et al. (2003) Virology 311(2):275-288). Although recognized as surprising that distinct chemical inhibitor classes supposedly target the same F microdomain with high affinity (Cianci C, et al. (2004) Proc Natl Acad Sci USA 101(42):15046-15051), previous studies concluded that these compounds all prevent RSV entry by docking into a hydrophobic cavity near residue 489, which emerges during assembly of the 6HB structure (Roymans D, et al. (2010) Proc Natl Acad Sci USA 107(1):308-313; Cianci C, et al. (2004) Proc Natl Acad Sci USA 101(42):15046-15051). However, this hypothesis was developed before the prefusion RSV F structure was solved and previous work did not consider possible effects of resistance mutations on the conformational stability of prefusion F or the kinetics of viral entry.

Whereas direct binding to the hydrophobic pocket in the RSV 6HB is biochemically supported for two inhibitor classes (Roymans D, et al. (2010) Proc Natl Acad Sci USA 107(1):308-313; Cianci C, et al. (2004) Proc Natl Acad Sci USA 101(42):15046-15051), it is proposed based on three major lines of evidence—structural insight, biochemical characterization, and functional data—that unprecedented pan-resistance of RSV against multiple structurally diverse entry inhibitors is based on indirect escape. Firstly, compounds docking into post-fusion RSV F structures failed to provide a mechanistic explanation for the hot-spot around F residue 400 in resistance (Cianci C, et al. (2004) Proc Natl Acad Sci USA 101(42):15046-15051). It was demonstrated that the 400- and 489-microdomains are located at opposing ends of the postfusion F structure, but are posited in close proximity to each other at the intersection of stalk and head domain in prefusion F. Interestingly, several studies investigating related paramyxovirus F proteins have identified this network of non-covalent interactions between prefusion F stalk and head as a major determinant for controlling the conformational stability of the trimer (Lee J K, et al. (2007) J Virol 81(16):8821-8826; Yin H S, et al. (2006) Nature 439(7072):38-44). It was furthermore demonstrated that point mutations in this region confer resistance against a small-molecule entry inhibitor of MeV (Doyle J, et al. (2006) J Virol 80(3):1524-1536). Secondly, point mutations in either of the two resistance hot-spots reduced the structural stability of the prefusion RSV F trimer in biochemical assays and resulted in enhanced spontaneous viral inactivation rates in the absence of target cells. Thirdly, membrane fusion rates of resistant F proteins were enhanced compared to those of the parent trimer, indicating accelerated refolding of the complex from the pre- into the stable postfusion conformation.

Taken together, these observations spotlight an effective mechanism of secondary RSV resistance, in which escape mutations accumulate in F microdomains that govern the structural stability of the prefusion complex. Refolding rates of these conformationally destabilized mutant F trimers are enhanced, resulting in a hyperfusogenic phenotype and, possibly, a narrowed window of opportunity for small-molecule docking and interference with F trimer rearrangements leading to fusion pore formation. Different escape pathways were also identified for HIV resistance to the peptidic entry inhibitor Fuzeon (Eggink D, et al. (2009) J Biol Chem 284(39):26941-26950; Baldwin C E, et al. (2004) J Virol 78(22):12428-12437). However, Fuzeon escape did not coincide with resistance to other entry inhibitors (Reeves J D, et al. (2005) J Virol 79(8):4991-4999). Pan-resistance against a structurally highly diverse panel of entry inhibitors appears unique to RSV F and may amount to a substantial obstacle in the clinic.

Despite the reduction in prefusion F conformational stability, fitness of one of the resistant recRSVs was unchanged compared to the standard recRSV in a mouse pathogenesis model, while the other was only minimally attenuated. Recently established, this mouse model using the recRSV A2-L19F strain exhibits higher lung viral loads, more airway mucus, and more severe respiratory distress than both the parental A2 and line 19 strains (Moore M L, et al. (2009) J Virol 83(9):4185-4194; Lee S, et al. (2012) J Virol 86(23): 13016-13024), recapitulating key clinical parameters of infant RSV bronchiolitis (Moore M L, et al. (2009) J Virol 83(9):4185-4194; Stokes K L, et al. (2011) J Virol 85(12): 5782-5793; Lukacs N W, et al. (2006) Am J Pathol 169(3): 977-986). Efficient replication, in particular of the resistant RSV-$F_{D401E}$ recombinant in this model, raises major concern that resistance mutations, in particular in the hot-spot around F residue 400, may become prevalent in circulating RSV strains, should any of these entry inhibitor classes experience broad clinical use.

The disclosed data thus indicate that RSV entry inhibitors currently considered for clinical use are at risk to rapidly lose therapeutic benefit in the clinic due to preexisting viral resistance. Future RSV drug discovery campaigns should either be directed at inhibiting post-entry steps of viral replication or be proactively designed to conceptually circumvent pan-resistance against entry inhibitors. For instance, using the resistant recRSV A2-L19F$_{D489E}$-renilla or RSV-L19F$_{D489E}$-firefly luciferase virus described in this study as the screening agent should have a high propensity to yield hit candidates that either act post-entry or, if mechanistically possible, block viral entry without being compromised by pan-resistance.

TABLE 1

Overview of different chemical classes of highly potent RSV entry inhibitors for which resistance hot-spots have been mapped.

| Name | Structure | $^a$EC$_{50}$ | $^b$reported resistance sites |
|---|---|---|---|
| GPAR-3710 | [structure] | 0.13 µM | $F_{T400A}$ $F_{D401E}$ $F_{D486E}$ $F_{F488I}$ $F_{F488S}$ $F_{D489E}$ |

TABLE 1-continued

Overview of different chemical classes of highly potent RSV entry inhibitors for which resistance hot-spots have been mapped.

| Name | Structure | $^a$EC$_{50}$ | $^b$reported resistance sites |
|---|---|---|---|
| TMC353121 | 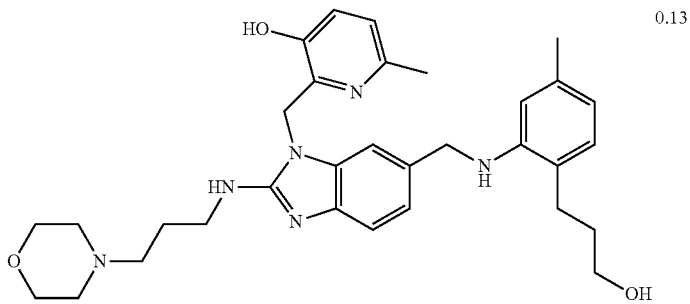 | 0.13 nM | $F_{K394R}$<br>$F_{S398L}$<br>$F_{D486N}$ |
| JNJ2408068 | 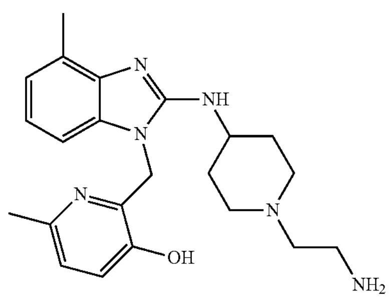 [SMILES: Cc1ccc(O)c(Cn2c(NC3CCN(CCN)CC3)nc3c(C)cccc32)n1] | 2.1 nM | $F_{K399I}$<br>$F_{D486N}$<br>$F_{E487D}$ |
| VP-14637 | 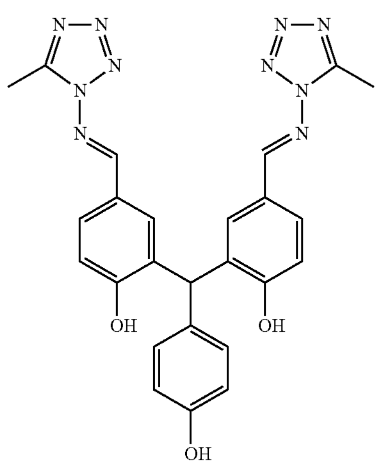 | 1.4 nM | $F_{T400A}$<br>$F_{F488Y}$ |
| BMS-433771 | 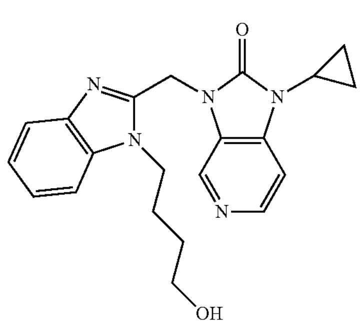 [SMILES: O=c1n(Cc2nc3ccccc3n2CCCCO)c2cnccc2n1C1CC1] | 10 nM | $F_{F140I}$<br>$F_{V144A}$<br>$F_{D392G}$<br>$F_{K394R}$<br>$F_{D489Y}$ |

TABLE 1-continued

Overview of different chemical classes of highly potent RSV entry inhibitors for which resistance hot-spots have been mapped.

| Name | Structure | $^a$EC$_{50}$ | $^b$reported resistance sites |
|---|---|---|---|
| R170591 | (structure) | 2 nM | F$_{F488I}$<br>F$_{F488L}$<br>F$_{D489Y}$ |

$^a$active concentrations are based on in vitro assays; numbers refer, when available, to the RSV A2 strain
$^b$resistance sites in the RSV F protein; mutations highlighted in red map to the F 400 microdomain, changes in blue affect the F 489 region

Example 2: Influenza Virus Reporter and Coinfection with F-Modified RSV

A replication-competent recombinant influenza virus (IAV) Nano-luciferase reporter strain (FIG. 9) was generated. The IAV nano-luciferase virus is suitable for large scale single-well, double-infection drug screening campaigns in combination with a recombinant respiratory syncytial virus (RSV) reporter strain.

The IAV nano-luciferase virus is genetically stable and returns superior reporter signals compared to currently available IAV reporter constructs (signal-to-background is increased by approximately one order of magnitude; FIG. 10).

The substrate of nano-luciferase is chemically related to those of gaussia luciferase and renilla luciferase, but distinct from that of firefly luciferase. Consequently, nano-luciferase and firefly luciferase concentrations can be determined independently in lysates of co-infected cells, allowing discrete monitoring of either pathogen (FIG. 3).

The growth kinetics of IAV nano-luciferase is comparable to that of modified RSV-L19F$_{D489E}$-firefly luciferase, allowing for its use in automated drug screening campaigns (FIG. 11).

Material and Methods:
Cell Culture, Transfection and Virus Stock.
All cell lines were maintained in Dulbecco's modified Eagle's medium supplemented with 7.5% fetal bovine serum at 37° C. and 5% CO$_2$. Baby hamster kidney (BHK21) cells stably expressing T7 polymerase (BSR-T7/5 cells) were incubated at every third passage in the presence of 500 μg/ml G-418 (Geneticin). Cell transfections were carried out using Lipofectamine 2000 (Invitrogen). RSV L19F$_{D489E}$-firefly luciferase virus stocks were purified through a 20%/60% sucrose gradient (90 minutes at 100,000×g, 4° C.) followed by virus pelleting at 60,000×g for 30 minutes at 4° C. after dilution in TNE buffer. IAV WSN-Nluc virus stocks were pelleted two times at 60,000×g for 30 minutes at 4° C. All purified virions were re-suspended in TNE buffer.

Generation and Recovery of Recombinant RSV.
Point mutations were introduced through directed mutagenesis into a shuttle vector containing the RSV L19F open reading frame, followed by transfer of the modified SacII/SalI L19F fragment into RSV L19F. The firefly luciferase gene was amplified by PCR, digested with restriction enzymes BstBI and AvrII, and ligated into an RSV L19F genomic plasmid opened with BstBI and AvrII. Recovered recombinants were subjected to RT-PCR and sequencing for confirmation of the luciferase insertion and point mutation. RSV L19F$_{D489E}$-firefly luciferase virions were amplified and titered on HEp-2 cells.

Generation and Recovery of Recombinant IAV.
The PB2-PS*-PTV-Nluc (or Gaussia)-KDEL-PS segments were generated by recombineering PCR using appropriate oligonucleotide primers. All final constructs were sequence confirmed, digested with SalI and ApaI, and ligated into an equally opened pHW12 plasmid vector. All IAV WSN-encoding genomic plasmids were co-transfected into 293T cells with lipofectamine 2000. Twenty-eight hours post-transfection, culture supernatants were harvested and overlaid onto MDCK cells, followed by an additional two-day incubation. Culture supernatants were harvested and stocked at −80° C. Recovered IAV WSN-Nluc virions were regrown and titered by plaque assay on MDCK cells.

Viral Growth Profiles.
A549 cells were infected at the indicated MOIs with RSV L19F$_{D489E}$-firefly luciferase and/or IAV WSN-Nluc in a 96-well microtiter plate format. At the specified time points post-infection, cells were lysed with Glo-lysis buffer (Promega), and luciferase activities determined sequentially using renilla (Nano luciferase) and firefly luciferase substrates and a Synergy H1 (BioTek) multimode-microplate reader in top-count mode.

Example 3: Replication-Competent Influenza Virus and Respiratory Syncytial Virus Luciferase Reporter Strains for Co-Infection High-Throughput Screening Materials and Methods
Cell Lines and Transfections
Human larynx epidermoid carcinoma (HEp-2, ATCC CCL-23), human lung carcinoma (A549, ATCC CCL-185), human bronchial epithelial (BEAS-2B, ATCC CRL-9609), human embryonic kidney (293T, ATCC CRL-3216), and Madin Darby canine kidney (MDCK, ATCC CCL-34) cells were maintained at 37° C. and 5% CO2 in Dulbecco's modified Eagle's medium (DMEM) supplemented with 7.5% fetal bovine serum. Baby hamster kidney (BHK-21) cells stably expressing T7 polymerase (BSR-T7/5 cells) (Buchholz, U. J., et al. (1999) J Virol 73:251-259) were incubated at every third passage in the presence of 500 µg/ml G-418 (Geneticin). Lipofectamine 2000 (Invitrogen) was used for all transient transfection reactions.

Generation of recIAV Reporter Strains

Recombinant IAV/WSN/33 (H1N1) (IAV-WSN) strains were generated using the 8-plasmid IAV rescue system (Hoffmann, E., et al. (2000) Proc Natl Acad Sci USA 97:6108-6113). Plasmids pHW12-PB1, pHW12-PB2, pHW12-PA, pHW12-NP, pHW12-HA, pHW12-NA, pHW12-M and pHW12-NS were kind gifts from David Steinhauer (Emory University). Recombinant IAV containing renilla and gaussia luciferase reporters in the NS1 and PB2 segments were generated as previously described (Heaton, N. S., et al. (2013) J Virol 87:8272-8281; Manicassamy, B., et al. (2010) Proc Natl Acad Sci USA 107: 11531-11536). recIAV-WSN harboring nano luciferase in the PB2 segment was constructed analogous to recIAV-WSN gaussia. Briefly, the PB2 3' packaging signal was inactivated through silent mutagenesis and a nano luciferase-encoding open reading frame (ORF) harboring a 3' KDEL-encoding endoplasmic reticulum retention signal fused to the mutant PB2 ORF through recombineering PCR. Nano and gaussia luciferase genes were amplified from plasmids pNL1.1CMV [Nluc/CMV] (Promega) and pTK-Gaussia (ThermoFisher), respectively. A 2A cleavage sequence from porcine teschovirus (Donnelly, M. L., et al. (2001) The Journal of general virology 82:1027-1041) was inserted between the PB2 and luciferase ORFs, and a copy of the original PB2 packaging signal inserted downstream of the coding cassette. All plasmids were sequence confirmed.

IAV Recovery, Amplification, and Stability Testing

All recIAV strains were recovered through rescue plasmid transfection into 293T cells and overlay of transfected cells onto MDCK cells after 28 hours of incubation. Recovered recombinants were amplified and released virions titered through plaque assay on MDCK cells. For genetic stability testing, recombinant virions were passaged consecutively four times and virus titers determined through plaque assays after each passage. In parallel, reporter titers were determined after each passage through 50% tissue culture infective dose ($TCID_{50}$) titration with bioluminescence as the readout, using a Synergy H1 (BioTek) multimode microplate reader equipped with substrate injectors.

Generation of recRSV Reporter Strains

Backbone for all recombinant RSV strains was a plasmid containing a full-length cDNA copy of a chimeric RSV-A2 genome, in which the F-encoding open reading frame was replaced with that of the line19 (L19) RSV isolate and an additional renilla luciferase ORF was added (Hotard, A. L., et al. (2012) Virology 434:129-136). The D489E substitution was introduced into L19 F through directed mutagenesis of a helper vector harboring a SacII/SalI fragment of the genome, followed by transfer into the full-length plasmid and sequence confirmation, creating recRSV A2-L19$F_{D489E}$-renilla. Recombineering PCR was employed to add RSV intergenic junctions and flanking regions to firefly luciferase ORF, followed by substitution of a renilla luciferase-containing BstBI/AvrII fragment in recRSV A2-L19$F_{D489E}$-renilla with the equivalent fragment harboring firefly luciferase. To generate the fireSMASh ORF, the SMASh tag was fused in frame to the 3' end of the firefly luciferase ORF through recombineering PCR, followed by addition of the RSV flanking regions and BstBI/AvrII transfer into the full length cDNA genome copy as before. recRSV were recovered through co-transfection with RSV L, N, P, and M2-encoding helper plasmids into BSR-T7/5 cells as previously described (Hotard, A. L., et al. (2012) Virology 434:129-136), and subjected to RT-PCR and cDNA sequencing.

RSV Recovery, Amplification, and Stability Testing recRSV stocks were grown on HEp-2 cells inoculated at a multiplicity of infection (MOI) of 0.01 pfu/cell. Infected cells were kept for 16 hours at 37° C., followed by incubation at 32° C. for five to seven days. Cell-associated progeny virus was released through one freeze/thaw cycle and titers determined by $TCID_{50}$ titration on HEp-2 cells. For genetic stability testing of the SMASh tagged virus, recovered recRSV A2-L19F-fireSMASh virions were consecutively passaged five times on HEp-2 cells. Progeny virions of the second and fifth passage were incubated in the presence or absence of 3 µM asunaprevir (ASV) and infected cell lysates subjected to SDS-PAGE and immunoblotting.

SDS-PAGE and Antibodies

Infected cells ($6 \times 10^5$ per well in a 6-well plate format) were lysed 40 hours post-infection in RIPA buffer (1% sodium deoxycholate, 1% NP-40, 150 mM NaCl, 50 mM Tris-Cl, pH 7.2, 10 mM EDTA, 50 mM sodiumfluoride, protease inhibitors [Roche], 1 mM phenylmethylsulfonyl fluoride), subjected to clearance centrifugation (20,000×g for 30 minutes at 4° C.) and cleared lysates diluted with UREA buffer (200 mM Tris, pH 6.8; 8 M urea; 5% sodium dodecyl sulfate (SDS); 0.1 mM EDTA; 0.03% bromphenolblue; 1.5% dithiothreitol) at a 1:2-ratio. Denatured (30 minutes at 50° C.) lysates were fractioned through gel electrophoresis on 10% Tris/Glycine gels, transferred to polyvinylidene difluoride (PVDF) membranes (GE Healthcare), and protein material detected through decoration with specific antibodies directed against firefly luciferase (PAS-32209, ThermoFisher) or glyceraldehyde-3-phosphate dehydrogenase (anti-GAPDH, Calbiochem). Immunoblots were developed using mouse IgG light chain-specific HRP-conjugated secondary antibodies (Jackson) and a ChemiDoc digital imaging system (Bio-Rad).

Purification of Virus Stocks

Two alternative strategies were explored to remove contaminating luciferase proteins from virus stocks. Progeny virions in culture supernatants (IAV stocks) or released through one freeze/thaw cycle from infected cells (RSV stocks) were cleared (4,000×g for 20 minutes at 4° C.), then pelleted (60,000×g for 30 minutes at 4° C.). Pelleted material was resuspended in THE buffer (50 mM Tris/Cl pH 7.2, 10 mM EDTA) and purified through a 20/60% one-step sucrose gradient in THE buffer (100,000×g for 2 h at 4° C.). Virions were harvested from the gradient intersection. Alternatively, cleared RSV stocks were purified and polished through size exclusion and binding chromatography by passaging through dual functionality Capto Core 700 resin (GE Healthcare) using an AKTA avant chromatography system (GE Healthcare). After purification through either method, virus stocks were stored in aliquots at −80° C.

Reporter Expression Profiles

Cells ($1.5 \times 10^4$ per well in a 96-well plate format) were infected with purified virus stocks at different MOIs as specified or co-infected. At the specified time points, cells were lysed in situ with 50 µl Glo-lysis buffer (Promega) for five minutes at 37° C. and samples transferred into solid white 96-well plates. Lysates were kept frozen until the time course was completed, then equilibrated to ambient temperature simultaneously and relative luciferase activities determined using the Synergy H1 reader and injectors to add renilla-Glo, bright-Glo or dual-Glo substrates (all Promega), respectively (lag time before reading three minutes for each well). Values are expressed for each reporter strain relative to the highest reading recorded for this strain, and represent averages of at least three independent repeats.

Compounds

All compounds were dissolved in DMSO to 10 mM concentration and stored at −80° C. The MScreen software package (Jacob, R. T., et al. (2012) J Biomol Screen 17:1080-1087) was used for electronic compound management, HTS data storage and data analysis. Compounds of the NIH Clinical Collection (NCC) were received from the NIH Small Molecule Repository in 96-well plates, inventoried in MScreen, and reformatted into barcoded 384-well daughter plates using a Nimbus liquid handler (Hamilton Robotics) with multichannel pipetting head. In addition, known antimyxovirus bioactives identified in previous drug discovery campaigns were included in empty wells in the NCC daughter plates. Thirty-two wells on each 384-well plate received compound JMN3-003 (Krumm, S. A., et al. (2011) PLoS ONE 6:e20069) for positive control, and another 32 wells received volume equivalents of vehicle (DMSO) only.

Assay Validation in 96-Well Format

BEAS-2B cells ($1\times10^4$/well, seeded in 40 µl in white wall/clear bottom 96-well plates) were treated manually (1 µl/well) with a set of known bioactives (diluted in growth media to 5% DMSO, final concentration as specified), then infected or co-infected with 10 µl of the IAV and RSV reporter viruses at different MOIs as specified. Final DMSO concentrations were 0.1%, at which no vehicle-induced cytotoxic effect was detected. After a 40-hour incubation period at 37° C., luciferase substrates (20 µl/well) were injected as before directly into the assay plates and relative bioluminescence intensities determined. Each compound was assessed in five replicates. For quantitative assay validation, Z' values (Zhang, J. H., et al. (1999) J Biomol Screen 4:67-73) were calculated according to the formula $Z'=1-(3SD_{(C)}+3SD_{(B)})/(Mean_{(C)}-Mean_{(B)})$, with C=control and B=background.

Automated HTS Protocol in 384-Well Plate Format

BEAS-2B cells ($8\times10^3$/well) were injected in 30 µl/well into barcoded white wall/clear bottom 384-well plates using a MultiFlo automated dispenser (BioTek) equipped with dual 10 µl peristaltic pump manifolds, collected (150×g for 60 seconds at 25° C.), and incubated for 3 hours at 37° C. and 5% $CO_2$. Compound was added to a final concentration of 5 µM (20 nl/well) using a high-density pin tool (V&P Scientific) attached to the pipetting head of the Nimbus liquid handler, followed by co-infection with recRSV A2-L19F$_{D489E}$-fireSMASh (MOI=0.1) and recIAV WSN-NanoLuc (MOI=0.02) in 10 µl/well using the MultiFlo dispenser unit, spin collection (150×g for 60 seconds at 25° C.), and incubation for 40 hours at 37° C. and 5% $CO_2$. Final vehicle (DMSO) concentration was 0.05%. Barcodes of source and assay plates were automatically detected and recorded by the Nimbus unit at the time of stamping. Using a stacker unit with integrated barcode reader (Biotek) attached to the H1 synergy plate reader, plates were automatically loaded, dual-Glo substrates (15 µl/well each) injected, and bioluminescence recorded after a three minute lag time for each well and substrate. Readouts were automatically saved by plate barcode. For manual calculation of Z' values, luciferase activities in positive and vehicle wells were processed as detailed above.

Dose-Response Counterscreens

Two-fold serial dilutions of hit candidates were prepared in 384-well plates in three replicates each using the Nimbus liquid handler. BEAS-2B cells ($8\times10^3$/well) were then plated as before, serial dilutions transferred using the pin-tool, and cells infected with recRSV A2-L19F$_{D489E}$-fireSMASh (MOI=0.1), recRSV A2-L19F-renilla (MOI=0.1), or recIAV WSN-NanoLuc (MOI=0.02), or left uninfected for cell viability assessment. Reporter signals were recorded as outlined above. To determine cell viability, PrestoBlue substrate (life technologies) was added after 40-hour incubation of cells at 37° C. (5 µl/well) and top-read fluorescence (excitation 560 nm; emission 590 nm) at gain 80 recorded after 45 minutes of incubation at 37° C. Four-parameter variable slope regression modeling was applied to determine 50% active ($EC_{50}$) and toxic ($CC_{50}$) concentrations.

Data Normalization and Analysis

The MScreen package was employed for automated data analysis. Plate reader raw data files together with source and assay plate barcode maps generated by the Nimbus system were directly imported into the package, and Z' values automatically calculated based on the designated control wells. Since the NCC plates contained a high density of known bioactives, the normalized percent inhibition method was applied for data analysis. Normalized relative inhibition values were calculated for each compound by subtracting each value from the average of the plate vehicle controls, followed by dividing the results by the difference between the means of plate vehicle and positive controls. Hits candidates were defined as compounds showing ≥80% inhibition of normalized signal intensity against either or both viral targets. For analysis of plates, the cellHTS2 package (Boutros, M., et al. (2006) Genome Biol 7:R66) was employed to calculate percent inhibition as described above, followed by scaling of plates by dividing the normalized value of each well by the median absolute deviation of the plate. The SciFinder database package (American Chemical Society) was used to query chemical databases with hit candidate structures to evaluate known bioactivities.

Statistical Analysis

The Excel and Prism 6 (GraphPad) software packages were used for data analysis. Statistical significance of differences between two sample groups were assessed by unpaired two-tailed t tests (two sample groups; Excel), or two-way analysis of variance (ANOVA; Prism 6) in combination with Tukey's multiple comparison post-tests (multiple sample groups) as specified in the figure legends. Experimental uncertainties are identified by error bars, representing standard deviations (SD).

Results

Different versions of replication-competent IAV strains encoding luciferase reporters were described recently (Heaton, N. S., et al. (2013) J Virol 87:8272-8281; Tran, V., et al. (2013) J Virol 87:13321-13329). Of these, a recombinant IAV-PR8 harboring a Gaussia open reading frame in the PB2 genome segment reportedly replicated efficiently, was genetically stable, and showed high luciferase activity levels (Heaton, N. S., et al. (2013) J Virol 87:8272-8281).

Generation of a Replication-Competent IAV-WSN PB2-NanoLuc Reporter Strain

Most laboratory IAV strains require the addition of exogenous trypsin for proteolytic maturation of the HA protein for priming of the viral entry machinery. To gain independence of trypsin activation in all screening plates, the analogous PB2-Gaussia recombinant in the trypsin-independent IAV-WSN genetic background was generated (FIG. 12A) (Lazarowitz, S. G., et al. (1973) Virology 56:172-180). The resulting recIAV-WSN Gaussia showed efficient replication and reporter expression in the absence of exogenous trypsin (FIG. 12B). However, the signal window of Gaussia remained below 10 (FIG. 12C). Towards extending the assay range, Gaussia luciferase was substituted for the recently developed Nano luciferase (NanoLuc, FIG. 12A), which uses the same basic substrate chemistry as Gaussia and Renilla luciferases but combines a small protein size with high signal intensities. Recovered recIAV-WSN NanoLuc indeed returned an over six-fold improved signal window and showed superior absolute luciferase signal intensities compared to recIAV-WSN Gaussia (FIGS. 12C and 12D). Z' values in either case far exceeded 0.5, suggesting that the assay is suitable for automation. Serial passaging of this recombinant confirmed equivalent genetic stability of recTAV-WSN Gaussia and recTAV-WSN NanoLuc. By comparison, luciferase activity rapidly disappeared when a recIAV-WSN NS-Gaussia was subjected to passaging, which harbors the luciferase open reading frame in the NS genome segment (FIG. 12E). The design of this recombinant followed the strategy outlined in a recent report (Manicassamy, B., et al. (2010) Proc Natl Acad Sci USA 107:11531-11536).

An IAV-Compatible Recombinant RSV-Firefly Reporter Strain

In the original evaluation of a dual-myxovirus HTS protocol, IAV and MeV-based reporter expression overlapped, whereas the original recRSV-L19F-renilla reporter strain showed a substantial delay in luciferase expression over a range of different inoculum multiplicities of infection (MOIs). When comparing RSV and MeV in cell culture, most notably is the divergence in cell-to-cell fusion (syncytia formation) after infection, which represents the hallmark of MeV cytopathicity but is much less pronounced in the case of RSV. The lower rate of lateral RSV spread may therefore cause the slower reporter expression kinetics. Experiments were therefore conducted to determine whether a hyperfusogenic RSV variant would alleviate the problem. An RSV recombinant was generated with a D to E substitution of fusion (F) protein residue 489 that renders it hyperfusogenic (Yan, D., et al. (2014) Proc Natl Acad Sci USA 111, E3441-3449).

To test the effect of hyperfusogenicity on reporter expression kinetics, a recRSV-L19F$_{D489E}$-firefly strain (FIG. 13A) analogous to the previously described recRSV-L19F-renilla, was generated since firefly and nano luciferase activities are based on distinct substrate chemistry and can be independently quantified. Independent of the nature of the luciferase reporter included, time to peak reporter activity of F$_{D489E}$ mutant strains was less than half that of a strain harboring standard F (FIG. 13B). These results suggest that the hyperfusogenic recRSV-L19F$_{D489E}$-firefly strain should be suitable for co-infection screens with recIAV WSN-NanoLuc. When attempting to purify recRSV-L19F$_{D489E}$-firefly preparations from contaminating firefly protein that was synthesized during stock growth, however, both gradient ultracentrifugation and layered bead chromatography purification strategies successfully reduced renilla luciferase contaminations, but by comparison remained inefficient against firefly luciferase (FIG. 13C). As a consequence, the signal window of assays based on the recRSV-L19F$_{D489E}$-firefly strain was approximately 8-fold lower than that achievable with recRSV-L19F$_{D489E}$-renilla (FIG. 13D), excluding its use in high-density HTS applications.

SMASh Technology to Eliminate Contaminating Firefly Protein

In search of an innovative approach to suppress the build-up of contaminating firefly protein during growth of virus stocks, the use of small molecule-assisted shutoff (SMASh) technology was explored for induced protein degradation. Unlike other systems designed to induce protein turnover, only SMASh functions as a single-chain system and in the stabilized state returns near-native proteins. Added as a genetic tag, SMASh consists of a hepatitis C virus-derived NS3 protease flanked by a strong degron domain inducing proteasomal degradation. An NS3 protease site is positioned at the intersection of the SMASh tag and the target protein (FIG. 14A). Under normal conditions, NS3 autoproteolysis separates the tag, returning the near-native target protein. In the presence of a strong NS3 inhibitor such as the clinical candidate ASV (Scola, P. M., et al. (2014) J Med Chem 57:1730-1752), however, autoproteolysis is blocked and the degron domain induces rapid degradation of the tag and affixed target protein.

A SMASh tag was added to the firefly open reading frame and the corresponding recRSV-L19F$_{D489E}$-fireSMASh recombinant was successfully recovered Immunoblotting with antibodies directed against firefly luciferase confirmed efficient degradation of the tagged protein after incubation in the presence of ASV, while steady state levels closely matched those of untagged firefly luciferase in the absence of the drug (FIG. 14B). ASV had no effect on progeny virus titers (FIG. 14C) and the SMASh tag remained stable over multiple passages of this virus strain (FIG. 14D). However, growth of recRSV-L19F$_{D489E}$-fireSMASh in the presence of ASV reduced firefly luciferase activity by approximately 90% (FIG. 14E), which paved the path for an over 23-fold increased signal window of recRSV-L19F$_{D489E}$-fireSMASh compared to recRSV-L19F$_{D489E}$-firefly (FIG. 14F). These results suggest that recIAV WSN-NanoLuc and recRSV-L19F$_{D489E}$-fireSMASh may represent a suitable pair for dual-pathogen drug discovery campaigns.

Co-Infection Conditions

To establish suitable assay conditions, three human respiratory cell lines, HEp2, BEAS-2B, and A549, were first independently infected with recRSV-L19F$_{D489E}$-fireSMASh and recIAV WSN-NanoLuc at different multiplicities of infection and measured relative luciferase activities at 40 hours post-infection. At each MOI, RSV-based reporter expression was reduced in A549 cells by over 90% compared to each of the other two cell lines (FIG. 15A), and a comparable reduction was observed with IAV-based NanoLuc expression in HEp2 cells (FIG. 4B).

BEAS-2B cells were therefore selected as best suited for RSV/IAV co-infection experiments and reporter expression profiles generated after infection with either virus individually (FIGS. 15C and 15D) or in combination (FIG. 15E). Peak luciferase activities (RLUs ≥80% of max) overlapped in an approximately 7-hour time window (37-44 hours post-infection) when cells where co-infected with recRSV-L19F$_{D489E}$-fireSMASh at an MOI of 0.1 and recIAV WSN-NanoLuc at an MOI of 0.02. All subsequent experiments followed these assay conditions, and reporter signals were measured 38-42 hours post-infection.

Assay Miniaturization and Validation

Towards validating the assay for screening campaigns, the protocol was initially applied in 96-well plate format to a panel of known bioactives with discrete anti-myxovirus activity and cytotoxic compounds for comparison (FIG. 16A). Relative inhibition was calculated through normalization of raw data for control wells that received vehicle (DMSO) only. In all cases, known myxovirus inhibitors with different antiviral profiles were correctly identified, and Z' values (FIG. 16B) exceeded 0.5, defining a robust assay (Zhang, J. H., et al. (1999) J Biomol Screen 4: 67-73). The previously characterized RSV fusion blockers GPAR3710 and BMS-433771 (Yan, D., et al. (2014) Proc Natl Acad Sci USA 111, E3441-3449; Cianci, C., et al. (2004) Antimicrob Agents Chemother 48:413-422) did not emerge as hits, confirming that the use of the pan-resistant RSV-$F_{D489E}$ mutant can reliable suppress the discovery of additional, undesirable RSV entry inhibitors that are also sensitive to the pan-resistance escape mechanism (Yan, D., et al. (2014) Proc Natl Acad Sci USA 111, E3441-3449).

Based on this proof-of-concept data, the assay was miniaturized to 384-well plate format and a 2-plate pilot set of the National Compound Collection (NCC) was screened in quadruplicate to quantify assay suitability for automated hit discovery and determine plate-to-plate and day-to-day reproducibility. Executed under HTS conditions, this validation campaign returned robust Z' values exceeding 0.5 and a signal window greater than 50 (RSV) and 20 (IAV), respectively (FIG. 16B).

Of the NCC test library, 11 hit candidates were identified that inhibited primary reporter activities by 80% or greater of either or both target viruses (Table 2). The majority of these hit candidates were previously associated with diverse antiviral and/or cytotoxic activities. Graphic representation of all assay validation replicates in Z-score profiles revealed that the dual myxovirus protocol shows high plate-to-plate reproducibility (FIG. 16C). Plotting of individual z-scores of each replicate as a function of mean %-inhibition values for each compound and viral target furthermore revealed a strong correlation between normalized scores and effect sizes for all hit candidates (FIG. 16D).

TABLE 2

Primary screening hit candidates of the NCC collection, based on automated screening of the library in four replicates in 384-well format. Results are grouped by RSV-specific hit candidates, IAV-specific hit candidates, and inhibitors of both target viruses.

| Name | % Inhibition (anti-RSV)[1] | % Inhibition (anti-IAV)[2] | Bioactivity/ Biological target[3] | Known Antiviral Targets[4] |
|---|---|---|---|---|
| RSV predominant | | | | |
| Temozolomide | 96 ± 1.3 | 55 ± 3.2 | DNA replication | None |
| Raltitrexed | 91 ± 1.0 | 60 ± 6.5 | Thymidylate synthase | Cytomegaloviruses |
| Rosiglitazone | 85 ± 5.8 | 35 ± 5 | Adenomatosis polyposis coli 2 Eukaryotic translation initiation factor 5A-1 Peroxisome proliferator-activated receptor-gamma | Rotaviruses |
| Etoposide | 80 ± 6.6 | 56 ± 5.6 | DNA topoisomerase II | Cytomegaloviruses |
| Vincristine | 79 ± 6.9 | 50 ± 2.9 | Microtubule assembly | None |
| IAV predominant | | | | |
| Actinomycin D | 52 ± 9.6 | 104 ± 1.5 | RNA synthesis | Reovirus type 2 |
| Triptolide | 1.5 ± 21 | 103 ± 1.2 | XPB (a subunit of TFIIH) | HIV-1 |
| Epirubicin | 62 ± 6.3 | 75 ± 3.1 | DNA intercalator 104) | Heptatitis C |
| Inhibition of both reporter strains | | | | |
| Methotrexate | 99 ± 0.5 | 100 ± 0.6 | Dihydrofolate reductase, Deoxycytidine kinase | Murine and human cytomegalovirus |
| Homoharringtonine | 98 ± 0.5 | 90 ± 2.6 | 60S ribosome inhibitor | Recombinant murine coronavirus |
| Idarubicin | 95 ± 1.3 | 97 ± 1 | DNA topoisomerase II | Encephalomyocarditis virus (EMCV) |

[1,2]based on four independent replicate screens; mean % inhibition ± SD are shown.
[3,4]previously proposed activity, target, and antiviral spectrum, if known Test Screen of a 1280-Compound Library For proof-of-concept of hit identification under single-replicate screening conditions, the validated assay was applied to the LOPAC1280 library of pharmacologically active compounds (FIG. 17A). This campaign yielded 24 primary hit candidates (1.875% hit rate). Primary positives included, amongst others, licensed anti-influenza virus and anti-RSV therapeutics (Zanamivir and Ribavirin, respectively), protein biosynthesis blockers (i.e. Emetine), and DNA/RNA synthesis inhibitors (i.e. PMEG and Idarubicin) (Table 3).

TABLE 2

Dose-response counterscreening of hit candidates identified through automated screening of the LOPAC1280 library in single replicate in 384-well format.

| Name | $EC_{50}{}^a$ IAV WSN-nanoLuc [μM] | $EC_{50}{}^a$ RSV A2-L19F-renilla [μM] | $EC_{50}{}^a$ RSV A2-L19F$_{D489E}$-fireSMASh [μM] | $CC_{50}{}^a$ (PrestoBlue cell viability) [μM] | Proposed target/ bioactivity | SI [$CC_{50}/EC_{50}$] Comment |
|---|---|---|---|---|---|---|
| Aminopterin | 0.09 (0.07-0.11) | 0.05 (0.03-0.07) | 0.07 | 10 | dihydrofolate reductase/purine synthesis | $SI_{IAV}$ 111 $SI_{RSV}$ 143 conf. broad spectrum[79, 80] |
| Brequinar | 2.6 (2.3-2.9) | 1.8 | 1.6 (1.3-2.1) | >10$^b$ | DHODH/pyrimidine synthesis | $SI_{IAV}$>3.8 $SI_{RSV}$>6.3 conf. broad spectrum[81, 82] |
| Gemcitabine | 0.1 (0.09-0.14) | 0.05 (0.04-0.06) | 0.09 (0.07-0.12) | >10 | nucleoside analog | $SI_{IAV}$>100 $SI_{RSV}$>111 HIV, IAV[49, 50] |
| Zanamivir | 0.02 (0.01-0.04) | Inactive | Inactive | >10$^b$ | neuraminidase | $SI^{IAV}$>500 IAV inhibitor[83] |
| Calcimycin | n.d.$^c$ | n.d.$^c$ | n.d.$^c$ | tox$^d$ | cation ionophore | tox discarded |
| Emetine | n.d.$^c$ | n.d.$^c$ | n.d.$^c$ | tox$^d$ | ribosome | tox discarded |
| ET-18-OCH3 | inactive$^e$ | inactive$^e$ | inactive$^e$ | >10$^b$ | PIPLC/PKC | failed conf. |
| Sunitinib | n.d.$^c$ | n.d.$^c$ | n.d.$^c$ | tox$^d$ | RTKs | tox discarded |
| Idarubicin | n.d.$^c$ | n.d.$^c$ | n.d.$^c$ | tox$^d$ | topoisomerase | tox discarded |
| Fenretinide | inactive$^e$ | 4.8 | 3.6 (2.9-4.6) | >10$^b$ | activation of stress kinases; induces autophagy | $SI_{RSV}$>2.8 Dengue[62], HIV[61] |
| BNTX-7 | inactive$^e$ | 6.5 (0.14-307) | 2.5 (1.8-3.6) | >10$^b$ | DOR1 | $SI_{RSV}$>4 |
| Lometrexol | n.d.$^c$ | n.d.$^c$ | n.d.$^c$ | tox$^d$ | purine synthesis | tox discarded |
| PMEG | 0.2 (0.1-0.4) | 0.1 (0.07-0.15) | 0.1 (0.09-0.18) | 10 | acyclic nucleotide analog | $SI_{IAV}$ 50 $SI_{RSV}$ 100 HPV[67] |
| Nitrendipine | inactive$^e$ | inactive$^e$ | inactive$^e$ | >10$^b$ | dihydropyridine calcium channel | failed conf. |
| PD173952 | n.d.$^c$ | n.d.$^c$ | n.d.$^c$ | tox$^d$ | Src kinase | tox discarded |
| K114 | inactive$^e$ | inactive$^e$ | inactive$^e$ | >10$^b$ | amyloid-specific dye | failed conf. |
| Phenanthroline | n.d.$^c$ | n.d.$^c$ | n.d.$^c$ | 2.4$^d$ | metalloproteases | tox discarded |
| Auranofin | n.d.$^c$ | n.d.$^c$ | n.d.$^c$ | tox$^d$ | TLR signaling | tox discarded |
| Sanguinarine | n.d.$^c$ | n.d.$^c$ | n.d.$^c$ | tox$^d$ | Na+/K+ ATPase | tox discarded |
| Stattic | 3.3 (2.2-5.1) | 15.1 | 5.9 | 10 | STAT3 | $SI_{IAV}$ 3 |
| PD-166285 | n.d.$^c$ | n.d.$^c$ | n.d.$^c$ | tox$^d$ | RTKs | tox discarded |
| Ribavirin | 4.5 (2.9-5.3) | 2.9 (1.6-5.4) | 2.6 (2.1-3.2) | >10$^b$ | nucleoside analog | $SI_{IAV}$>2.2 $SI_{RSV}$>3.9 broad spectrum[84] |
| Triamterene | inactive$^e$ | inactive$^e$ | inactive$^e$ | >10$^b$ | epithelial Na+ channel | failed conf. |

TABLE 2-continued

Dose-response counterscreening of hit candidates identified through automated screening of the LOPAC1280 library in single replicate in 384-well format.

| Name | $EC_{50}{}^a$ IAV WSN-nanoLuc [µM] | $EC_{50}{}^a$ RSV A2-L19F-renilla [µM] | $EC_{50}{}^a$ RSV A2-L19F$_{D489E}$-fireSMASh [µM] | $CC_{50}{}^a$ (PrestoBlue cell viability) [µM] | Proposed target/ bioactivity | SI [$CC_{50}/EC_{50}$] Comment |
|---|---|---|---|---|---|---|
| BIX 01294 | inactive[e] | inactive[e] | inactive[e] | >10[b] | histone methyltransferase | failed conf. |
| Triptolide | 0.15 (0.11-0.21) | 0.6 | 0.4 (0.3-0.5) | 0.3 (0.22-0.4) | XPB (a subunit of TFIIH) | tox discarded |

[a]calculated through four-parameter variable slope regression modeling. Raw values are based on luciferase reporter expression and represent means of three independent replicates calculated $EC_{50}$ concentrations and 95% confidence intervals are shown
[b]highest concentration assessed 10 µM
[c]not determined based on initial cell viability testing
[d]less than 50% cell viability after exposure of cells for 44 hours at ≤10 µM
[e]less than 50% reduction of mean reporter signal All compounds were picked (Table 3) and subjected to cytotoxicity testing. Only candidates that reduced cell viability by less than 50% at twice the screening concentration (10 µM) were admitted to automated dose-response testing (14 compounds; Table 3) against the primary screening strains. Interference with luciferase reporter or the NS3 protease activity of the SMASh tag was addressed in parallel by testing against a standard recRSV A2-L19F reporter strain lacking the $F_{D489E}$ resistance mutations and expressing renilla luciferase that does not share substrate chemistry with firefly luciferase (Hotard, A. L., et al. (2012) Virology 434:129-136). Compound interference with nano-Luciferase is addressed by testing against cells transiently transfected with a nano-luciferase expression plasmid in our confirmation pipeline, but we did not implement this counterscreen in this exercise since only the licensed influenza drug Zanamivir selectively inhibited the IAV reporter. Whenever possible, 50% active and cytotoxic concentrations of the selected hit candidates were calculated for all assay targets through four-parameter variable slope regression modeling (Table 3).

Triptolide of the NCC test-set originally demonstrated preferential activity against the IAV reporter strain and was likewise selected for dose-response testing and sourced. Of the resulting 15 candidates, five showed only a marginal inhibitory effect against the primary screening strains or were inactive, and Triptolide returned an SI ($CC_{50}/EC_{50}$) value below two at dose-response testing. The remaining nine viable primary hits either blocked preferentially RSV (2 compounds) or IAV (2 compounds) reporter expression, or suppressed both reporter strains (5 compounds) (FIG. 17B).

First inspection reveals that these confirmed hits can be classified into three distinct groups: i) licensed antiviral therapeutics such as Zanamivir and Ribavirin; ii) compounds with documented broad-spectrum antiviral activity such as the nucleoside analog Gemcitabine (Denisova, O. V., et al. (2012) J Biol Chem 287:35324-35332; Clouser, C. L., et al. (2012) Antimicrob Agents Chemother 56:1942-1948) and inhibitors of the purine or pyrimidine biosynthesis pathways such as Aminopterin and Brequinar, respectively (Arteaga, C. L., et al. (1989) Cancer Res 49:4648-4653; Nichol, C. A., et al. (1950) Proc Soc Exp Biol Med 74:403-411); and iii) compounds not yet extensively associated with anti-ortho- or paramyxovirus activity (Fenretinide, BNTX-7, and PMEG hydrate (Table 3)). Of these, Fenretinide and BNTX-7 selectively inhibited RSV, while the IAV reporter strain was unaffected at the highest concentration tested. PMEG hydrate blocked both reporter strains, although potency against RSV was approximately 2-fold higher than against IAV.

These results demonstrate that the new generations of recombinant RSV and IAV reporter strains generated in this study can be combined in a robust screening protocol miniaturized to 384-well format. The assay successfully identifies licensed therapeutics and compounds with known anti-myxovirus activity. A set of RSV inhibitors merits further mechanistic evaluation.

In this study, a dual pathogen myxovirus HTS protocol was developed and validated that uses innovative protein engineering technology for the simultaneous discovery of pathogen-specific and broad spectrum hit candidates (FIG. 18). There are several major advantages of this protocol over traditional single pathogen screens: i) compared to consecutive screening of a library against individual viral targets, the dual pathogen protocol using replication-competent recombinant viruses shows superior cost and resource effectiveness; ii) the screening agents used in the new approach, IAV and RSV, are clinically the most significant members of the myxovirus families; iii) in addition to identifying broad-spectrum blockers, the dual readout strategy creates a bona fide "internal standard" for each well, excluding cytotoxic and undesirable promiscuous compounds effectively from the pool of virus-specific hit candidates at the stage of primary screening; iv) the new assay is applicable to a broad range of host cell lines including human respiratory epithelial cells; and v), the current assay is suitable for both single cycle and multiple cycle infections, providing flexibility in the choice of inoculum MOI and allowing the interrogation of all stages of the viral live cycle.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant respiratory syncytial virus (RSV) vector, comprising an RSV genome encoding an infectious RSV virion operably linked to an expression control sequence, wherein the RSV genome comprises a nucleic acid encoding a fusion (F) protein having a D401E mutation, a D489E mutation, or combination thereof that allows a RSV virus produced by expression of the RSV vector to escape from GPAR-3710 inhibition, wherein the fusion (F) protein mutation positions correspond to SEQ ID NO. 1, wherein the RSV genome further comprises a nucleic acid encoding a luciferase, and wherein the RSV genome further comprises a nucleic acid encoding a small-molecule assisted shutoff (SMASh) tag wherein the SMASh tag comprises a protease cleavage site, hepatitis C virus-derived NS3 protease domain, and a degron domain.

2. The recombinant RSV vector of claim 1, wherein the mutation is a D401E mutation.

3. The recombinant RSV vector of claim 1, wherein the mutation is a D489E mutation.

4. The recombinant RSV vector of claim 1, wherein the RSV genome is derived from an RSV line19 (L19) strain or an RSV A2 strain.

5. The recombinant RSV vector of claim 1, wherein the RSV genome is derived from a chimeric A2 strain, wherein the nucleic acid encoding the F protein is derived from an RSV L19 strain.

6. The recombinant RSV vector of claim 1, wherein the recombinant RSV vector further comprises a firefly luciferase.

7. The recombinant RSV vector of claim 1, wherein the recombinant RSV vector further comprises a *Renilla* luciferase.

8. The recombinant RSV vector of claim 1, wherein the vector comprises a bacterial artificial chromosome backbone.

9. An infectious RSV virion produced by expression of the recombinant RSV vector of claim 1 in a host cell.

10. A method of screening for antiviral agents, comprising
   (a) contacting a culture comprising the infectious RSV virion of claim 9 with a candidate agent; and
   (b) assaying the culture for RSV levels or activity;
   wherein a decrease in RSV levels or activity is an indication that the candidate agent is an effective antiviral agent for RSV.

11. The method of claim 10, wherein the RSV genome comprises a nucleic acid encoding a first luciferase, wherein step (b) comprises contacting the culture with a substrate for the first luciferase, and assaying the culture for bioluminescence, wherein a decrease in bioluminescence from the first luciferase activity is an indication that the candidate agent is an effective antiviral agent for RSV.

12. The method of claim 11, wherein the culture further comprises an infectious influenza virion encoded by a recombinant influenza vector comprising an influenza genome encoding a second luciferase that has a substrate distinct from the first luciferase,
   wherein the infectious influenza virus virion and the infectious RSV virion have comparable growth kinetics,
   wherein the method further comprises contacting the culture with a substrate for the second luciferase and assaying the culture for bioluminescence,
   wherein a decrease in bioluminescence from the second luciferase activity is an indication that the candidate agent is an effective antiviral agent for influenza,
   wherein a decrease in bioluminescence from both the first luciferase activity and second luciferase activity is an indication that the candidate agent is an effective pan-antiviral agent.

13. The method of claim 11, wherein the mutation is a D489E mutation.

14. The method of claim 11, wherein the first luciferase comprises firefly luciferase, wherein the second luciferase comprises nano-luciferase, *gaussia* luciferase, or *Renilla* luciferase.

15. The method of claim 11, wherein the influenza genome is derived from strain WSN-33 (H1N1).

16. A recombinant nucleic acid, comprising a respiratory syncytial virus (RSV) fusion (F) protein having a D401E mutation, a D489E mutation, or a combination thereof, operably linked to a heterologous expression control sequence, wherein the D401E mutation, the D489E mutation, or combination thereof allows an RSV virus produced by expression of the recombinant nucleic acid to escape from GPAR-3710 inhibition wherein the RSV F protein mutation positions correspond to SEQ ID NO. 1.

* * * * *

SEQUENCE LISTING

<160> NUMBER OF SEQ ID NOS: 8

<210> SEQ ID NO 1
<211> LENGTH: 574
<212> TYPE: PRT
<213> ORGANISM: Respiratory syncytial virus

<400> SEQUENCE: 1

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Lys Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Arg Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Lys Cys Lys Val Gln Ser Asn Arg Val Phe Cys Asp
        355                 360                 365
```

```
Thr Met Tyr Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Ile Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 15222
<212> TYPE: DNA
<213> ORGANISM: Human respiratory syncytial virus

<400> SEQUENCE: 2
acgcgaaaaa atgcgtacaa caaacttgca taaaccaaaa aaatggggca aataagaatt      60
tgataagtac cacttaaatt taactcccct tggttagaga tgggcagcaa tcattgagta     120
tgataaaagt tagattacaa aatttgtttg acaatgatga agtagcattg ttaaaaataa     180
catgctatac tgataaatta atacatttaa ctaacgcttt ggctaaggca gtgatacata     240
caatcaaatt gaatggcatt gtgtttgtgc atgttattac aagtagtgat atttgcccta     300
ataatatat  tgtagtaaaa tccaatttca caacaatgcc agtactacaa aatggaggtt     360
atatatggga atgatggaa  ttaacacatt gctctcaacc taatggtcta ctagatgaca     420
attgtgaaat taaattctcc aaaaaactaa gtgattcaac aatgaccaat tatatgaatc     480
aattatctga attacttgga tttgatctta atccataaat tataattaat atcaactagc     540
aaatcaatgt cactaacacc attagttaat ataaaactta acagaagaca aaaatgggc      600
aaataaatca attcagccaa cccaaccatg gacacaaccc acaatgataa tacaccacaa     660
agactgatga tcacagacat gagaccgttg tcacttgaga ccataataac atcactaacc     720
agagacatca taacacacaa atttatatac ttgataaatc atgaatgcat agtgagaaaa     780
cttgatgaaa aacaggccac atttacattc ctggtcaact atgaaatgaa actattacac     840
aaagtaggaa gcactaaata taaaaaatat actgaataca acacaaaata tggcactttc     900
cctatgccaa tattcatcaa tcatgatggg ttcttagaat gcattggcat taagcctaca     960
```

```
aagcatactc ccataatata caagtatgat ctcaatccat aaatttcaac acaatattca    1020
cacaatctaa aacaacaact ctatgcataa ctatactcca tagtccagat ggagcctgaa    1080
aattatagta atttaaaatt aaggagagat ataagataga agatggggca aatacaaaga    1140
tggctcttag caaagtcaag ttgaatgata cactcaacaa agatcaactt ctgtcatcca    1200
gcaaatacac catccaacgg agcacaggag atagtattga tactcctaat tatgatgtgc    1260
agaaacacat caataagtta tgtggcatgt tattaatcac agaagatgct aatcataaat    1320
tcactgggtt aataggtatg ttatatgcga tgtctaggtt aggaagagaa gacaccataa    1380
aaatactcag agatgcggga tatcatgtaa agcaaatgg agtagatgta acaacacatc    1440
gtcaagacat taatggaaaa gaaatgaaat tgaagtgtt aacattggca agcttaacaa    1500
ctgaaattca aatcaacatt gagatagaat ctagaaaatc ctacaaaaaa atgctaaaag    1560
aaatgggaga ggtagctcca gaatacaggc atgactctcc tgattgtggg atgataatat    1620
tatgtatagc agcattagta ataactaaat tagcagcagg ggacagatct ggtcttacag    1680
ccgtgattag gagagctaat aatgtcctaa aaatgaaat gaaacgttac aaaggcttac    1740
tacccaagga catagccaac agcttctatg aagtgtttga aaaacatccc cactttatag    1800 atgttttgt tcattttggt atagcacaat cttctaccag aggtggcagt agagttgaag    1860 ggattttgc aggattgttt atgaatgcct atggtgcagg gcaagtgatg ttacggtggg    1920
gagtcttagc aaaatcagtt aaaaatatta tgttaggaca tgctagtgtg caagcagaaa    1980
tggaacaagt tgttgaggtt tatgaatatg cccaaaaatt gggtggtgaa gcaggattct    2040
accatatatt gaacaaccca aaagcatcat tattatcttt gactcaattt cctcacttct    2100
ccagtgtagt attaggcaat gctgctggcc taggcataat gggagagtac agaggtacac    2160
cgaggaatca agatctatat gatgcagcaa aggcatatgc tgaacaactc aaagaaaatg    2220
gtgtgattaa ctacagtgta ctagacttga cagcagaaga actagaggct atcaaacatc    2280
agcttaatcc aaaagataat gatgtagagc tttgagttaa taaaaaatgg ggcaaataaa    2340
tcatcatgga aaagtttgct cctgaattcc atggagaaga tgcaaacaac agggctacta    2400
aattcctaga atcaataaag ggcaaattca catcacccaa agatcccaag aaaaaagata    2460
gtatcatatc tgtcaactca atagatatag aagtaaccaa agaaagccct ataacatcaa    2520
attcaactat tatcaaccca caaatgaga cagatgatac tgcagggaac aagcccaatt    2580
atcaaagaaa acctctagta agtttcaaag aagaccctac accaagtgat aatccctttt    2640
ctaaactata caaagaaacc atagaaacat ttgataacaa tgaagaagaa tccagctatt    2700
catacgaaga aataaatgat cagacaaacg ataatataac agcaagatta gataggattg    2760
atgaaaaatt aagtgaaata ctaggaatgc ttcacacatt agtagtggca agtgcaggac    2820
ctacatctgc tcgggatggt ataagagatg ccatgattgg tttaagagaa gaaatgatag    2880
aaaaaatcag aactgaagca ttaatgacca atgacagatt agaagctatg gcaagactca    2940
ggaatgagga agtgaaaag atggcaaaag acacatcaga tgaagtgtct ctcaatccaa    3000
catcagagaa attgaacaac ctattggaag ggaatgatag tgacaatgat ctatcacttg    3060
aagatttctg attagttacc actcttcaca tcaacacaca ataccaacag aagaccaaca    3120
aactaaccaa cccaatcatc caaccaaaca tccatccgcc aatcagccaa acagccaaca    3180
aaacaaccag ccaatccaaa actaaccacc cggaaaaaat ctataatata gttacaaaaa    3240
aaggaaaggg tggggcaaat atggaaacat acgtgaacaa gcttcacgaa ggctccacat    3300
acacagctgc tgttcaatac aatgtcttag aaaaagacga tgaccctgca tcacttacaa    3360
```

```
tatgggtgcc catgttccaa tcatctatgc cagcagattt acttataaaa gaactagcta    3420
atgtcaacat actagtgaaa caaatatcca cacccaaggg accttcacta agagtcatga    3480
taaactcaag aagtgcagtg ctagcacaaa tgcccagcaa atttaccata tgcgctaatg    3540
tgtccttgga tgaaagaagc aaactagcat atgatgtaac cacaccctgt gaaatcaagg    3600
catgtagtct aacatgccta aaatcaaaaa atatgttgac tacagttaaa gatctcacta    3660
tgaagacact caaccctaca catgatatta ttgctttatg tgaatttgaa acatagtaa     3720 catcaaaaaa agtcataata ccaacatacc taagatccat cagtgtcaga aataaagatc    3780
tgaacacact tgaaaatata acaaccactg aattcaaaaa tgctatcaca aatgcaaaaa    3840
tcatccctta ctcaggatta ctattagtca tcacagtgac tgacaacaaa ggagcattca    3900
aatacataaa gccacaaagt caattcatag tagatcttgg agcttaccta gaaaaagaaa    3960
gtatatatta tgttaccaca aattggaagc acacagctac acgatttgca atcaaaccca    4020
tggaagatta acctttttcc tctacatcag tgtgttaatt catacaaact ttctacctac    4080
attcttcact tcaccatcac aatcacaaac actctgtggt tcaaccaatc aaacaaaact    4140
tatctgaagt cccagatcat cccaagtcat tgtttatcag atctagtact caaataagtt    4200
aataaaaaat atacacatgg ggcaaataat cattggagga aatccaacta atcacaatat    4260
ctgttaacat agacaagtcc acacaccata cagaatcaac caatggaaaa tacatccata    4320
acaatagaat tctcaagcaa attctggcct tactttacac taatacacat gatcacaaca    4380
ataatctctt tgctaatcat aatctccatc atgattgcaa tactaaacaa actttgtgaa    4440
tataacgtat tccataacaa aacctttgag ttaccaagag ctcgagtcaa cacatagcat    4500
tcatcaatcc aacagcccaa aacagtaacc ttgcatttaa aaatgaacaa cccctacctc    4560
tttacaacac ctcattaaca tcccaccatg caaaccacta tccatactat aaagtagtta    4620
attaaaaata gtcataacaa tgaactagga tatcaagact aacaataaca ttggggcaaa    4680
tgcaaacatg tccaaaaaca aggaccaacg caccgctaag acattagaaa ggacctggga    4740
cactctcaat catttattat tcatatcatc gtgcttatat aagttaaatc ttaaatctgt    4800
agcacaaatc acattatcca ttctggcaat gataatctca acttcactta taattgcagc    4860
catcatattc atagcctcgg caaaccacaa agtcacacca acaactgcaa tcatacaaga    4920
tgcaacaagc cagatcaaga acaccacccc aacatacctc acccagaatc ctcagcttgg    4980
aatcagtccc tctaatccgt ctgaaattac atcacaaatc accaccatac tagcttcaac    5040
aacaccagga gtcaagtcaa ccctgcaatc cacaacagtc aagaccaaaa acacaacaac    5100
aactcaaaca caacccagca agcccaccac aaaacaacgc caaaacaaac caccaagcaa    5160
acccaataat gatttcact tgaagtgtt caactttgta ccctgcagca tatgcagcaa    5220
caatccaacc tgctgggcta tctgcaaaag aataccaaac aaaaaaccag gaaagaaaac    5280
cactaccaag cccacaaaaa aaccaaccct caagacaacc aaaaaagatc ccaaacctca    5340
aaccactaaa tcaaaggaag tacccaccac caagcccaca gaagagccaa ccatcaacac    5400
caccaaaaca aacatcataa ctacactact caccctccaac accacaggaa atccagaact    5460
cacaagtcaa atggaaacct tccactcaac ttcctccgaa ggcaatccaa gcccttctca    5520
agtctctaca acatccgagt acccatcaca accttcatct ccacccaaca caccacgcca    5580
gtagttactt aaaaacatat tatcacaaaa agccatgacc aacttaaaca gaatcaaaat    5640
aaactctggg gcaaataaca atggagttgc taatcctcaa agcaaatgca attaccacaa    5700
```

```
tcctcactgc agtcacattt tgttttgctt ctggtcaaaa catcactgaa gaattttatc      5760
aatcaacatg cagtgcagtt agcaaaggct atcttagtgc tctgagaact ggttggtata      5820
ccagtgttat aactatagaa ttaagtaata tcaaggaaaa taagtgtaat ggaacagatg      5880
ctaaggtaaa attgataaaa caagaattag ataaatataa aaatgctgta acagaattgc      5940
agttgctcat gcaaagcaca ccaccaacaa acaatcgagc cagaagagaa ctaccaaggt      6000
ttatgaatta tacactcaac aatgccaaaa aaccaatgt aacattaagc aagaaaagga       6060
aaagaagatt tcttgttttt tgttaggtg ttggatctgc aatcgccagt ggcgttgctg       6120
tatctaaggt cctgcaccta gagggggaag tgaacaagat caaagtgct ctactatcca       6180 caaacaaggc tctagtcagc ttatcaaatg gagttagtgt cttaaccagc aaagtgttag      6240
acctcaaaaa ctatatagat aaacaattgt tacctattgt gaacaagcaa agctgcagca      6300
tatcaaatat agaaactgtg atagagttcc aacaaaagaa caacagacta ctagagatta     6360
ccagggaatt tagtgttaat gcaggtgtaa ctacacctgt aagcacttac atgttaacta     6420
atagtgaatt attgtcatta atcaatgata tgcctataac aaatgatcag aaaaagttaa    6480
tgtccaacaa tgttcaaata gttagacagc aaagttactc tatcatgtcc ataataaaag     6540
aggaagtctt agcatatgta gtacaattac cactatatgg tgtttatagat acaccctgtt    6600 ggaaactaca cacatccct ctatgtacaa ccaacacaaa agaagggtcc aacatctgtt     6660
taacaagaac tgacagagga tggtactgtg acaatgcagg atcagtatct ttcttcccac     6720
aagctgaaac atgtaaagtt caatcaaatc gagtatttg tgacacaatg aacagtttaa     6780
cattaccaag tgaaataaat ctctgcaatg ttgacatatt caaccccaaa tatgattgta     6840
aaattatgac ttcaaaaaca gatgtaagca gctccgttat cacatctcta ggagccattg     6900
tgtcatgcta tggcaaaact aaatgtacag catccaataa aaatcgtgga atcataaaga     6960
cattttctaa cgggtgcgat tatgtatcaa ataaagggat ggacactgtg tctgtaggta     7020
acacattata ttatgtaaat aagcaagaag gtaaaagtct ctatgtaaaa ggtgaaccaa     7080
taataaattt ctatgaccca ttagtattcc cctctgatga atttgatgca tcaatatctc     7140
aagtcaacga gaagattaac cagagcctag cattattcg taaatccgat gaattattac     7200
ataatgtaaa tgctggtaaa tccaccacaa atatcatgat aactactata attatagtga    7260
ttatagtaat attgttatca ttaattgctg ttggactgct cttatactgt aaggccagaa     7320
gcacaccagt cacactaagc aaagatcaac tgagtggtat aaataatatt gcatttagta    7380
actaaataaa aatagcacct aatcatgttc ttacaatggt ttactatctg ctcatagaca    7440
acccatctgt cattggattt tcttaaaatc tgaacttcat cgaaactctc atctataaac     7500
catctcactt acactatttta agtagattcc tagtttatag ttatataaaa cacaattgaa    7560
tgccagatta acttaccatc tgtaaaaatg aaaactgggg caaatatgtc acgaaggaat    7620
ccttgcaaat ttgaaattcg aggtcattgc ttaaatggta agaggtgtca ttttagtcat     7680
aattattttg aatggccacc ccatgcactg cttgtaagac aaaactttat gttaaacaga    7740
atacttaagt ctatggataa agtatagat accttatcag aaataagtgg agctgcagag     7800
ttggacagaa cagaagagta tgctcttggt gtagttggag tgctagagag ttatatagga    7860
tcaataaaca atataactaa acaatcagca tgtgttgcca tgagcaaact cctcactgaa    7920
ctcaatagtg atgatatcaa aaagctgagg acaatgaag agctaaattc acccaagata    7980
agagtgtaca atactgtcat atcatatatt gaaagcaaca ggaaaaacaa taaacaaact     8040
atccatctgt taaaaagatt gccagcagac gtattgaaga aaaccatcaa aaacacattg    8100
```

```
gatatccata agagcataac catcaacaac ccaaaagaat caactgttag tgatacaaat    8160
gaccatgcca aaataatga tactacctga caaatatcct tgtagtataa cttccatact    8220
aataacaagt agatgtagag ttactatgta taatcaaaag aacacactat atttcaatca    8280
aaacaaccca aataaccata tgtactcacc gaatcaaaca ttcaatgaaa tccattggac    8340
ctctcaagaa ttgattgaca caattcaaat ttttctacaa catctaggta ttattgagga    8400
tatatataca atatatatat tagtgtcata acactcaatt ctaacactca ccacatcgtt    8460
acattattaa ttcaaacaat tcaagttgtg ggacaaaatg gatcccatta ttaatggaaa    8520
ttctgctaat gtttatctaa ccgatagtta tttaaaaggt gttatctctt tctcagagtg    8580
taatgcttta ggaagttaca tattcaatgg tccttatctc aaaaatgatt ataccaactt    8640
aattagtaga caaaatccat taatagaaca catgaatcta agaaactaa atataacaca    8700 gtccttaata tctaagtatc ataaaggtga aataaaatta gaagaaccta cttattttca    8760
gtcattactt atgacataca agagtatgac ctcgtcagaa cagattgcta ccactaattt    8820
acttaaaaag ataataagaa gagctataga aataagtgat gtcaaagtct atgctatatt    8880
gaataaacta gggcttaaag aaaaggacaa gattaaatcc aacaatggac aagatgaaga    8940
caactcagtt attacgacca taatcaaaga tgatatactt tcagctgtta aagataatca    9000
atctcatctt aaagcagaca aaaatcactc tacaaaacaa aaagacacaa tcaaaacaac    9060
actcttgaag aaattgatgt gttcaatgca acatcctcca tcatggttaa tacattggtt    9120
taacttatac acaaaattaa acaacatatt aacacagtat cgatcaaatg aggtaaaaaa    9180
ccatgggttt acattgatag ataatcaaac tcttagtgga tttcaattta ttttgaacca    9240
atatggttgt atagtttatc ataaggaact caaaagaatt actgtgacaa cctataatca    9300
attcttgaca tggaaagata ttagccttag tagattaaat gtttgtttaa ttacatggat    9360
tagtaactgc ttgaacacat taaataaaag cttaggctta agatgcggat tcaataatgt    9420
tatcttgaca caactattcc tttatggaga ttgtatacta aagctatttc acaatgaggg    9480
gttctacata ataaaagagg tagagggatt tattatgtct ctaattttaa atataacaga    9540
agaagatcaa ttcagaaaac gattttataa tagtatgctc aacaacatca cagatgctgc    9600
taataaagct cagaaaaatc tgctatcaag agtatgtcat acattattag ataagacagt    9660
gtccgataat ataataaatg gcagatggat aattctatta agtaagttcc ttaaattaat    9720
taagcttgca ggtgacaata accttaacaa tctgagtgaa ctatattttt tgttcagaat    9780
atttggacac ccaatggtag atgaaagaca agccatggat gctgttaaaa ttaattgcaa    9840
tgagaccaaa ttttacttgt taagcagtct gagtatgtta agaggtgcct ttatatatag    9900
aattataaaa gggtttgtaa ataattacaa cagatggcct actttaagaa atgctattgt    9960 tttacccctta agatggttaa cttactataa actaaacact tatccttctt gttggaact   10020 tacagaaaga gatttgattg tgttatcagg actacgtttc tatcgtgagt ttcggttgcc   10080
taaaaaagtg gatcttgaaa tgattataaa tgataaagct atatcacctc ctaaaaattt   10140
gatatggact agtttcccta gaaattacat gccatcacac atacaaaact atatagaaca   10200
tgaaaaatta aaattttccg agagtgataa atcaagaaga gtattagagt attatttaag   10260
agataacaaa ttcaatgaat gtgatttata caactgtgta gttaatcaaa gttatctcaa   10320 caacccctaat catgtggtat cattgacagg caaagaaaga gaactcagtg taggtagaat   10380
gtttgcaatg caaccgggaa tgttcagaca ggttcaaata ttggcagaga aaatgatagc   10440
```

```
tgaaaacatt ttacaattct ttcctgaaag tcttacaaga tatggtgatc tagaactaca    10500
aaaaatatta gaattgaaag caggaataag taacaaatca aatcgctaca atgataatta    10560
caacaattac attagtaagt gctctatcat cacagatctc agcaaattca atcaagcatt    10620
tcgatatgaa acgtcatgta tttgtagtga tgtgctggat gaactgcatg gtgtacaatc    10680
tctattttcc tggttacatt taactattcc tcatgtcaca ataatatgca catataggca    10740 tgcaccccc tataggag atcatattgt agatcttaac aatgtagatg aacaaagtgg      10800
attatataga tatcacatgg gtggcatcga agggtggtgt caaaaactgt ggaccataga    10860
agctatatca ctattggatc taatatctct caaagggaaa ttctcaatta ctgctttaat    10920
taatggtgac aatcaatcaa tagatataag caaaccaatc agactcatgg aaggtcaaac    10980
tcatgctcaa gcagattatt tgctagcatt aaatagcctt aaattactgt ataaagagta    11040
tgcaggcata ggccacaaat taaaaggaac tgagacttat atatcacgag atatgcaatt    11100
tatgagtaaa acaattcaac ataacggtgt atattaccca gctagtataa agaaagtcct    11160
aagagtggga ccgtggataa acactatact tgatgatttc aaagtgagtc tagaatctat    11220
aggtagtttg acacaagaat tagaatatag aggtgaaagt ctattatgca gtttaatatt    11280
tagaaatgta tggttatata atcagattgc tctacaatta aaaaatcatg cattatgtaa    11340
caataaacta tatttggaca tattaaaggt tctgaaacac ttaaaaacct tttttaatct    11400
tgataatatt gatacagcat taacattgta tatgaattta cccatgttat ttggtggtgg    11460
tgatcccaac ttgttatatc gaagtttcta tagaagaact cctgacttcc tcacagaggc    11520
tatagttcac tctgtgttca tacttagtta ttatacaaac catgacttaa aagataaact    11580
tcaagatctg tcagatgata gattgaataa gttcttaaca tgcataatca cgtttgacaa    11640
aaaccctaat gctgaattcg taacattgat gagagatcct caagctttag ggtctgagag    11700
acaagctaaa attactagcg aaatcaatag actggcagtt acagaggttt tgagtacagc    11760
tccaaacaaa atattctcca aaagtgcaca acattatact actacagaga tagatctaaa    11820
tgatattatg caaaatatag aacctacata tcctcatggg ctaagagttg tttatgaaag    11880
tttacccttt tataaagcag agaaaatagt aaatcttata tcaggtacaa aatctataac    11940
taacatactg gaaaaaactt ctgccataga cttaacagat attgatagag ccactgagat    12000
gatgaggaaa aacataactt tgcttataag gatacttcca ttggattgta acagagataa    12060
aagagagata ttgagtatgg aaaacctaag tattactgaa ttaagcaaat atgttaggga    12120
aagatcttgg tctttatcca atatagttgg tgttacatca cccagtatca tgtatacaat    12180
ggacatcaaa tatactacaa gcactatatc tagtggcata attatagaga aatataatgt    12240
taacagttta acacgtggtg agagaggacc cactaaacca tgggttggtt catctacaca    12300
agagaaaaaa acaatgccag tttataatag acaagtctta accaaaaaac agagagatca    12360
aatagatcta ttagcaaaat tggattgggt gtatgcatct atagataaca aggatgaatt    12420
catggaagaa ctcagcatag gaaccttggg gttaacatat gaaaaggcca agaaattatt    12480
tccacaatat ttaagtgtca attatttgca tcgccttaca gtcagtagta gaccatgtga    12540
attccctgca tcaataccag cttatagaac aacaaattat cactttgaca ctagccctat    12600
taatcgcata ttaacagaaa gtatggtga tgaagatatt gacatagtat ccaaaactg    12660 tataagcttt ggcctagtt taatgtcagt agtagaacaa tttactaatg tatgtcctaa    12720
cagaattatt ctcataccta agcttaatga gatacatttg atgaacctc ccatattcac    12780 aggtgatgtt gatattcaca gttaaaaca agtgatacaa aaacagcata tgttttttacc    12840
```

```
agacaaaata agtttgactc aatatgtgga attattctta agtaataaaa cactcaaatc    12900
tggatctcat gttaattcta atttaatatt ggcacataaa atatctgact attttcataa    12960
tacttacatt ttaagtacta atttagctgg acattggatt ctgattatac aacttatgaa    13020
agattctaaa ggtattttttg aaaaagattg gggagaggga tatataactg atcatatgtt   13080
tattaatttg aaagttttct tcaatgctta taagacctat ctcttgtgtt ttcataaagg    13140
ttatggcaaa gcaaagctgg agtgtgatat gaacacttca gatcttctat gtgtattgga    13200
attaatagac agtagttatt ggaagtctat gtctaaggta ttttttagaac aaaaagttat   13260 caaatacatt cttagccaag atgcaagttt acatagagta aaaggatgtc atagcttcaa    13320
attatggttt cttaaacgtc ttaatgtagc agaattcaca gtttgccctt gggttgttaa    13380
catagattat catccaacac atatgaaagc aatattaact tatatagatc ttgttagaat    13440
gggattgata aatatagata gaatacacat taaaaataaa cacaaattca atgatgaatt    13500
ttatacttct aatctcttct acattaatta taacttctca gataatactc atctattaac    13560
taaacatata aggattgcta attctgaatt agaaaataat tacaacaaat tatatcatcc    13620
tacaccagaa accctagaga atatactagc caatccgatt aaaagtaatg acaaaaagac    13680
actgaatgac tattgtatag gtaaaaatgt tgactcaata atgttaccat tgttatctaa    13740
taagaagctt attaaatcgt ctgcaatgat tagaaccaat tacagcaaac aagatttgta    13800
taatttattc cctatggttg tgattgatag aattatagat cattcaggca atacagccaa    13860
atccaaccaa ctttcacacta ctacttccca ccaaatatct ttagtgcaca atagcacatc   13920
actttactgc atgcttcctt ggcatcatat taatagattc aattttgtat ttagttctac    13980
aggttgtaaa attagtatag agtatatttt aaaagatctt aaaattaaag atcccaattg    14040
tatagcattc ataggtgaag gagcagggaa tttattattg cgtacagtag tggaacttca    14100
tcctgacata agatatattt acagaagtct gaaagattgc aatgatcata gtttacctat    14160
tgagttttta aggctgtaca atggacatat caacattgat tatggtgaaa atttgaccat    14220
tcctgctaca gatgcaacca acaacattca ttggtcttat ttacatataa agtttgctga    14280
acctatcagt ctttttgtct gtgatgccga attgtctgta acagtcaact ggagtaaaat    14340
tataatagaa tggagcaagc atgtaagaaa gtgcaagtac tgttcctcag ttaataaatg    14400
tatgttaata gtaaaatatc atgctcaaga tgatattgat ttcaaattag acaatataac    14460
tatattaaaa acttatgtat gcttaggcag taagttaaag ggatcggagg tttacttagt    14520
ccttacaata ggtcctgcga atatattccc agtatttaat gtagtacaaa atgctaaatt    14580
gatactatca agaaccaaaa atttcatcat gcctaagaaa gctgataaag agtctattga    14640
tgcaaatatt aaaagtttga tacccttttct ttgttaccct ataacaaaaa aaggaattaa   14700
tactgcattg tcaaaactaa agagtgttgt tagtggagat atactatcat attctatagc    14760
tggacgtaat gaagttttca gcaataaaact tataaatcat aagcatatga acatcttaaa   14820
atggttcaat catgttttaa atttcagatc aacagaacta aactataacc atttatatat    14880
ggtagaatct acatatcctt acctaagtga attgttaaac agcttgacaa ccaatgaact    14940
taaaaaactg attaaaatca caggtagtct gttatacaac tttcataatg aataatgaat    15000
aaagatctta taataaaaat tcccatagct atacactaac actgtattca attatagtta    15060
ttaaaaatta aaaatcatat aattttttaa ataacttttta gtgaactaat cctaaagtta   15120
tcattttaat cttggaggaa taaatttaaa ccctaatcta attggtttat atgtgtatta    15180
```

-continued

```
actaaattac gagatattag tttttgacac ttttttctc gt                 15222

<210> SEQ ID NO 3
<211> LENGTH: 15191
<212> TYPE: DNA
<213> ORGANISM: Human respiratory syncytial virus

<400> SEQUENCE: 3
gaaaaaatgc gtacaacaaa cttgcgtaaa ccaaaaaaat ggggcaaata agaatttgat      60
aagtaccact taaatttaac tcccttggtt agagatgggc agcaattcgt tgagtatgat     120
aaaagttaga ttacaaaatt tgttggacaa tgatgaagta gcattgttaa aaataacatg     180
ctatactgac aaattaatac atttaactaa tgctttggct aaggcagtga tacatacaat     240
caaattgaat ggcattgtgt ttgtgcatgt tattacaagt agtgatattt gccctaataa     300
taatattgta gtaaaatcca atttcacaac aatgccagcg ctacaaaatg gaggttatat     360
atgggaaatg atggaattaa cacattgctc tcaacctaat ggtctaatag atgacaattg     420
tgaaattaaa ttctccaaaa aactaagtga ttcaacaatg accaattata tgaatcaatt     480
atctgaatta cttggatttg atcttaatcc ataaattata attaatatca actagcaaat     540
caatgtcact agcaccatta gttaatataa aacttaacag aagacaaaaa tggggcaaat     600
aaatcaactc agccaaccca accatggaca caacccacaa tgataccaca ccacaaagac     660
tgatgatcac agacatgaga ccgttgtcac ttgagactac aataacatca ctaaccagag     720
acatcataac acacagattt atatacttaa taaatcatga atgcatagtg agaaaacttg     780
atgaaagaca ggccacattt acattcctgg tcaactatga aatgaaacta ttgcacaaag     840
taggaagcac taaatataaa aaatatactg aatacaacac aaaatatggc actttcccta     900
tgccgatatt catcaatcat gatgggttct tagaatgcat tggcattaag cctacaaagc     960
atactcccat aatatacaag tatgatctca atccatgaat ttcaacacaa gattcacaca    1020
atccaaaaca acaactttat gcataactac actccatagt ccagatggag cctgaaaatt    1080
atagtaattt aaaattaagg agagacataa gatagaagat ggggcaaata caaagatggc    1140
tcttagcaaa gtcaagttga atgatacact caacaaagat caacttctgt catctagcaa    1200
atacaccatc caacggagca caggagatag tattgatact cctaattatg atgtgcagaa    1260
acacatcaat aagttatgtg gcatgttatt aatcacagaa gatgctaatc ataaattcac    1320
tgggttaata ggtatgttat atgctatgtc taggttagga agagaagaca ccataaaaat    1380
actcagagat gcgggatatc atgtaaaagc aaatggagta gatgtaacaa cacatcgtca    1440
agacatcaat gggaaagaaa tgaaatttga agtgttaaca ttggcaagct taacaactga    1500
aattcaaatc aacattgaga tagaatctag aaaatcctac aaaaaaatgc taaaagaaat    1560
gggagaggta gctccagaat acaggcatga ttctcctgat tgtgggatga taatattatg    1620
tatagcagca ttagtaataa ccaaattggc agcaggggat agatctggtc ttacagccgt    1680
gattaggaga gctaataatg tcctaaaaaa tgaaatgaaa cgttacaaag gcttactacc    1740
caaggatata gccaacagct tctatgaagt gtttgaaaaa catccccact ttatagatgt    1800
ttttgttcat tttggtatag cacaatcttc caccagaggt ggcagtagag ttgaagggat    1860
ttttgcagga ttgtttatga atgcctatgg tgcagggcaa gtaatgctac ggtggggagt    1920
cttagcaaaa tcagttaaaa atattatgtt aggacatgct agtgtgcaag cagaaatgga    1980
acaagttgtt gaggtttatg aatatgccca aaaattgggt ggagaagcag gattctacca    2040
tatattgaac aacccaaaag catcattatt atctttgact caatttcctc acttttccag    2100
```

```
tgtagtatta ggcaatgctg ctggcctagg cataatggga gagtacagag gtacaccgag    2160
gaatcaagat ctatatgatg cagcaaaggc atatgctgaa caactcaaag aaaatggtgt    2220
gattaactac agtgtattag acttgacagc agaagaacta gaggctatca acatcagct    2280 taatccaaaa gataatgatg tagagctttg agttaataaa aaaatggggc aaataaatca    2340
tcatggaaaa gtttgctcct gaattccatg gagaagatgc aaacaacagg gctactaaat    2400
tcctagaatc aataaagggc aaattcacat cacctaaaga tcccaagaaa aaagatagta    2460
tcatatctgt caactcaata gatatagaag taaccaaaga aagccctata acatcaaatt    2520
caaccattat taacccaaca aatgagacag atgataatgc agggaacaag cccaattatc    2580
aaagaaaacc tctagtaagt ttcaaagaag acccatacc aagtgataat ccctttcaa    2640 aactatacaa agaaaccata gagacatttg ataacaatga agaagaatct agctattcat    2700
atgaagaaat aaatgatcag acgaacgata atataactgc aagattagat aggattgatg    2760
aaaaattaag tgaaatacta ggaatgcttc acacattagt agtagcaagt gcaggaccta    2820
catctgctag ggatggtata agagatgcca tggttggttt aagagaagaa atgatagaaa    2880
aaatcagaac tgaagcatta atgaccaatg acagattaga agctatggca agactcagga    2940
atgaggaaag tgaaaagatg gcaaaagaca catcagatga agtgtctctc aatccaacat    3000
cagagaaatt gaacaacctg ttggaaggga atgatagtga caatgatcta tcacttgaag    3060
atttctgatt agttacaaat ctgcacttca acacacaaca ccaacagaag accaacaaac    3120
aaaccaaccc actcatccaa ccaaacatcc atccgccaat cagccaaaca gccaacaaaa    3180
caaccagcca atccaaaacc agccacctgg aaaaaatcga caatatagtt acaaaaaaag    3240
aaaagggtgg ggcaaatatg gaaacatacg tgaacaagct tcacgaaggc tccacataca    3300
cagctgctgt tcaatacaat gtcctagaaa aagacgatga ccctgcatca cttacaatat    3360
gggtgcccat gttccaatca tctatgccag cagatttact tataaaagaa ctagctaatg    3420
tcaacatact agtgaaacaa atatccacac ccaagggacc ttcactaaga gtcatgataa    3480
actcaagaag tgcattgcta gcacaaatgc ccagcaaatt taccatatgt gctaatgtgt    3540
ccttggatga aagaagcaaa ctggcatatg atgtaaccac accctgtgaa atcaaggcat    3600
gtagtctaac atgcctaaaa tcaaaaaata tgttaactac agttaaagat ctcactatga    3660
agacactcaa ccccacacat gatattattg ctttatgtga atttgaaaac atagtaacat    3720
caaaaaaagt cataatacca acatacctaa gatccatcag tgtcagaaat aaagatctga    3780
acacacttga aaatataaca accactgaat tcaaaaatgc catcacaaat gcaaaaatca    3840
tcccttactc aggattacta ttagtcatca cagtgactga caacaaagga gcattcaaat    3900
acataaagcc gcaaagtcaa ttcatagtag atcttggagc ttacctagaa aaagaaagta    3960
tatattatgt taccacaaat tggaagcaca cagctacacg atttgcaatc aaacccatgg    4020
aagattaacc tttttcctcc acatcagtga gtcaattcat acaaactttc tacctacatt    4080
cttcacttca ccattacaat cacaaacact ctgtggttca accaatcaaa caaaacttat    4140
ctgaagtctc agatcatccc aagtcattgt tcatcagatc tagtaatcaa ataagttaat    4200
aaaaaatata cacatggggc aaataatcat tggaggaaat ccaactaatc acaatatctg    4260
ttaacataga caagtcaaca caccagacag aatcaaccaa tggaaaatac atccataaca    4320
atagaattct caagcaaatt ctggccttac tttacactaa tacacatgat cacaacaata    4380
atctctttgc taatcataat ctccatcatg actgcaatac taaacaaact tgtgaatat    4440
```

```
aacgtattcc ataacaaaac ctttgagtta ccaagagctc gagtcaacac atagcattca   4500
tcaatctaat agctcaaaat agtaaccttg catttaaaag tgaacaaccc ccacctcttt   4560
acaacacctc attaacatcc caccatgcaa accaccatcc atactataaa gtagttaatt   4620
aaaaatagtc ataacaatga actaggatat caagactaac aataacgttg gggcaaatgc   4680
aaacatgtcc aaaaacaagg accaacgcac cgctaagaca ctagaaaaga cctgggacac   4740
tctcaatcat ttattattca tatcatcgtg cttatataag ttaaatctta aatctatagc   4800
acaaatcaca ttatccattc tggcaatgat aatctcaact tcacttataa ttacagccat   4860
catattcata gcctcggcaa accacaaagt cacactaaca actgcaatca tacaagatgc   4920
aacaagccag atcaagaaca caaccccaac atacctcact caggatcctc agcttggaat   4980
cagcttctcc aatctgtctg aaattacatc acaaaccacc accatactag cttcaacaac   5040
accaggagtc aagtcaaacc tgcaacccac aacagtcaag actaaaaaca caacaacaac   5100
ccaaacacaa cccagcaagc ccactacaaa acaacgccaa aacaaccac caaacaaacc   5160 caataatgat tttcacttcg aagtgtttaa ctttgtaccc tgcagcatat gcagcaacaa   5220
tccaacctgc tgggctatct gcaaaagaat accaaacaaa aaaccaggaa agaaaaccac   5280
caccaagcct acaaaaaaac caaccttcaa gacaaccaaa aaagatctca aacctcaaac   5340
cactaaacca aaggaagtac ccaccaccaa gcccacagaa gagccaacca tcaacaccac   5400
caaaacaaac atcacaacta cactgctcac caacaacacc acaggaaatc caaaactcac   5460
aagtcaaatg gaaaccttcc actcaacctc ctccgaaggc aatctaagcc cttctcaagt   5520
ctccacaaca tccgagcacc catcacaacc ctcatctcca cccaacacaa cacgccagta   5580
gttattaaaa aacatattat cacaaaggc catgaccaac tcaaacagaa tcaaaataaa   5640
ctctggggca ataacaatg gagttgccaa tcctcaaagc aaatgcaatt accacaatcc   5700
tcgctgcagt cacattttgc tttgcttcta gtcaaaacat cactgaagaa ttttatcaat   5760
caacatgcag tgcagttagc aaaggctatc ttagtgctct aagaactggt tggtatacta   5820
gtgttataac tatagaatta agtaatatca agaaaaataa gtgtaatgga acagatgcta   5880
aggtaaaatt gatgaaacaa gaattagata aatataaaaa tgctgtaaca gaattgcagt   5940
tgctcatgca aagcacacca gcagcaaaca atcgagccag aagagaacta ccaaggttta   6000
tgaattatac actcaacaat accaaaaaaa ccaatgtaac attaagcaag aaaaggaaaa   6060
gaagatttct tggttttttg ttaggtgttg atctgcaat cgccagtggc attgctgtat   6120
ctaaggtcct gcacttagaa ggagaagtga acaagatcaa aagtgctcta ctatccacaa   6180
acaaggccgt agtcagctta tcaaatggag ttagtgtctt aaccagcaga gtgttagacc   6240
tcaaaaacta tatagataaa caattgttac ctattgtgaa taagcaaagc tgcagaatat   6300
caaatataga aactgtgata gagttccaac aaaagaacaa cagactacta gagattacca   6360
gggaatttag tgttaatgca ggtgtaacta cacctgtaag cacttacatg ttaactaata   6420
gtgaattatt gtcattaatc aatgatatgc ctataacaaa tgatcagaaa aagttaatgt   6480
ccaacaatgt tcaaatagtt agacagcaaa gttactctat catgtccata ataaaagagg   6540
aagtcttagc atatgtagta caattaccac tatatggtgt gatagataca ccttgttgga   6600
aattacacac atcccctcta tgtacaacca acacaaaaga agggtcaaac atctgtttaa   6660
caagaactga cagaggatgg tactgtgaca atgcaggatc agtatctttc ttcccacaag   6720
ctgaaaaatg taaagttcaa tcgatcgag tattttgtga cacaatgtac agtttaacat   6780
taccaagtga agtaaatctc tgcaatgttg acatattcaa tcccaaatat gattgtaaaa   6840
```

```
ttatgacttc aaaaacagat gtaagcagct ccgttatcac atctctagga gccattgtgt    6900
catgctatgg caaaactaaa tgtacagcat ccaataaaaa tcgtggaatc ataaagacat    6960
tttctaacgg gtgtgattat gtatcaaata aagggtgga cactgtgtct gtaggtaaca     7020
cattatatta tgtaaataag caagaaggca aaagtctcta tgtaaaaggt gaaccaataa    7080
taaatttcta tgacccatta gtattcccct ctgatgaatt tgatgcatca atatctcaag    7140
tcaatgagaa gattaaccag agtttagcat ttattcgtaa atccgatgaa ttattacata    7200
atgtaaatgc tggtaaatca accacaaata tcatgataac tactataatt atagtgatta    7260
tagtaatatt gttatcatta attgctgttg gactgctcct atactgtaag gccagaagca    7320
caccaatcac actaagcaag gatcaactga gtggtataaa taatattgca tttagtaact    7380
gaataaaaat agcacctaat catgttctta caatggttta ctatctgctc atagacaacc    7440
catctatcat tggattttct aaaatctga acttcatcga aactcttatc tataaaccat     7500
ctcacttaca ctatttaagt agattcctag tttatagtta tataaaacac aattgaatac    7560
cagattaact tactatctgt aaaaatgaga actggggcaa atatgtcacg aaggaatcct    7620
tgcaaatttg aaattcgagg tcattgcttg aatggtaaga gatgtcattt tagtcataat    7680
tattttgaat ggccacccca tgcactgctc gtaagacaaa actttatgtt aaacagaata    7740
cttaagtcta tggataaaag tatagatacc ttatcagaaa taagtggagc tgcagagttg    7800
gacagaacag aagagtatgc tcttggtgta gttggagtgc tagagagtta tataggatca    7860
ataaataata taactaaaca atcagcatgt gttgccatga gcaaactcct cactgaactc    7920
aatagtgatg atatcaaaaa actgagagac aatgaagagc taaattcacc caagataaga    7980
gtgtacaata ctgtcatatc atatattgaa agcaacagga aaacaataa acaaactatc     8040
catctgttaa aaagattgcc agcagacgta ttgaagaaaa ccatcaaaaa cacattggat    8100
atccacaaga gcataaccat caacaaccca aaagaattaa ctgttagtga tacaaatgac    8160
catgccaaaa ataatgatac tacctgacaa atatccttgt agtataactt ccatactaat    8220
aacaagtaga tgtagagtca ctatgtataa tcgaaagaac acactatatt tcaatcaaaa    8280
caacccaaat aaccatatgt actcaccgaa tcaaacattc aatgaaatcc attggacctc    8340
acaagacttg attgacacaa ttcaaaattt tctacagcat ctaggtgtta ttgaggatat    8400
atatacaata tatatattag tgtcataaca ctcaatccta atactgacca tatcgttgaa    8460
ttattaattc aaataattca agctgtggga caaatggat cccattatta atggaaattc     8520
tgctaatgtt tatctaaccg atagttattt aaaaggtgtt atctctttct cagagtgtaa    8580
tgctttagga agttacatat tcaatggtcc ttatctcaaa aatgattata ccaacttaat    8640
tagtagacaa aatccattaa tagaacacat gaatctaaag aaactaaata taacacagtc    8700
cttaatatct aagtatcata aaggtgaaat aaaattagaa gagcctactt attttcagtc    8760
attacttatg acatacaaga gtatgacctc gttggaacag attgctacca ctaattact    8820
taaaagata ataagaagag ctatagaaat aagtgatgtc aaagtctatg ctatattgaa     8880
taaactaggg cttaaagaaa aggacaagat taaatccaac aatggacagg atgaagacaa    8940
ctcagttatt acgaccataa tcaaagatga tatactttca gctgttaagg ataatcaatc    9000
tcatcttaaa gcagacaaaa atcactctac aaaacaaaaa gacacaatca aaacaacact    9060
cttgaagaaa ttaatgtgtt caatgcagca tcctccatca tggttaatac attggtttaa    9120
tttatacaca aaattaaaca acatattaac acagtatcga tcaaatgagg ttaaaaacca    9180
```

```
tgggtttata ttgatagata atcaaactct tagtggattt caatttattt tgaatcaata    9240
tggttgtata gtttatcata aggaactcaa aagaattact gtgacaacct ataatcaatt    9300
cttgacatgg aaagatatta gccttagtag attaaatgtt tgtttaatta catggattag    9360
taactgcttg aacacattaa ataaaagctt aggcttaaga tgcggattca ataatgttat    9420
cttgacacaa ctattccttt atggagattg tatactaaag ctatttcaca atgaggggtt    9480
ctacataata aaagaggtag agggatttat tatgtctcta attttaaata taacagaaga    9540
agatcaattc agaaaacgat tttataatag tatgctcaac aacatcacag atgctgctaa    9600
taaagctcag aaaaatctgc tatcaagagt atgtcataca ttattagata agacagtatc    9660
cgataatata ataaatggca gatggataat tctattaagt aagttcctta aattaattaa    9720
gcttgcaggt gacaataacc ttaacaatct gagtgaacta tattttttgt tcagaatatt    9780
tggacaccca atggtagatg aaagacaagc catggatgct gttaaagtta attgcaatga    9840
gaccaaattt tacttgttaa gcagtttgag tatgttaaga ggtgccttta tatatagaat    9900
tataaaaggg tttgtaaata attacaacag atggcctact ttaagaaatg ctattgtttt    9960
acccttaaga tggttaactt actataaact aaacacttat ccttctttgt tggaacttac   10020
agaaagagat ttgattgtgt tatcaggact acgtttctat cgtgagtttc ggttgcctaa   10080
aaaagtggat cttgaaatga ttataaatga taaagctata tcacccccta aaaatttgat   10140
atggactagt ttccctagaa attatatgcc gtcacacata caaaactata tagaacatga   10200
aaaattaaaa ttttccgaga gtgataaatc aagaagagta ttagagtatt atttaagaga   10260
taacaaattc aatgaatgtg atttatacaa ctgtgtagtt aatcaaagtt atctcaacaa   10320
ccctaatcat gtggtatcat tgacaggcaa agaaagagaa ctcagtgtag gtagaatgtt   10380
tgcaatgcaa ccgggaatgt tcagacaggt tcaaatattg gcagagaaaa tgatagctga   10440
aaacatttta caattctttc ctgaaagtct tacaagatat ggtgatctag aactacaaaa   10500
aatattagaa ttgaaagcag gaataagtaa caaatcaaat cgctacaatg ataattacaa   10560
caattacatt agtaagtgct ctatcatcac agatctcagc aaattcaatc aagcatttcg   10620
atatgaaacg tcatgtattt gtagtgatgt gctggatgaa ctgcatggtg tacaatctct   10680
attttcctgg ttacatttaa ctattcctca tgtcacaata atatgcacat ataggcatgc   10740
acccccctat ataagagatc atattgtaga tcttaacaat gtagatgaac aaagtggatt   10800
atatagatat cacatgggtg gtattgaagg gtggtgtcaa aaactatgga ccatagaagc   10860
tatatcacta ttggatctaa tatctctcaa agggaaattc tcaattactg ctttaattaa   10920
tggtgacaat caatcaatag atataagcaa accagtcaga ctcatggaag gtcaaactca   10980
tgctcaagca gattatttgc tagcattaaa tagccttaaa ttactgtata aagagtatgc   11040
aggcataggt cacaaattaa aaggaactga gacttatata tcacgagata tgcaatttat   11100
gagtaaaaca attcaacata cggtgtata ttaccctgct agtataaaga agtcctaag    11160
agtgggaccg tggataaaca ctatacttga tgatttcaaa gtgagtctag aatctatagg   11220
tagtttgaca caagaattag aatatagagg tgaaagtcta ttatgcagtt taatatttag   11280
aaatgtatgg ttatataatc aaattgctct acaattaaaa aatcatgcgt tatgtaacaa   11340
taaattatat ttggacatat taaaggttct gaaacactta aaaaccttt ttaatcttga   11400
taatattgat acagcattaa cattgtatat gaatttaccc atgttatttg gtggtggtga   11460
tcccaacttg ttatatcgaa gtttctatag aagaactcct gatttcctca cagaggctat   11520
agttcactct gtgttcatac ttagttatta tacaaaccat gacttaaaag ataaacttca   11580
```

```
agatttgtca gatgatagat tgaataagtt cttaacatgc ataatcacgt ttgacaaaaa   11640
ccctaatgct gaattcgtaa cattgatgag agatcctcaa gctttagggt ctgagagaca   11700
agctaaaatt actagtgaaa tcaatagact ggcagttaca gaggttttga gtacagctcc   11760
aaacaaaata ttctccaaaa gtgcacaaca ttataccact acagagatag atctaaatga   11820
tattatgcaa aatatagaac ctacatatcc tcacgggcta agagttgttt atgaaagttt   11880
acccttttat aaagcagaga aaatagtaaa tcttatatca ggtacaaaat ctataactaa   11940
catactggaa aagacttctg ccatagactt aacagatatt gatagagcca ctgagatgat   12000
gaggaaaaac ataactttgc ttataaggat acttccattg gattgtaaca gagataaaag   12060
agaaatattg agtatggaaa acctaagtat tactgaatta agcaaatatg ttagggaaag   12120
atcttggtct ttatccaata tagttggtgt tacatcaccc agtatcatgt atacaatgga   12180
catcaaatat acaacaagca ctatagctag tggcataatt atagagaaat ataatgttaa   12240
cagtttaaca cgtggtgaga gaggaccaac taaaccatgg gttggttcat ctacacaaga   12300
gaaaaaaaca atgccagttt ataatagaca agttttaacc aaaaaacaaa gagatcaaat   12360
agatctatta gcaaaattgg attgggtgta tgcatctata gataacaagg atgaattcat   12420
ggaagaactc agcataggaa cccttgggtt aacatatgaa aaggccaaaa aattatttcc   12480
acaatattta agtgtcaact atttgcatcg ccttacagtc agtagtagac catgtgaatt   12540
ccctgcatca ataccagctt atagaacaac aaattatcac tttgacacta gcccctattaa   12600 tcgcatatta acagaaaagt atggtgatga agatattgac atagtattcc aaaactgtat   12660
aagctttggc cttagcttaa tgtcagtagt agaacaattt actaatgtat gtcctaacag   12720
aattattctc atacctaagc ttaatgagat acatttgatg aaacctccca tattcacagg   12780
tgatgttgat attcacaagt taaaacaagt gatacaaaaa cagcatatgt ttttaccaga   12840
caaaataagt ttgactcaat atgtggaatt attcttaagt aacaaaacac tcaaatctgg   12900
atctcatgtt aattctaatt taatattggc acataaaata tctgactatt tcataatac    12960 ttacatttta agtactaatt tagctggaca ttggattcta attatacaac ttatgaaaga   13020
ttctaaaggt attttttgaaa aagattgggg agagggatat ataactgatc atatgttat    13080 taatttgaaa gttttcttca atgcttataa gacctatctc ttgtgttttc ataaaggtta   13140
tggcaaagca aaactggagt gtgatatgaa cacttcagat cttctatgtg tattggaatt   13200
aatagacagt agttattgga agtctatgtc taaggtattt ttagaacaaa agttatcaa    13260 atacattctt agccaagatg caagtttaca tagagtaaaa ggatgtcata gcttcaaatt   13320
atggtttctt aaacgtctta atgtagcaga atttacagtt tgcccttggg ttgttaacat   13380
agattatcat ccaacacata tgaaagcaat attaacttat atagatcttg ttagaatggg   13440
attgataaat atagatagaa tacacattaa aaataaacac aaattcaatg atgaatttta   13500
tacttctaat ctcttttaca ttaattataa cttctcagat aatactcatc tattaactaa   13560
acatataagg attgctaatt cagaattaga aaataattac aacaaattat atcatcctac   13620
accagaaacc ctagagaata tactagccaa tccgattaaa agtaatgaca aaagacact    13680 gaacgactat tgtataggta aaaatgttga ctcaataatg ttaccattgt tatctaataa   13740
gaagcttgtt aaatcgtctg caatgattag aaccaattac agcaaacaag acctgtacaa   13800
tctattccct acggttgtga tcgatagaat tatagatcat tcaggtaata cagccaaatc   13860
caaccaactt tacactacta cttcccatca aatatcttta gtgcacaata gcacatcact   13920
```
ttattgcatg cttccttggc atcatattaa tagattcaat tttgtattta gttctacagg 13980
ttgtaaaatt agtatagagt atattttaaa agaccttaaa attaaagatc ctaagtgtat 14040
agcattcata ggtgaaggag cagggaattt attattgcgt acagtggtgg aacttcatcc 14100
tgacataaga tatatttaca gaagtctgaa agattgcaat gatcatagtt tacctattga 14160
gtttttaagg ctatacaatg gacatatcaa cattgattat ggtgaaaatt tgaccattcc 14220
tgctacagat gcaaccaaca acattcattg gtcttattta catataaagt ttgctgaacc 14280
tatcagtctt tttgtatgtg atgccgaatt gcctgtaaca gtcaactgga gtaaaattat 14340
aatagaatgg agcaagcatg taagaaaatg caagtactgt tcctcagtta ataaatgtac 14400
gttaatagta aaatatcatg ctcaagatga tattgatttc aaattagaca atataactat 14460
attaaaaact tatgtatgct taggcagtaa gttaaaggga tcggaggttt acttagtcct 14520
tacaataggt cctgcaaata tatttccagt atttaatgta gtgcaaaatg ctaaattgat 14580
actatcaaga accaaaaatt tcatcatgcc taagaaagct gataaagagt ctattgatgc 14640
aaatattaaa agtttgatac cctttctttg ttaccctata acaaaaaaag gaattaatac 14700
tgcattgtca aaactaaaga gtgttgttag tggagatata ctatcatatt ctatagctgg 14760
acggaatgaa gttttcagca ataaacttat aaatcataag catatgaaca tcttaaagtg 14820
gttcaatcat gttttaaatt tcagatcaac agaactaaac tataaccatt tatatatggt 14880
agaatctaca tatccttacc taagtgaatt gttaaacagc ttgacaacta atgaacttaa 14940
aaaactgatt aaaatcacag gtagtctgtt atacaacttt cataatgaat aatgaataaa 15000
gatcttataa taaaaattcc tatagctata cactagcact gtattcaatt atagttatta 15060
aaaaattaaa aatcatataa tttttataa aaataacttt tagtgaacta atcctaaagt 15120
tatcattttg atctaggagg aataaattta aatcccaatc taattggttt atatgtgtat 15180
taactaaact a 15191

<210> SEQ ID NO 4
<211> LENGTH: 15226
<212> TYPE: DNA
<213> ORGANISM: Human respiratory syncytial virus

<400> SEQUENCE: 4
acgcgaaaaa atgcgtacaa caaacttgcg taaaccaaaa aaatggggca aataagaatt 60
tgataagtac cacttaaatt taactccctt ggttagagat gggcagcaat tcgttgagta 120
tgataaaagt tagattacaa aatttgtttg acaatgatga agtagcattg ttaaaaataa 180
catgctatac tgacaaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtgctacaa aatggaggtt 360
atatatggga aatgatggaa ttaacacatt gctctcaacc taatggtcta atagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactagcacc attagttaat ataaaactta acagaagaca aaaatggggc 600
aaataaatca actcagccaa cccaaccatg gacacaaccc acaatgatac cacaccacaa 660
agactgatga tcacagacat gagaccgttg tcacttgaga ctacaataac atcactaacc 720
agagacatca taacacacag atttatatac ttaataaatc atgaatgcat agtgagaaaa 780
cttgatgaaa gacaggccac atttacattc ctggtcaact atgaaatgaa actattgcac 840

```
aaagtaggaa gcactaaata taaaaaatat actgaataca acacaaaata tggcactttc      900
cctatgccga tattcatcaa tcatgatggg ttcttagaat gcattggcat taagcctaca      960
aagcatactc ccataatata caagtatgat ctcaatccat gaatttcaac acaagattca     1020
cacaatccaa aacaacaact ttatgcataa ctacactcca tagtccaaat ggagcctgaa     1080
aattatagta atttaaaatt aaggagagac ataagataga agatgggca aatacaaaga      1140 tggctcttag caaagtcaag ttgaatgata cactcaacaa agatcaactt ctgtcatcta     1200
gcaaatacac catccaacgg agcacaggag atagtattga tactcctaat tatgatgtgc     1260
agaaacacat caataagtta tgtggcatgt tattaatcac agaagatgct aatcataaat     1320
tcactgggtt aataggtatg ttatatgcta tgtctaggtt aggaagagaa gacaccataa     1380
aaatactcag agatgcggga tatcatgtaa aagcaaatgg agtagatgta acaacacatc     1440
gtcaagacat caatgggaaa gaaatgaaat ttgaagtgtt aacattggca agcttaacaa     1500
ctgaaattca aatcaacatt gagatagaat ctagaaaatc ctacaaaaaa atgctaaaag     1560
aaatgggaga ggtagctcca gaatacaggc atgattctcc tgattgtggg atgataatat     1620
tatgtatagc agcattagta ataaccaaat tggcagcagg ggatagatct ggtcttacag     1680
ccgtgattag gagagctaat aatgtcctaa aaaatgaaat gaaacgttac aaaggcttac     1740
tacccaagga tatagccaac agcttctatg aagtgtttga aaaacatccc cactttatag     1800
atgtttttgt tcattttggt atagcacaat cttccaccag aggtggcagt agagttgaag     1860
ggatttttgc aggattgttt atgaatgcct atggtgcagg gcaagtaatg ctacggtggg     1920
gagtcttagc aaaatcagtt aaaaatatta tgttaggaca tgctagtgtg caagcagaaa     1980
tggaacaagt tgttgaggtt tatgaatatg cccaaaaatt gggtggagaa gcaggattct     2040
accatatatt gaacaaccca aaagcatcat tattatcttt gactcaattt cctcactttt     2100
ccagtgtagt attaggcaat gctgctggcc taggcataat gggagagtac agaggtacac     2160
cgaggaatca agatctatat gatgcagcaa aggcatatgc tgaacaactc aaagaaaatg     2220
gtgtgattaa ctacagtgta ttagacttga cagcagaaga actagaggct atcaaacatc     2280
agcttaatcc aaaagataat gatgtagagc tttgagttaa taaaaaatgg ggcaaataaa     2340
tcatcatgga aaagtttgct cctgaattcc atggagaaga tgcaaacaac agggctacta     2400
aattcctaga atcaataaag ggcaaattca catcacctaa agatcccaag aaaaagata      2460 gtatcatatc tgtcaactca atagatatag aagtaaccaa agaaagccct ataacatcaa     2520
attcaaccat tattaaccca acaaatgaga cagatgataa tgcagggaac aagcccaatt     2580
atcaaagaaa acctctagta agtttcaaag aagaccctat accaagtgat aatccctttt     2640
caaaactata caaagaaacc atagagacat tgataacaa tgaagaagaa tctagctatt      2700
catatgaaga aataaatgat cagacgaacg ataatataac tgcaagatta gataggattg     2760
atgaaaaatt aagtgaaata ctaggaatgc ttcacacatt agtagtagca agtgcaggac     2820
ctacatctgc tagggatggt ataagagatg ccatggttgg tttaagagaa gaaatgatag     2880
aaaaaatcag aactgaagca ttaatgacca atgacagatt agaagctatg gcaagactca     2940
ggaatgagga aagtgaaaag atggcaaaag acacatcaga tgaagtgtct ctcaatccaa     3000
catcagagaa attgaacaac ctgttggaag ggaatgatag tgacaatgat ctatcacttg     3060
aagatttctg attagttaca aatctgcact tcaacacaca acaccaacag aagaccaaca     3120
aacaaaccaa cccactcatc caaccaaaca tccatccgcc aatcagccaa acagccaaca     3180
```

```
aaacaaccag ccaatccaaa accagccacc tggaaaaaat cgacaatata gttacaaaaa    3240
aagaaaaggg tggggcaaat atggaaacat acgtgaacaa gcttcacgaa ggctccacat    3300
acacagctgc tgttcaatac aatgtcctag aaaaagacga tgaccctgca tcacttacaa    3360
tatgggtgcc catgttccaa tcatctatgc cagcagattt acttataaaa gaactagcta    3420
atgtcaacat actagtgaaa caaatatcca cacccaaggg accttcacta agagtcatga    3480
taaactcaag aagtgcattg ctagcacaaa tgcccagcaa atttaccata tgtgctaatg    3540
tgtccttgga tgaaagaagc aaactggcat atgatgtaac cacaccctgt gaaatcaagg    3600
catgtagtct aacatgccta aaatcaaaaa atatgttaac tacagttaaa gatctcacta    3660
tgaagacact caaccccaca catgatatta ttgctttatg tgaatttgaa aacatagtaa    3720
catcaaaaaa agtcataata ccaacatacc taagatccat cagtgtcaga aataagatc    3780
tgaacacact tgaaaatata caaccactg aattcaaaaa tgccatcaca aatgcaaaaa    3840
tcatccctta ctcaggatta ctattagtca tcacagtgac tgacaacaaa ggagcattca    3900
aatacataaa gccgcaaagt caattcatag tagatcttgg agcttaccta gaaaagaaa    3960
gtatatatta tgttaccaca aattggaagc acacagctac acgatttgca atcaaaccca    4020
tggaagatta acctttttcc tccacatcag tgagtcaatt catacaaaact ttctacctac    4080
attcttcact tcaccattac aatcacaaac actctgtggt tcaaccaatc aaacaaaact    4140
tatctgaagt ctcagatcat cccaagtcat tgttcatcag atctagtaat caaataagtt    4200
aataaaaata tacacatggg gcaaataatc atcggaggaa atccaactaa tcacaatatc    4260
tgttaacata gacaagtcaa cacaccagac agaatcaacc aatggaaaat acatccataa    4320
caatagaatt ctcaagcaaa ttctggcctt actttacact aatacacatg atcacaacaa    4380
taatctcttt gctaatcata atctccatca tgactgcaat actaaacaaa ctttgtgaat    4440
ataacgtatt ccataacaaa acctttgagt taccaagagc tcgagtcaac acatagcatt    4500
catcaatcta atagctcaaa atagtaacct tgcatttaaa agtgaacaac ccccaccctct    4560
ttacaacacc tcattaacat cccaccatgc aaaccaccat ccatactata agtagttaa    4620
ttaaaaatag tcataacaat gaactaggat atcaagacta acaataacgt tggggcaaat    4680
gcaaacatgt ccaaaaacaa ggaccaacgc accgctaaga cactagaaaa gacctgggac    4740
actctcaatc atttattatt catatcatcg ggcttatata agttaaatct taaatctata    4800
gcacaaatca cattatccat tctggcaatg ataatctcaa cttcacttat aattacagcc    4860
atcatattca tagcctcggc aaaccacaaa gtcacactaa caactgcaat catacaagat    4920
gcaacaagcc agatcaagaa cacaacccca acatacctca ctcaggatcc tcagcttgga    4980
atcagcttct ccaatctgtc tgaaattaca tcacaaacca ccaccatact agcttcaaca    5040
acaccaggag tcaagtcaaa cctgcaaccc acaacagtca agactaaaaa cacaacaaca    5100
acccaaacac aacccagcaa gcccactaca aacaacgcc aaaacaaacc accaaacaaa    5160
cccaataatg attttcactt cgaagtgttt aactttgtac cctgcagcat atgcagcaac    5220
aatccaacct gctgggctat ctgcaaaaga ataccaaaca aaaaccagg aagaaaacc    5280
accaccaagc ctacaaaaaa accaaccttc aagacaacca aaaagatct caaacctcaa    5340
accactaaac caaaggaagt acccaccacc aagcccacag aagagccaac catcaacacc    5400
accaaaacaa acatcacaac tacactgctc accaacaaca ccacaggaaa tccaaaactc    5460
acaagtcaaa tggaaacctt ccactcaacc tcctccgaag gcaatctaag cccttctcaa    5520
gtctccacaa catccgagca cccatcacaa ccctcatctc cacccaacac aacacgccag    5580
```

```
tagttattaa aaaacatatt atcacaaaag gccatgacca actcaaacag aatcaaaata   5640
aactctgggg caaataacaa tggagttgcc aatcctcaaa gcaaatgcaa ttaccacaat   5700
cctcgctgca gtcacatttt gctttgcttc tagtcaaaac atcactgaag aattttatca   5760
atcaacatgc agtgcagtta gcaaaggcta tcttagtgct ctaagaactg gttggtatac   5820
tagtgttata actatagaat taagtaatat caaggaaaat aagtgtaatg aacagatgc    5880 taaggtaaaa ttgataaacc aagaattaga taaatataaa aatgctgtaa cagaattgca   5940
gttgctcatg caaagcacaa cagcagcaaa caatcgagcc agaagagaac taccaaggtt   6000
tatgaattat acactcaaca ataccaaaaa aaccaatgta acattaagca agaaaaggaa   6060
aagaagattt cttggttttt tgttaggtgt tggatctgca atcgccagtg gcattgctgt   6120
atctaaggtc ctgcacttag aaggagaagt gaacaagatc aaaagtgctc tactatccac   6180
aaacaaggcc gtagtcagct tatcaaatgg agttagtgtc ttaaccagca agtgttaga    6240 cctcaaaaac tatatagata aacaattgtt acctattgtg aataagcaaa gctgcagaat   6300
atcaaatata gaaactgtga tagagttcca acaaagaaac aacagactac tagagattac   6360
cagggaattt agtgttaatg caggtgtaac tacacctgta agcacttaca tgttaactaa   6420
tagtgaatta ttgtcattaa tcaatgatat gcctataaca aatgatcaga aaagttaat    6480 gtccaacaat gttcaaatag ttagacagca aagttactct atcatgtcca taataaaga    6540 ggaagtctta gcatatgtag tacaattacc actatatggt gtgatagata caccttgttg   6600
gaaattacac acatcccctc tatgtacaac caacacaaaa gaagggtcaa acatctgttt   6660
aacaagaact gacagaggat ggtactgtga caatgcagga tcagtatctt tcttcccaca   6720
agctgaaaca tgtaaagttc aatcgaatcg agtattttgt gacacaatga acagtttaac   6780
attaccaagt gaagtaaatc tctgcaatgt tgacatattc aatcccaaat atgattgtaa   6840
aattatgact tcaaaaacag atgtaagcag ctccgttatc acatctctag gagccattgt   6900
gtcatgctat ggcaaaacta aatgtacagc atccaataaa aatcgtggaa tcataaagac   6960
attttctaac gggtgtgatt atgtatcaaa taagggggtg acactgtgt ctgtaggtaa    7020 cacattatat tatgtaaata gcaagaagg caaaagtctc tatgtaaaag gtgaaccaat    7080
aataaatttc tatgacccat tagtattccc ctctgatgaa tttgatgcat caatatctca   7140
agtcaatgag aagattaacc agagtttagc atttattcgt aaatccgatg aattattaca   7200
tcatgtaaat gctggtaaat caaccacaaa tatcatgata actactataa ttatagtgat   7260
tatagtaata ttgttatcat taattgctgt tggactgctc ctatactgta aggccagaag   7320
cacaccagtc acactaagca aggatcaact gagtggtata aataatattg catttagtaa   7380
ctgaataaaa atagcaccta atcatgttct tacaatggtt tactatctgc tcatagacaa   7440
cccatctatc attggatttt cttaaaatct gaacttcatc gaaactctta tctataaacc   7500
atctcactta cactatttaa gtagattcct agtttatagt tatataaaac acaattgaat   7560
accagattaa cttactatct gtaaaaatga gaactggggc aaatatgtca cgaaggaatc   7620
cttgcaaatt tgaaattcga ggtcattgct tgaatggtaa gagatgtcat tttagtcata   7680
attattttga atggccaccc catgcactgc tcgtaagaca aaactttatg ttaaacagaa   7740
tacttaagtc tatggataaa agtatagata ccttatcaga aataagtgga gctgcagagt   7800
tggacagaac agaagagtat gctcttggtg tagttggagt gctagagagt tatataggat   7860
caataaataa tataactaaa caatcagcat gtgttgccat gagcaaactc ctcactgaac   7920
```

```
tcaatagtga tgatatcaaa aaactgagag acaatgaaga gctaaattca cccaagataa      7980
gagtgtacaa tactgtcata tcatatattg aaagcaacag gaaaaacaat aaacaaacta      8040
tccatctgtt aaaaagattg ccagcagacg tattgaagaa aaccatcaaa aacacattgg      8100
atatccacaa gagcataacc atcaacaacc caaagaatt aactgttagt gatacaaatg       8160
accatgccaa aataatgat actacctgac aaatatcctt gtagtataac ttccatacta       8220
ataacaagta gatgtagagt cactatgtat aatcgaaaga acacactata tttcaatcaa      8280
aacaacccaa ataaccatat gtactcaccg aatcaaacat tcaatgaaat ccattggacc      8340
tcacaagact tgattgacac aattcaaaat tttctacagc atctaggtgt tattgaggat      8400
atatatacaa tatatatatt agtgtcataa cactcaatcc taatactgac catatcgttg      8460
aattattaat tcaaataatt caagctgtgg gacaaaatgg atcccattat taatggaaat      8520
tctgctaatg tttatctaac cgatagttat ttaaaaggtg ttatctcttt ctcagagtgt      8580
aatgctttag gaagttacat attcaatggt ccttatctca aaaatgatta taccaactta      8640
attagtagac aaaatccatt aatagaacac atgaatctaa agaaactaaa tataacacag      8700
tccttaatat ctaagtatca taaaggtgaa ataaaattag aagagcctac ttattttcag      8760
tcattactta tgcatacaa gagtatgacc tcgttggaac agattgctac cactaattta       8820
cttaaaaaga taataagaag agctatagaa ataagtgatg tcaaagtcta tgctatattg      8880
aataaactag ggcttaaaga aaggacaag attaaatcca acaatggaca ggatgaagac       8940
aactcagtta ttacgaccat aatcaaagat gatatacttt cagctgttaa ggataatcaa      9000
tctcatctta aagcagacaa aaatcactct acaaaacaaa aagacacaat caaaacaaca      9060
ctcttgaaga aattaatgtg ttcaatgcag catcctccat catggttaat acattggttt      9120
aatttataca caaaattaaa caacatatta acacagtatc gatcaaatga ggttaaaaac      9180
catgggttta tattgataga taatcaaact cttagtggat ttcaatttat tttgaatcaa      9240
tatgttgta tagtttatca taaggaactc aaaagaatta ctgtgacaac ctataatcaa       9300
ttcttgacat ggaaagatat tagccttagt agattaaatg tttgtttaat tacatggatt      9360
agtaactgct tgaacacatt aaataaaagc ttaggcttaa gatgcggatt caataatgtt      9420
atcttgacac aactattcct ttatggtgat tgtatactaa agctatttca caatgagggg      9480
ttctacataa taaagaggt agagggattt attatgtctc taattttaaa tataacagaa       9540
gaagatcaat tcagaaaacg atttttataat agtatgctca acaacatcac agatgctgct      9600
aataaagctc agaaaaatct gctatcaaga gtatgtcata cattattaga taagacagta      9660
tccgataata taataaatgg cagatggata attctattaa gtaagttcct taaattaatt      9720
aagcttgcag gtgacaataa ccttaacaat ctgagtgaac tatatttttt gttcagaata      9780
tttggacacc caatggtaga tgaaagacaa gccatggatg ctgttaaagt taattgcaat      9840
gagaccaaat tttacttgtt aagcagtttg agtatgttaa gaggtgcctt tatatataga      9900
attataaaag ggtttgtaaa taattacaac agatggccta ctttaagaaa tgctattgtt      9960
ttaccccttaa gatggttaac ttactataaa ctaaacactt atccttcttt gttggaactt     10020
acagaaagag atttgattgt gttatcagga ctacgtttct atcgtgagtt tcggttgcct      10080
aaaaaagtgg atcttgaaat gattataaat gataaagcta tcacccccc taaaaatttg       10140
atatggacta gtttccctag aaattatatg ccgtcacaca tacaaaacta tatagaacat      10200
gaaaaattaa aattttccga gagtgataaa tcaagaagag tattagagta ttatttaaga      10260
gataacaaat tcaatgaatg tgatttatac aactgtgtag ttaatcaaag ttatctcaac      10320
```

```
aaccctaatc atgtggtatc attgacaggc aaagaaagag aactcagtgt aggtagaatg    10380
tttgcaatgc aaccgggaat gttcagacag gttcaaatat tggcagagaa aatgatagct    10440
gaaaacattt tacaattctt tcctgaaagt cttacaagat atggtgatct agaactacaa    10500
aaaatattag aattgaaagc aggaataagt aacaaatcaa atcgctacaa tgataattac    10560
aacaattaca ttagtaagtg ctctatcatc acagatctca gcaaattcaa tcaagcattt    10620
cgatatgaaa cgtcatgtat ttgtagtgat gtgctggatg aactgcatgg tgtacaatct    10680 ctatttcct ggttacattt aactattcct catgtcacaa taatatgcac atataggcat    10740
gcacccccct ataagagag tcatattgta gatcttaaca atgtagatga acaaagtgga    10800
ttatatagat atcacatggg tggtattgaa gggtggtgtc aaaaactatg gaccatagaa    10860
gctatatcac tattggatct aatatctctc aaagggaaat tctcaattac tgctttaatt    10920
aatggtgaca atcaatcaat agatataagc aaaccagtca gactcatgga aggtcaaact    10980
catgctcaag cagattattt gctagcatta aatagcctta aattactgta taaagagtat    11040
gcaggcatag gtcacaaatt aaaaggaact gagacttata tatcacgaga tatgcaattt    11100
atgagtaaaa caattcaaca taacggtgta tattaccctg ctagtataaa gaaagtccta    11160
agagtgggac cgtggataaa cactatactt gatgatttca aagtgagtct agaatctata    11220
ggtagtttga cacaagaatt agaatataga ggtgaaagtc tattatgcag tttaatatttt   11280 agaaatgtat ggttatataa tcaaattgct ctacaattaa aaaatcatgc gttatgtaac    11340
aataaattat atttggacat attaaaggtt ctgaaacact taaaaacctt ttttaatctt    11400
gataatattg atacagcatt aacattgtat atgaatttac ccatgttatt tggtggtggt    11460
gatcccaact tgtttatatcg aagtttctat agaagaactc ctgatttcct cacagaggct    11520
atagttcact ctgtgttcat acttagttat tatacaaacc atgacttaaa agataaactt    11580
caagatttgt cagatgatag attgaataag ttcttaacat gcataatcac gtttgacaaa    11640
aaccctaatg ctgaattcgt aacattgatg agagatcctc aagctttagg gtctgagaga    11700
caagctaaaa ttactagtga aatcaataga ctggcagtta cagaggtttt gagtacagct    11760
ccaaacaaaa tattctccaa aagtgcacaa cattataccaa ctacagagat agatctaaat    11820
gatattatgc aaaatataga acctacatat cctcacgggc taagagttgt ttatgaaagt    11880
ttaccctttt ataaagcaga gaaaatagta atcttatat caggtacaaa atctataact    11940
aacatactgg aaaagacttc tgccatagac ttaacagata ttgatagagc cactgagatg    12000
atgaggaaaa acataacttt gcttataagg atacttccat tggattgtaa cagagataaa    12060
agagaaatat tgagtatgga aaacctaagt attactgaat taagcaaata tgttagggaa    12120
agatcttggt ctttatccaa tatagttggt gttacatcac ccagtatcat gtatacaatg    12180
gacatcaaat atcaacaag cactatagct agtggcataa ttatagagaa atataatgtt    12240
aacagtttaa cacgtggtga gagaggacca actaaaccat gggttggttc atctacacaa    12300
gagaaaaaaa caatgccagt ttataataga caagttttaa ccaaaaaaca aagagatcaa    12360
atagatctat tagcaaaatt ggattgggtg tatgcatcta tagataacaa ggatgaattc    12420
atggaagaac tcagcatagg aaccctggg ttaacatatg aaaaggccaa aaaattattt    12480
ccacaatatt taagtgtcaa ctatttgcat cgccttacag tcagtagtag accatgtgaa    12540
ttccctgcat caataccagc ttatagaaca acaaattatc actttgacac tagccctatt    12600
aatcgcatat taacagaaaa gtatggtgat gaagatattg acatagtatt ccaaaactgt    12660
```

```
ataagctttg gccttagctt aatgtcagta gtagaacaat ttactaatgt atgtcctaac    12720
agaattattc tcatacctaa gcttaatgag atacatttga tgaaacctcc catattcaca    12780
ggtgatgttg atattcacaa gttaaaacaa gtgatacaaa aacagcatat gtttttacca    12840
gacaaaataa gtttgactca atatgtggaa ttattcttaa gtaacaaaac actcaaatct    12900
ggatctcatg ttaattctaa tttaatattg gcacataaaa tatctgacta ttttcataat    12960
acttacattt taagtactaa tttagctgga cattggattc taattataca acttatgaaa    13020
gattctaaag gtattttga aaaagattgg ggagagggat ataaactga tcatatgttt     13080 attaatttga aagttttctt caatgcttat aagacctatc tcttgtgttt tcataaaggt    13140
tatggcaaag caaaactgga gtgtgatatg aacacttcag atcttctatg tgtattggaa    13200
ttaatagaca gtagttattg gaagtctatg tctaaggtat ttttagaaca aaaagttatc    13260
aaatacattc ttagccaaga tgcaagttta catagagtaa aaggatgtca tagcttcaaa    13320
ttatggtttc ttaaacgtct taatgtagca gaatttacag tttgcccttg ggttgttaac    13380
atagattatc atccaacaca tatgaaagca atattaactt atagatct tgttagaatg      13440 ggattgataa atatagatag aatacacatt aaaaataaac acaaattcaa tgatgaattt    13500
tatacttcta atctctttta cattaattat aacttctcag ataatactca tctattaact    13560
aaacatataa ggattgctaa ttcagaatta gaaataatt acaacaaatt atatcatcct     13620
acaccagaaa ccctagagaa tatactagcc aatccgatta aaagtaatga caaaagaca     13680 ctgaacgact attgtatagg taaaaatgtt gactcaataa tgttaccatt gttatctaat    13740
aagaagcttg ttaaatcgtc tgcaatgatt agaaccaatt acagcaaaca agacctgtac    13800
aatctattcc ctacggttgt gatcgataga attatagatc attcaggtaa tacagccaaa    13860
tccaaccaac tttacactac tacttcccat caaatatctt tagtgcacaa tagcacatca    13920
ctttattgca tgcttccttg gcatcatatt aatagattca atttgtatt tagttctaca     13980 ggttgtaaaa ttagtataga gtatatttta aaagacctta aaattaaaga tcctaattgt    14040
atagcattca taggtgaagg agcagggaat ttattattgc gtacagtggt ggaacttcat    14100
cctgacataa gatatattta cagaagtctg aaagattgca atgatcatag tttacctatt    14160
gagtttttaa ggctatacaa tggacatatc aacattgatt atggtgaaaa tttgaccatt    14220
cctgctacag atgcaaccaa caacattcat tggtcttatt tacatataaa gtttgctgaa    14280
cctatcagtc ttttttgtatg tgatgccgaa ttgcctgtaa cagtcaactg gagtaaaatt    14340
ataatagaat ggagcaagca tgtaagaaaa tgcaagtact gttcctcagt taataaatgt    14400
acgttaatag taaaatatca tgctcaagat gatattgatt tcaaattaga caatataact    14460
atattaaaaa cttatgtatg cttaggcagt aagttaaagg gatcggaggt ttacttagtc    14520
cttacaatag gtcctgcaaa tatatttcca gtatttaatg tagtacaaaa tgctaaattg    14580
atactatcaa gaaccaaaaa tttcatcatg cctaagaaag ctgataaaga gtctattgat    14640
gcaaatatta aaagtttgat accctttctt tgttacccta taacaaaaaa aggaattaat    14700
actgcattgt caaaactaaa gagtgttgtt agtggagata tactatcata ttctatagct    14760
ggacggaatg aagttttcag caataaactt ataaatcata gcatatgaa catcttaaag    14820 tggttcaatc atgtttttaa tttcagatca acagaactaa actataacca tttatatatg    14880
gtagaatcta catatccta ccctaagtgaa ttgttaaaca gcttgacaac taatgaactt    14940
aaaaaactga ttaaaatcac aggtagtctg ttatacaact ttcataatga ataatgaata    15000
aagatcttat aataaaaatt cctatagcta tacactagca ctgtattcaa ttatagttat    15060
```

```
taaaaaatta aaaatcatat aattttttat aaaaataact tttagtgaac taatcctaaa   15120
gttatcattt tgatctagga ggaataaatt taaatcccaa tctaattggt ttatatgtgt   15180
attaactaaa ctacgagata ttagtttttg acactttttt tctcgt                 15226

<210> SEQ ID NO 5
<211> LENGTH: 2387
<212> TYPE: DNA
<213> ORGANISM: Photinus pyralis

<400> SEQUENCE: 5
ctgcagaaat aactaggtac taagcccgtt tgtgaaaagt ggccaaaccc ataaatttgg     60
caattacaat aaagaagcta aaattgtggt caaactcaca acattttta ttatatacat    120 tttagtagct gatgcttata aaagcaatat ttaaatcgta acaacaaat aaaataaaat    180 ttaaacgatg tgattaagag ccaaaggtcc tctagaaaaa ggtatttaag caacggaatt    240
cctttgtgtt acattcttga atgtcgctcg cagtgacatt agcattccgg tactgttggt    300
aaaatggaag acgccaaaaa cataaagaaa ggcccggcgc cattctatcc tctagaggat    360
ggaaccgctg gagagcaact gcataaggct atgaagagat acgccctggt tcctggaaca    420
attgcttttg tgagtatttc tgtctgattt ctttcgagtt aacgaaatgt tcttatgttt    480
ctttagacag atgcacatat cgaggtgaac atcacgtacg cggaatactt cgaaatgtcc    540
gttcggttgg cagaagctat gaaacgatat gggctgaata caaatcacag aatcgtcgta    600
tgcagtgaaa actctcttca attctttatg ccggtgttgg gcgcgttatt tatcggagtt    660
gcagttgcgc ccgcgaacga catttataat gaacgtaagc accctcgcca tcagaccaaa    720
gggaatgacg tatttaattt ttaaggtgaa ttgctcaaca gtatgaacat ttcgcagcct    780
accgtagtgt ttgtttccaa aaaggggttg caaaaaattt tgaacgtgca aaaaaaatta    840
ccaataatcc agaaaattat tatcatggat tctaaaacgg attaccaggg atttcagtcg    900
atgtacacgt tcgtcacatc tcatctacct cccggtttta atgaatacga ttttgtacca    960
gagtcctttg atcgtgacaa acaattgcac tgataatga attcctctgg atctactggg   1020
ttacctaagg gtgtggccct tccgcataga actgcctgcg tcagattctc gcatgccagg   1080
tatgtcgtat aacaagagat taagtaatgt tgctacacac attgtagaga tcctattttt   1140
ggcaatcaaa tcattccgga tactgcgatt ttaagtgttg ttccattcca tcacggtttt   1200
ggaatgttta ctacactcgg atatttgata tgtggatttc gagtcgtctt aatgtataga   1260
tttgaagaag agctgttttt acgatccctt caggattaca aaattcaaag tgcgttgcta   1320
gtaccaaccc tattttcatt cttcgccaaa agcactctga ttgacaaata cgatttatct   1380
aatttacacg aaattgcttc tgggggcgca cctctttcga agaagtcgg ggaagcggtt   1440 gcaaaacggt gagttaagcg cattgctagt atttcaaggc tctaaaacgg cgcgtagctt   1500
ccatcttcca gggatacgac aaggatatgg gctcactgag actacatcag ctattctgat   1560
tacacccgag ggggatgata aaccgggcgc ggtcggtaaa gttgttccat tttttgaagc   1620
gaaggttgtg gatctggata ccgggaaaac gctgggcgtt aatcagagag gcgaattatg   1680
tgtcagagga cctatgatta tgtccggtta tgtaaacaat ccggaagcga ccaacgcctt   1740
gattgacaag gatggatggc tacattctgg agacatagct tactgggacg aagacgaaca   1800
cttcttcata gttgaccgct tgaagtcttt aattaaatac aaaggatatc aggtaatgaa   1860 gattttaca tgcacacacg ctacaatacc tgtaggtggc ccccgctgaa ttggaatcga   1920
```

| | |
|---|---:|
| tattgttaca acaccccaac atcttcgacg cgggcgtggc aggtcttccc gacgatgacg | 1980 |
| ccggtgaact tcccgccgcc gttgttgttt tggagcacgg aaagacgatg acggaaaaag | 2040 |
| agatcgtgga ttacgtcgcc agtaaatgaa ttcgttttac gttactcgta ctacaattct | 2100 |
| tttcataggt caagtaacaa ccgcgaaaaa gttgcgcgga ggagttgtgt ttgtggacga | 2160 |
| agtaccgaaa ggtcttaccg gaaaactcga cgcaagaaaa atcagagaga tcctcataaa | 2220 |
| ggccaagaag ggcggaaagt ccaaattgta aaatgtaact gtattcagcg atgacgaaat | 2280 |
| tcttagctat tgtaatatta tatgcaaatt gatgaatggt aattttgtaa ttgtgggtca | 2340 |
| ctgtactatt ttaacgaata ataaaatcag gtataggtaa ctaaaaa | 2387 |

<210> SEQ ID NO 6
<211> LENGTH: 954
<212> TYPE: DNA
<213> ORGANISM: Artificial Sequence
<220> FEATURE:
<223> OTHER INFORMATION: Synthetic Construct

<400> SEQUENCE: 6

| | |
|---|---:|
| gatactcgag atggccagca aggtgtacga ccccgagcag cgcaagcgca tgatcaccgg | 60 |
| ccctcagtgg tgggctcgct gcaagcagat gaacgtgctg gacagcttca tcaactacta | 120 |
| cgacagcgag aagcacgccg agaacgccgt gatcttcctg cacggcaacg ccgccagcag | 180 |
| ctacctgtgg cgccacgtgg tgccccacat cgagcccgtg gcccgctgca tcatccccga | 240 |
| cctgatcggc atgggcaaga gcggcaagag cggcaacggc agctaccgcc tgctggacca | 300 |
| ctacaagtac ctgaccgcct ggttcgagct gctgaacctg cccaagaaga tcatcttcgt | 360 |
| gggccacgac tggggcgcct gcctggcctt ccactacagc tacgagcacc aggacaagat | 420 |
| caaggccatc gtgcacgccg agagcgtggt ggacgtgatc gagagctggg acgagtggcc | 480 |
| cgacatcgag gaggacatcg ccctgatcaa gagcgaggag ggcgagaaga tggtgctgga | 540 |
| gaacaacttc ttcgtggaga ccatgctgcc cagcaagatc atgcgcaagc tggagcccga | 600 |
| ggagttcgcc gcctacctgg agcccttcaa ggagaagggc gaggtgcgcc gtcccaccct | 660 |
| gagctggcct cgcgagatcc ccctggtgaa gggcggcaag cccgacgtgg tgcagatcgt | 720 |
| gcgcaactac aacgcctacc tgcgcgccag cgacgacctg cccaagatgt tcatcgagag | 780 |
| cgaccccggc ttcttcagca cgccatcgt ggagggcgcc aagaagttcc ccaacaccga | 840 |
| gttcgtgaag gtgaagggcc tgcacttcag ccaggaggac gctcccgacg agatgggcaa | 900 |
| gtacatcaag agcttcgtgg agcgcgtgct gaagaacgat acgtaaggat cccg | 954 |

<210> SEQ ID NO 7
<211> LENGTH: 1149
<212> TYPE: DNA
<213> ORGANISM: Artificial Sequence
<220> FEATURE:
<223> OTHER INFORMATION: Synthetic Construct

<400> SEQUENCE: 7

| | |
|---|---:|
| atgtctagag tgagcaaggg cgaggagctg ttcaccgggg tggtgcccat cctggtcgag | 60 |
| ctggacggcg acgtaaacgg ccacaagttc agcgtgtccg gcgagggcga gggcgatgcc | 120 |
| acctacggca agctgaccct gaagttcatc tgcaccaccg gcaagctgcc cgtgccctgg | 180 |
| cccaccctcg tgaccaccct gacctacggc gtgcagtgct tcagccgcta ccccgaccac | 240 |
| atgaagcagc acgacttctt caagtccgcc atgcccgaag ctacgtcca ggaggtagat | 300 |
| ttatgcatcc tcttgtcatg agaagtcgaa ttgttcccat tctgtgtgtt gcagctacag | 360 |

```
atggagatac atagagatac tcgtggattt tgcttagtgt tgagttttgt tctggttgtg    420
aactaaaagt ttatacattt gcaggaaata aatagccttt tgtttaaatc aaaaggtctt    480
acctatgtta ttgcgtgagg cattggatcc caaagagaga actccaaaat gcgaggctac    540
atgttatgga ctagtatcag gttggggagac ctcctgagaa gctccagcaa gtaagcctcg    600
atcacgcaaa atgtttgagg tctgatgttc aatagcttgt tttgtttcac tttgctttgg    660
actttctttt cgccaatgag ctatgttcct gatggttttc actcttttgg tgtgtagaga    720
accatcttct tcaaggacga cggcaactac aagacccgcg ccgaggtgaa gttcgagggc    780
gacaccctgg tgaaccgcat cgagctgaag ggcatcgact tcaaggagga cggcaacatc    840
ctggggcaca agctggagta caactacaac agccacaacg tctatatcat ggccgacaag    900
cagaagaacg gcatcaaggt gaacttcaag atccgccaca acatcgagga cggcagcgtg    960
cagctcgccg accactacca gcagaacacc cccatcggcg acggccccgt gctgctgccc   1020
gacaaccact acctgagcac ccagtccgcc ctgagcaaag accccaacga gaagcgcgat   1080
cacatggtcc tgctggagtt cgtgaccgcc gccgggatca ctctcggcat ggacgagctg   1140
tacaagtaa                                                           1149

<210> SEQ ID NO 8
<211> LENGTH: 3392
<212> TYPE: DNA
<213> ORGANISM: Artificial Sequence
<220> FEATURE:
<223> OTHER INFORMATION: Synthetic Construct

<400> SEQUENCE: 8
accggagtac tggtcgacct ccgaagttgg gggggagcaa aagcagggtg acaaagacat     60
aagcgaaagc aggtcaatta tattcaatat ggaaagaata aaagaactaa ggaatctaat    120
gtcgcagtct cgcactcgcg agatactcac aaaaaccacc gtggaccata tggccataat    180
caagaagtac acatcaggaa gacaggagaa gaacccagca cttaggatga atggatgat    240 ggcaatgaaa tatccaatta cagcagacaa gaggataacg gaaatgattc ctgagagaaa    300
tgagcaggga caaactttat ggagtaaaat gaatgacgcc ggatcagacc gagtgatggt    360
atcacctctg gctgtgacat ggtggaatag gaatggacca gtgacaagta cagttcatta    420
tccaaaaatc tacaaaactt attttgaaaa agtcgaaagg ttaaaacatg gaaccctttgg    480 ccctgtccat tttagaaacc aagtcaaaat acgtcgaaga gttgacataa atcctggtca    540
tgcagatctc agtgccaaag aggcacagga tgtaatcatg gaagttgttt ccctaacga    600 agtgggagcc aggatactaa catcggaatc gcaactaacg acaaccaaag agaagaaaga    660
agaactccag ggttgcaaaa tttctcctct gatggtggca tacatgttgg agagagaact    720
ggtccgcaaa acgagattcc tcccagtggc tggtggaaca agcagtgtgt acattgaagt    780
gttgcatttg acccaaggaa catgctggga acagatgtac actccaggag gggaggcgag    840
gaatgatgat gttgatcaaa gcttaattat tgctgctaga aacatagtaa aagagccac    900 agtatcagca gatccactag catctttatt ggagatgtgc acagcacgc agattggtgg    960 aataaggatg gtaaacatcc ttaggcagaa cccaacagaa gagcaagccg tggatatttg   1020
caaggctgca atgggactga gaattagctc atccttcagt tttggtggat tcacatttaa   1080
gagaacaagc ggatcatcag tcaagagaga ggaagaggtg cttacgggca atcttcagac   1140
attgaagata agagtgcatg agggatatga agagttcaca atggttggga agagagcaac   1200
```

```
agctatactc agaaaagcaa ccaggagatt gattcagctg atagtgagtg ggagagacga    1260
acagtcgatt gccgaagcaa taattgtggc catggtattt tcacaagagg attgtatgat    1320
aaaagcagtt agaggtgacc tgaatttcgt caatagggcg aatcagcgat tgaatcccat    1380
gcaccaactt ttgagacatt ttcagaagga tgcaaaggtg ctctttcaaa attggggaat    1440
tgaatccatc gacaatgtga tgggaatgat cgggatattg cccgacatga ctccaagcac    1500
cgagatgtca atgagaggag tgagaatcag caaaatgggg gtagatgagt attccagcgc    1560
ggagaagata gtggtgagca ttgaccgttt tttgagagtt agggaccaac gtgggaatgt    1620
actactgtct cccgaggaga tcagtgaaac acagggaaca gagaaactga caataactta    1680
ctcatcgtca atgatgtggg agattaatgg tcctgaatca gtgttggtca atacctatca    1740
gtggatcatc agaaactggg aaactgttaa aattcagtgg tcccagaatc ctacaatgct    1800
gtacaataaa atggaatttg agccatttca gtctttagtt ccaaaggccg ttagaggcca    1860
atacagtggg tttgtgagaa ctctgttcca acaaatgagg gatgtgcttg ggacatttga    1920
taccgctcag ataataaaac ttcttccctt cgcagccgct ccaccaaagc aaagtagaac    1980
gcagttctcc tcattgacta taaatgtgag gggatcagga atgagaatac ttgtaagggg    2040
caattctcca gtattcaact acaacaagac cactaaaaga ctcacagttc tcggaaagga    2100
tgctggccct ttaactgaag acccagatga aggcacagct ggagttgagt ccgcagttct    2160
gagaggattc ctcattctgg gcaaagaaga caggagatat ggaccagcat taagcataaa    2220
tgaactgagc aaccttgcga aaggagaaaa agccaacgta ctcatcggac aggggatgt    2280
agtattagtg atgaagcgaa agcgaaactc gagtatcctc acagatagtc aaactgccac    2340
gaagaggatc cgaatggcga tcaacggtag tggcgcaact aatttctccc tccttaagca    2400
agccggcgat gtagaagaga acccaggccc aatggtcttc acactcgaag atttcgttgg    2460
ggactggcga cagacagccg gctacaacct ggaccaagtc cttgaacagg gaggtgtgtc    2520
cagtttgttt cagaatctcg gggtgtccgt aactccgatc caaaggattg tcctgagcgg    2580
tgaaaatggg ctgaagatcg acatccatgt catcatcccg tatgaaggtc tgagcggcga    2640
ccaaatgggc cagatcgaaa aaattttaa ggtggtgtac cctgtggatg atcatcactt    2700
taaggtgatc ctgcactatg gcacactggt aatcgacggg gttacgccga acatgatcga    2760
ctatttcgga cggccgtatg aaggcatcgc cgtgttcgac ggcaaaaaga tcactgtaac    2820
agggaccctg tggaacggca acaaaattat cgacgagcgc ctgatcaacc ccgacggctc    2880
cctgctgttc cgagtaacca tcaacggagt gaccggctgg cggctgtgcg aacgcattct    2940
ggcgaaagac gagttataag agaaggctaa tgtgctaatt gggcaaggag acgtggtgtt    3000
ggtaatgaaa cggaaacgga actctagcat acttactgac agccagacag cgaccaaaag    3060
aattcggatg gccatcaatt agtgtcgaat agtttaaaaa cgaccttgtt tctacttgca    3120
agccttacaa ctattgcttg aagtgggagca agagataaga actttctcgt ttcagcttat    3180
ttaataataa aaaacacccct tgtttctact aataacccgg cggcccaaaa tgccgactcg    3240
gagcgaaaga tatacctccc ccggggccgg gaggtcgcgt caccgaccac gccgccggcc    3300
caggcgacgc gcgacacgga cacctgtccc caaaaacgcc accatcgcag ccacacacgg    3360
agcgcccggg gccctctggt caaccccagg ac                                 3392
```